United States Patent
Lampropoulos et al.

(10) Patent No.: US 11,964,136 B2
(45) Date of Patent: Apr. 23, 2024

(54) MEDICAL DEVICES FOR DELIVERING PLUGS TO VOIDS

(71) Applicant: Merit Medical Systems, Inc., South Jordan, UT (US)

(72) Inventors: Fred Lampropoulos, Salt Lake City, UT (US); Jim Mottola, West Jordan, UT (US); Richard P. Jenkins, Bluffdale, UT (US); Gregory R. McArthur, Sandy, UT (US); Kenneth Sykes, Bluffdale, UT (US); Mark Garcia, Wilmington, DE (US)

(73) Assignee: Merit Medical Systems, Inc., South Jordan, UT (US)

( * ) Notice: Subject to any disclaimer, the term of this patent is extended or adjusted under 35 U.S.C. 154(b) by 797 days.

(21) Appl. No.: 15/476,675

(22) Filed: Mar. 31, 2017

(65) Prior Publication Data

US 2017/0281151 A1    Oct. 5, 2017

Related U.S. Application Data

(60) Provisional application No. 62/429,513, filed on Dec. 2, 2016, provisional application No. 62/325,792, filed
(Continued)

(51) Int. Cl.
*A61M 5/31* (2006.01)
*A61B 17/00* (2006.01)
(Continued)

(52) U.S. Cl.
CPC ....... *A61M 5/3134* (2013.01); *A61B 17/0057* (2013.01); *A61B 17/12159* (2013.01);
(Continued)

(58) Field of Classification Search
CPC .............. A61M 5/3134; A61M 5/2053; A61M 37/0069; A61B 17/0057; A61B 17/12159;
(Continued)

(56) References Cited

U.S. PATENT DOCUMENTS 4,673,387 A   6/1987  Phillips et al.
4,842,592 A   6/1989  Caggiani et al.
(Continued)

FOREIGN PATENT DOCUMENTS

CN    101239218 A    8/2008
CN    202590137 U    12/2012
(Continued)

OTHER PUBLICATIONS

International Search Report and Written Opinion dated Aug. 17, 2017 for PCT/US2017/025565.
(Continued)

*Primary Examiner* — Jessica Arble
(74) *Attorney, Agent, or Firm* — Dorsey & Whitney LLP

(57) ABSTRACT

Medical devices for delivering a plug to a void within a patient. The medical device can include a fluid delivery device and a plug holder (e.g., a plug delivery device) coupled to a distal end of the fluid delivery device. The medical device may be configured such that the delivery of fluid from the fluid delivery device wets the plug, ejects the plug from the plug holder, and pushes the plug through a lumen of an elongate tube to a void within a patient.

14 Claims, 42 Drawing Sheets

Related U.S. Application Data on Apr. 21, 2016, provisional application No. 62/317,725, filed on Apr. 4, 2016, provisional application No. 62/317,093, filed on Apr. 1, 2016.

(51) Int. Cl.
*A61B 17/12* (2006.01)
*A61B 17/34* (2006.01)
*A61F 13/26* (2006.01)
*A61F 13/36* (2006.01)

(52) U.S. Cl.
CPC .............. *A61B 2017/00004* (2013.01); *A61B 2017/00623* (2013.01); *A61B 2017/00654* (2013.01); *A61B 2017/1205* (2013.01); *A61B 17/3468* (2013.01); *A61F 13/266* (2013.01); *A61F 13/36* (2013.01)

(58) Field of Classification Search
CPC .......... A61B 2017/00623; A61B 2017/00654; A61B 2017/00004; A61B 2017/1205; A61B 17/3468; A61B 17/00898; A61B 2017/00535; A61B 2017/00539; A61B 2017/00544; A61B 2017/00548; A61F 13/36; A61F 13/266; A61F 9/0017; A61F 9/0008

See application file for complete search history.

(56) References Cited

U.S. PATENT DOCUMENTS

| | | | |
|---|---|---|---|
| 5,163,554 A | | 11/1992 | Lampropoulos et al. |
| 5,318,522 A | | 6/1994 | D'Antonio |
| 5,395,309 A | | 3/1995 | Tanaka et al. |
| 5,681,334 A | | 10/1997 | Evans et al. |
| 5,727,320 A | | 3/1998 | Shepherd et al. |
| 5,997,500 A | | 12/1999 | Cook et al. |
| 6,071,301 A | * | 6/2000 | Cragg .................. A61B 17/0057 604/265 |
| 6,440,151 B1 | | 8/2002 | Cragg et al. |
| 6,610,026 B2 | | 8/2003 | Cragg et al. |
| 6,984,219 B2 | | 1/2006 | Ashby et al. |
| 8,911,424 B2 | * | 12/2014 | Weadock .......... A61M 25/0017 604/263 |
| 8,915,941 B2 | | 12/2014 | Obermiller et al. |
| 8,932,268 B1 | | 1/2015 | Struzinski |
| 2001/0031948 A1 | | 10/2001 | Cruise et al. |
| 2001/0056254 A1 | | 12/2001 | Cragg et al. |
| 2002/0022822 A1 | * | 2/2002 | Cragg ................ A61B 17/0057 604/500 |
| 2002/0052653 A1 | | 5/2002 | Durgin |
| 2004/0204701 A1 | | 10/2004 | Cox et al. |
| 2004/0260270 A1 | | 12/2004 | Cohen |
| 2005/0124999 A1 | | 6/2005 | Teitelbaum et al. |
| 2006/0065271 A1 | | 3/2006 | Ishizeki et al. |
| 2006/0264967 A1 | | 11/2006 | Ferreyro et al. |
| 2008/0312604 A1 | | 12/2008 | Boesen |
| 2009/0143808 A1 | | 6/2009 | Houser |
| 2010/0036414 A1 | | 2/2010 | Cragg et al. |
| 2011/0009872 A1 | | 1/2011 | Mistry et al. |
| 2011/0144661 A1 | | 6/2011 | Houser et al. |
| 2011/0144735 A1 | * | 6/2011 | Hartley .................. A61F 2/966 623/1.11 |
| 2011/0201992 A1 | | 8/2011 | Smet et al. |
| 2011/0218520 A1 | | 9/2011 | Andrich |
| 2013/0079812 A1 | | 3/2013 | Duncan et al. |
| 2013/0296828 A1 | | 11/2013 | Schon et al. |
| 2014/0148839 A1 | | 5/2014 | Pavcnik et al. |
| 2014/0257232 A1 | | 9/2014 | Mathur et al. |
| 2014/0303744 A1 | | 10/2014 | Evans et al. |
| 2014/0378951 A1 | * | 12/2014 | Dye .................. A61M 25/0068 604/544 |
| 2015/0025469 A1 | | 1/2015 | Larsen et al. |
| 2015/0142003 A1 | | 5/2015 | Giersch et al. |
| 2016/0262737 A1 | | 9/2016 | Paul, Jr. et al. |
| 2017/0281151 A1 | | 10/2017 | Lampropoulos et al. |
| 2019/0183468 A1 | | 6/2019 | Sykes et al. |
| 2020/0069299 A1 | | 3/2020 | Lampropoulos et al. |
| 2021/0338219 A1 | | 11/2021 | Lampropoulos et al. |

FOREIGN PATENT DOCUMENTS

| | | |
|---|---|---|
| CN | 204766986 U | 11/2015 |
| EP | 2514456 | 10/2012 |
| FR | 2442627 | 6/1980 |
| JP | 200687797 | 4/2006 |
| KR | 101542949 | 8/2015 |
| WO | 199956632 | 11/1999 |
| WO | 199956692 | 11/1999 |
| WO | 200187406 | 11/2001 |
| WO | 2004098420 | 11/2004 |
| WO | 2006119256 | 11/2006 |
| WO | 2011057282 | 5/2011 |
| WO | 2015025178 | 2/2015 |
| WO | 2016191539 | 12/2016 |
| WO | 2017173378 | 10/2017 |

OTHER PUBLICATIONS

European Search Report dated Oct. 16, 2019 for EP17779681.0.
European Search Report dated Oct. 29, 2019 for EP17776854.6.
Office Action dated Dec. 14, 2018 for U.S. Appl. No. 15/479,149.
International Search Report and Written Opinion dated Apr. 23, 2019 for PCT/US2018/065495.
International Search Report and Written Opinion dated Jul. 17, 2017 for PCT/US2017/025986.
Notice of Allowance dated Jan. 13, 2021 for U.S. Appl. No. 16/557,672.
European Search Report dated Jul. 9, 2021 for EP18887907.6.
Office Action dated Jun. 20, 2022 for U.S. Appl. No. 16/219,413.
Notice of Allowance dated May 4, 2023 for U.S. Appl. No. 17/202,010.
Office Action dated Sep. 1, 2023 for U.S. Appl. No. 16/219,413.
European Search Report dated Nov. 10, 2022 for EP17776854.6.
Office Action dated Jan. 23, 2023 for U.S. Appl. No. 16/219,413.

* cited by examiner

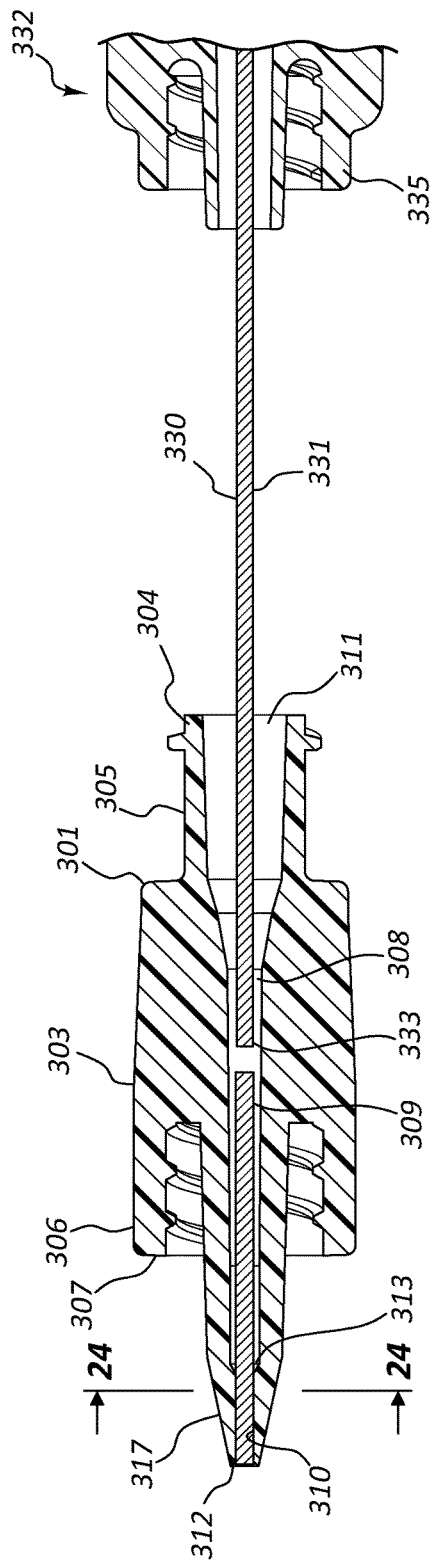
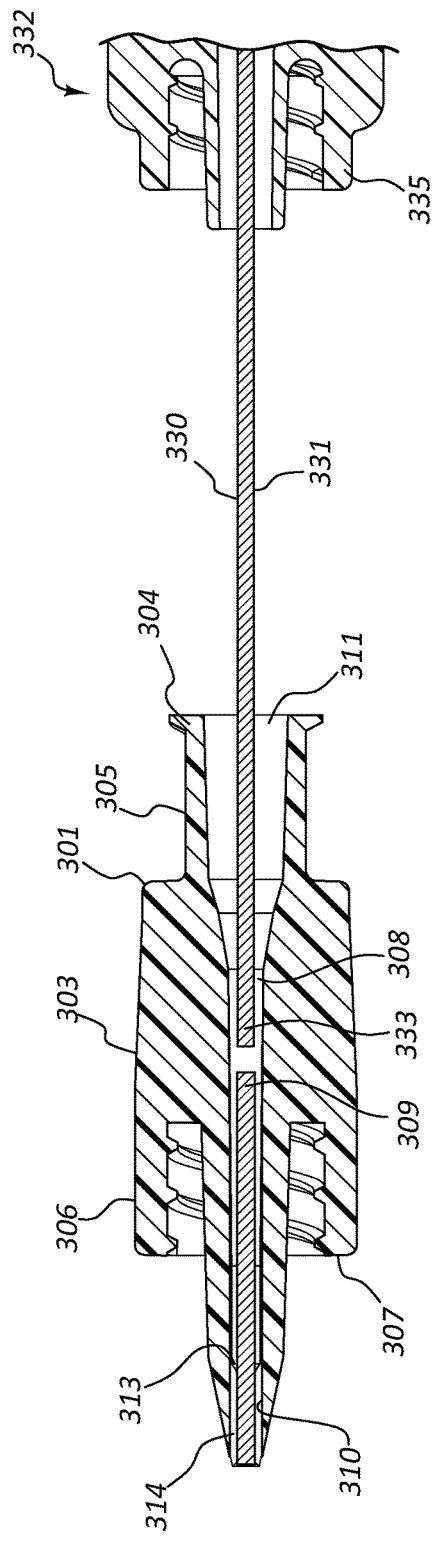
FIG. 22
FIG. 23

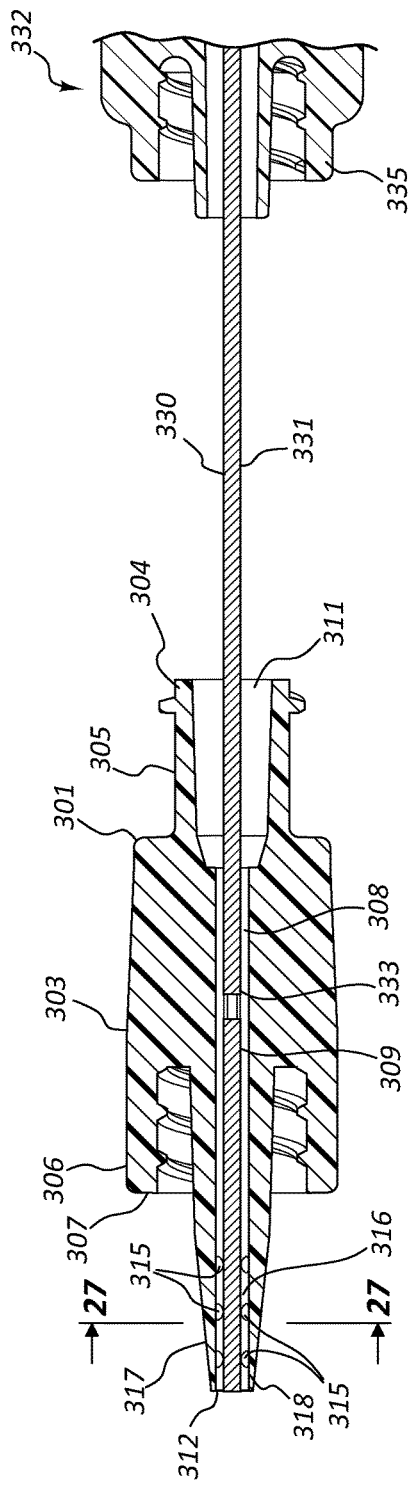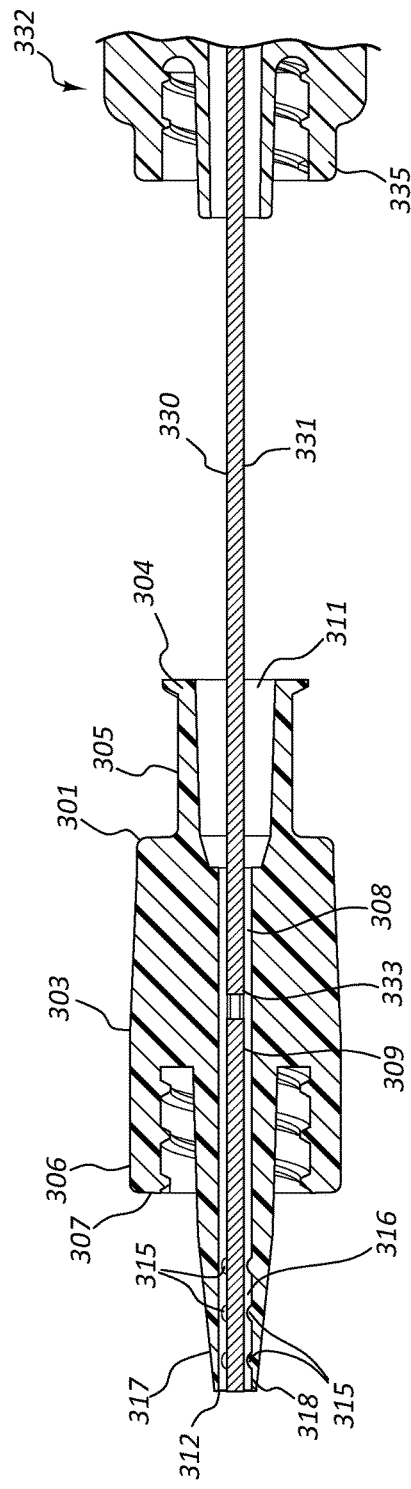
FIG. 25
FIG. 26

MEDICAL DEVICES FOR DELIVERING PLUGS TO VOIDS

CROSS REFERENCE TO RELATED APPLICATIONS

This application claims priority to U.S. Provisional Application No. 62/317,725 filed Apr. 4, 2016, titled MEDICAL DEVICES FOR DELIVERING PLUGS TO VOIDS and to U.S. Provisional Application No. 62/429,513 filed Dec. 2, 2016, titled MEDICAL DEVICES FOR DELIVERING PLUGS TO VOIDS, and to U.S. Provisional Application No. 62/317,093 filed Apr. 1, 2016, titled MEDICAL DEVICES FOR DELIVERING PLUGS TO VOIDS, and to U.S. Provisional Application No. 62/325,792 filed Apr. 21, 2016, titled DEVICES FOR DELIVERING MEDICAL PLUGS, the entire contents of each application are hereby incorporated by reference in their entireties.

TECHNICAL FIELD

The present disclosure relates generally to the field of medical devices. More particularly, some embodiments relate to medical devices for delivering a medical plug such as a pledget to at least partially fill a void. Related components and methods are also disclosed.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 22 is a cross-sectional side view of a medical plug delivery system.

FIG. 23 is another cross-sectional side view rotated 90 degrees around the longitudinal axis of a medical plug delivery system.

FIG. 25 is a cross-sectional side view of a medical plug delivery system.

FIG. 26 is another cross-sectional side view rotated 90 degrees around the longitudinal axis of a medical plug delivery system.

DETAILED DESCRIPTION

Figure 1:
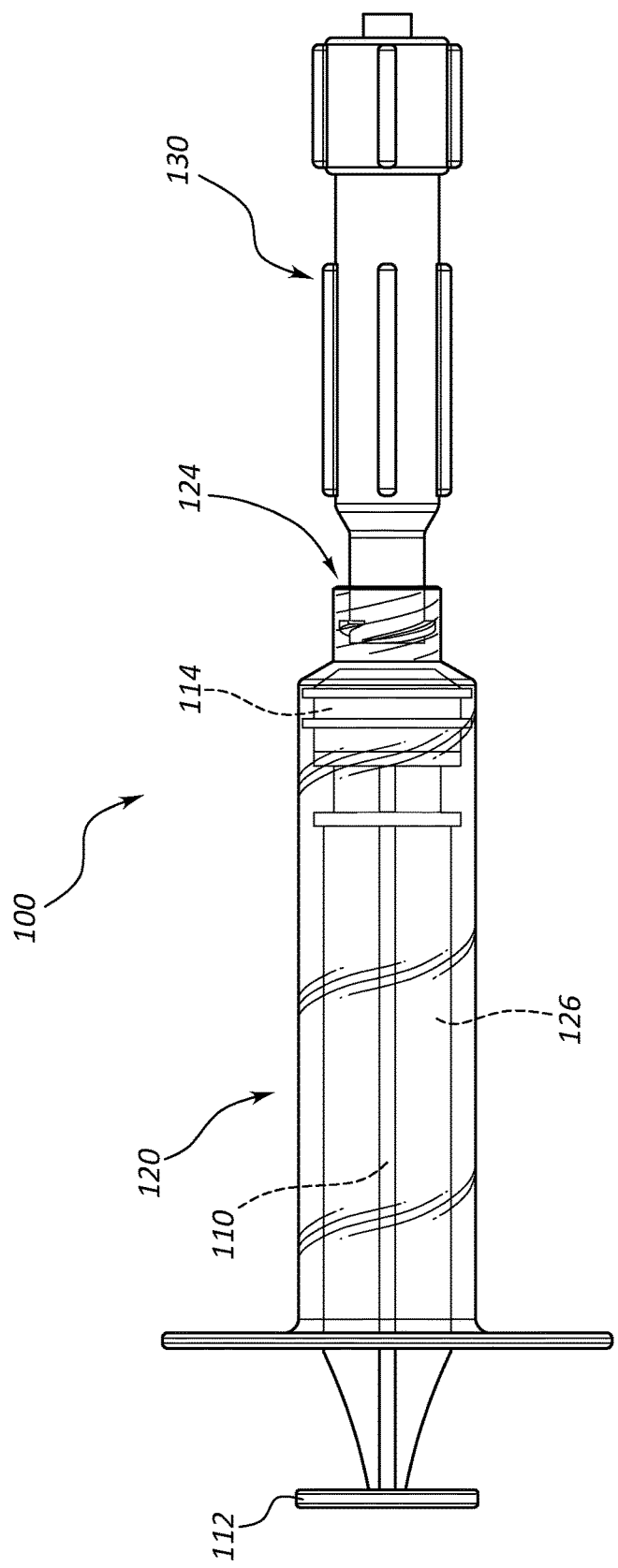
FIG. 1 is a side view of a medical device for delivering a medical plug.

Certain medical procedures include delivery of a plug (such as a pledget) into a void within a patient's body. Plugs may be inserted into a void to, inter alia, partially or completely fill a wound site, to occlude the passage of fluid through a lumen, to induce blood coagulation, to prevent or reduce leakage of biological fluid, and/or to provide a scaffold to promote and/or permit tissue growth.

For instance, during a biopsy procedure, a practitioner may insert an introducer sheath into a patient by placing a trocar within an introducer sheath such that a pointed distal end of the trocar protrudes from the distal end of the introducer sheath. With the pointed end of the trocar protruding from the introducer sheath, the trocar and the introducer sheath may together be inserted into the patient. Once the introducer sheath is positioned within the patient, the trocar may be withdrawn from the introducer sheath. At this stage of the procedure, the introducer sheath provides a conduit that allows access to a patient's internal bodily tissue.

A cutting device (e.g., a needle or some other device configured to obtain bodily samples) may then be inserted through the introducer sheath. Once the cutting device reaches the internal tissue, the cutting device may be used to excise (e.g., cut out) internal tissue from the patient. Such excision may leave behind a void in the space that was occupied by the internal tissue.

In some circumstances, it may be advantageous to deliver a plug into the void created by excised tissue from the biopsy procedure. For example, in some embodiments, a plug may be inserted into the void to at least partially fill the space created by the void, to promote blood coagulation at the wound site, and/or to provide a scaffold to promote or permit tissue regrowth.

Plugs may be inserted into a void in other medical procedures as well. For example, a plug may be delivered to block fluid flow through a lumen. In other words, a plug may be delivered as an embolic agent to prevent the flow of fluid to a particular location. Plugs may be delivered to various other locations in a patient's body, or may be delivered under alternative circumstances or for different purposes. One of ordinary skill in the art, with the benefit of this disclosure, will understand that this disclosure relates broadly to the delivery of plugs for various purposes, and is not limited to the specific contexts discussed herein.

Medical devices and related components, as described in greater detail below, may be configured to facilitate delivery of a plug into a void. In some circumstances, the medical devices are designed to facilitate wetting (e.g., hydration) of a plug and subsequent delivery of the plug through a lumen to a void within a patient.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any connection or coupling between two or more entities. Two components may be coupled to each other even though they are not in direct contact with each other. For example, two components may be coupled to each other through an intermediate component. The phrase "fluid communication" is broad enough to refer to arrangements in which a fluid can flow from one element to another element when the elements are in fluid communication with each other.

The terms "proximal" and "distal" are opposite directional terms. The distal end of a device or component is the end of the component that is furthest from the practitioner during ordinary use. The proximal end refers to the opposite end, or the end nearest the practitioner during ordinary use. The term "void" relates to a region or opening within a patient's body to which a plug may be delivered.

FIG. 1 provides a side view of an assembly or medical device 100 for delivering a plug to a void within a patient. As depicted in FIG. 1, the medical device 100 may include a plunger 110, a syringe body 120, and a plug holder 130 (which may also be referred to as a medical plug delivery device).

The plunger 110 may include a handle 112 adjacent the proximal end of the plunger 110 and a seal 114 adjacent the distal end of the plunger 110. The plunger 110 may be configured to be at least partially disposed within the syringe body 120 such that advancement and retraction of the plunger 110 causes displacement of fluid within a reservoir 126 in the syringe body 120. The syringe body 120 may be configured to couple to a proximal end of the plug holder 130. For example, in the depicted embodiment, the syringe body 120 includes a male Luer connection at its distal end 124. The plunger 110 and the syringe body 120 may be components of standard, commercially available syringes. The syringe body 120 may comprise an outlet or orifice at the distal end 124 of the syringe body 120.

Figure 2:
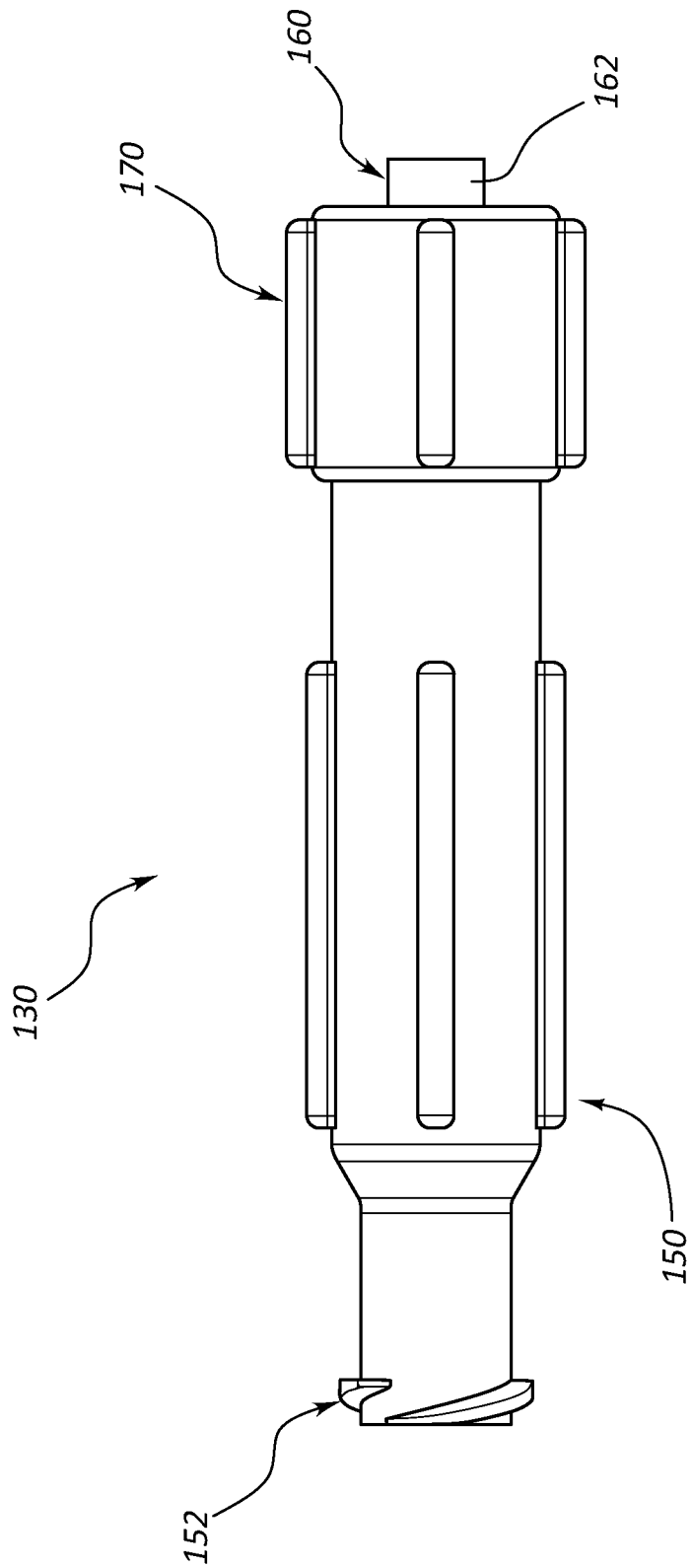
FIG. 2 is a side view of a plug holder for the medical device of FIG. 1.
Figure 3:
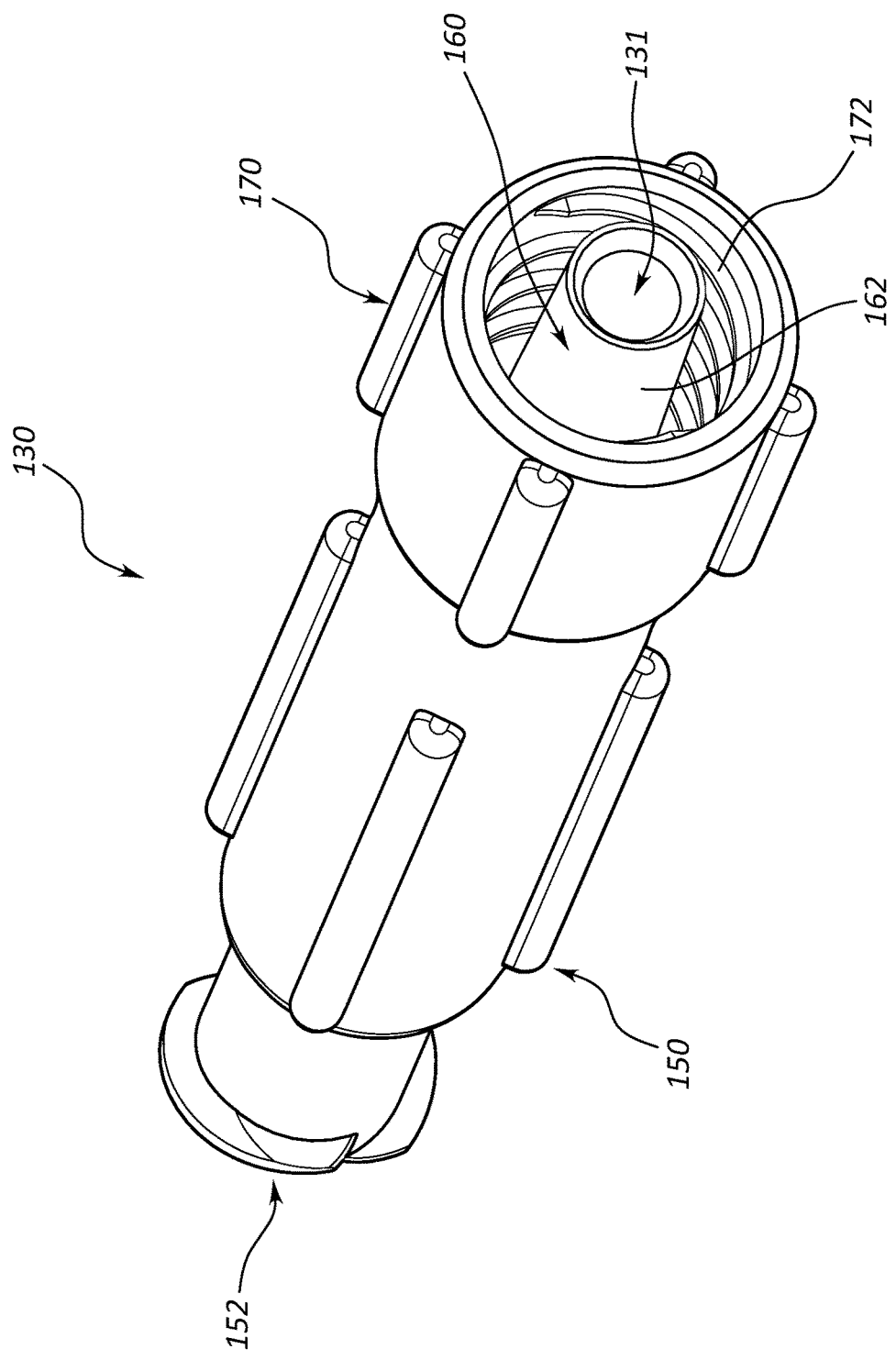
FIG. 3 is a perspective view of the plug holder of FIG. 2.
Figure 4:
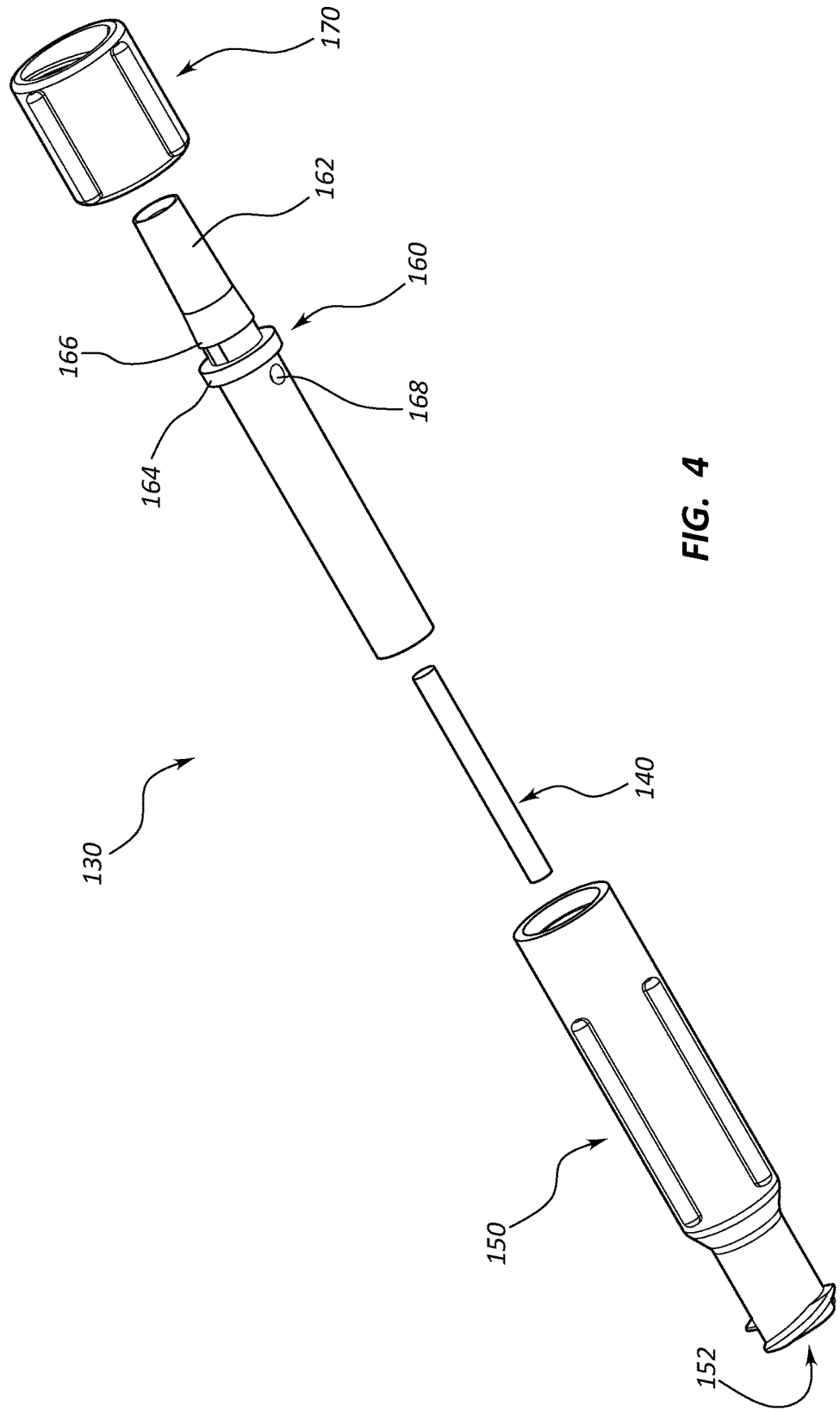
FIG. 4 is an exploded perspective view of the plug holder of FIGS. 2 and 3.
Figure 5:
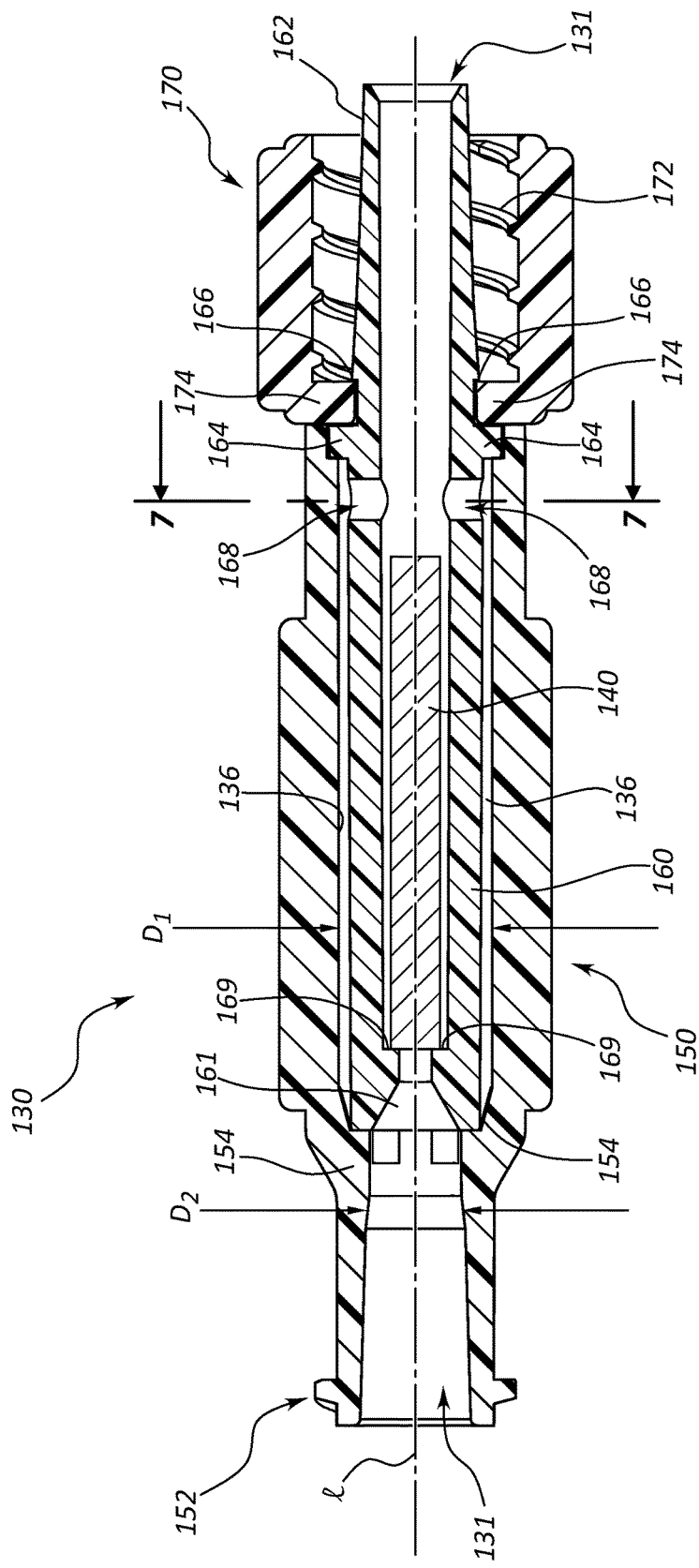
FIG. 5 is a cross-sectional side view of the plug holder of FIGS. 2-4.
Figure 6:
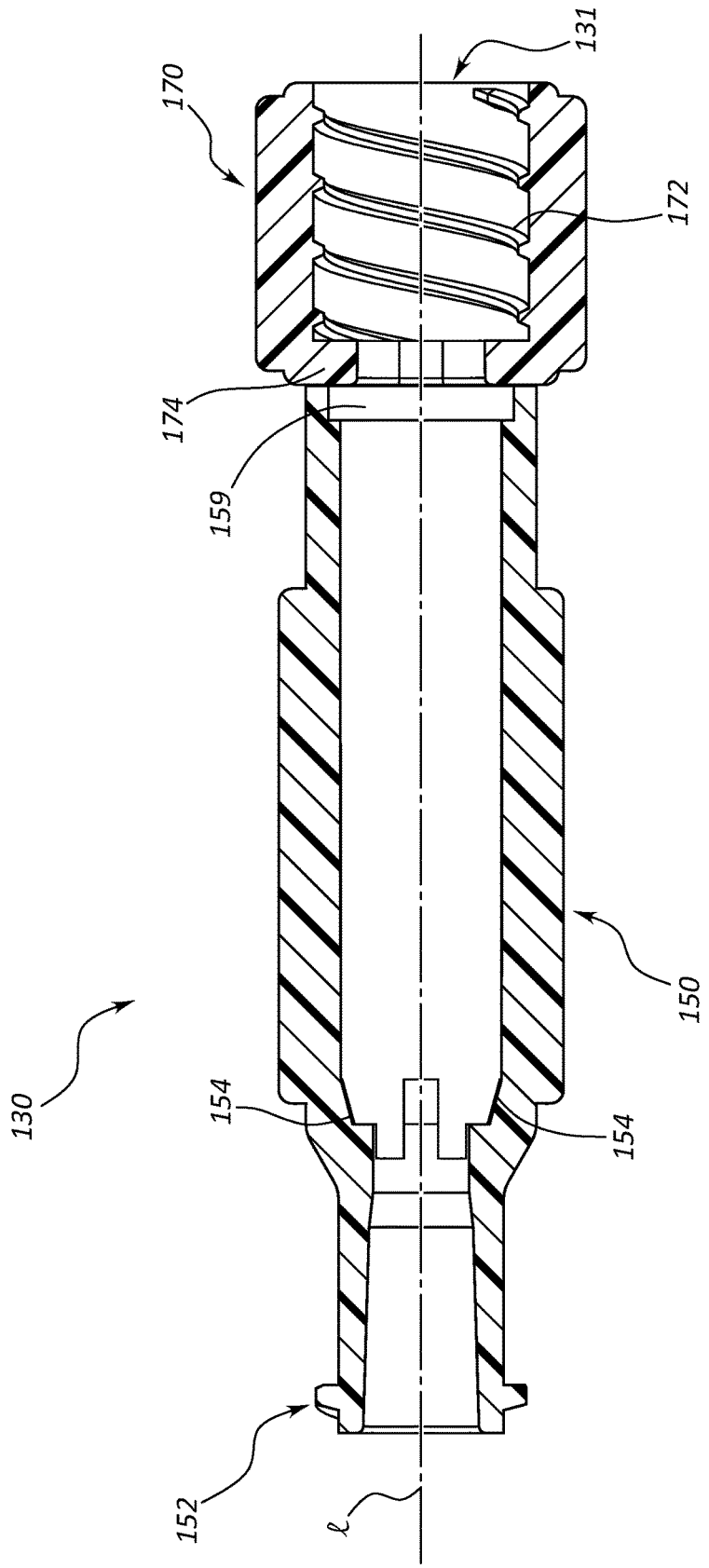
FIG. 6 is a cross-sectional view of the plug holder of FIGS. 2-5, with the plug cartridge and plug removed for clarity.
Figure 7:
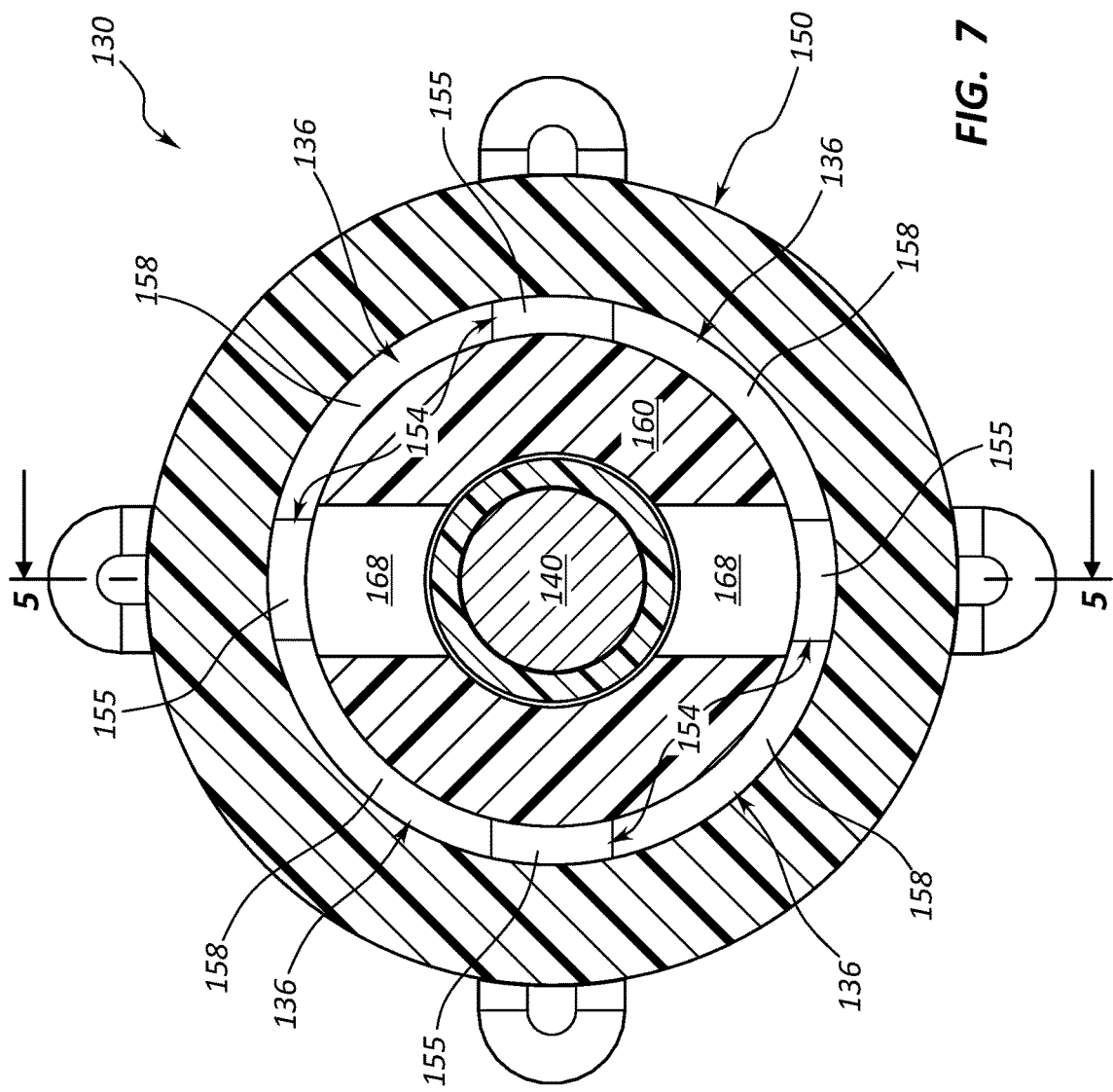
FIG. 7 is another cross-sectional view of the plug holder of FIGS. 2-6.
Figure 8:
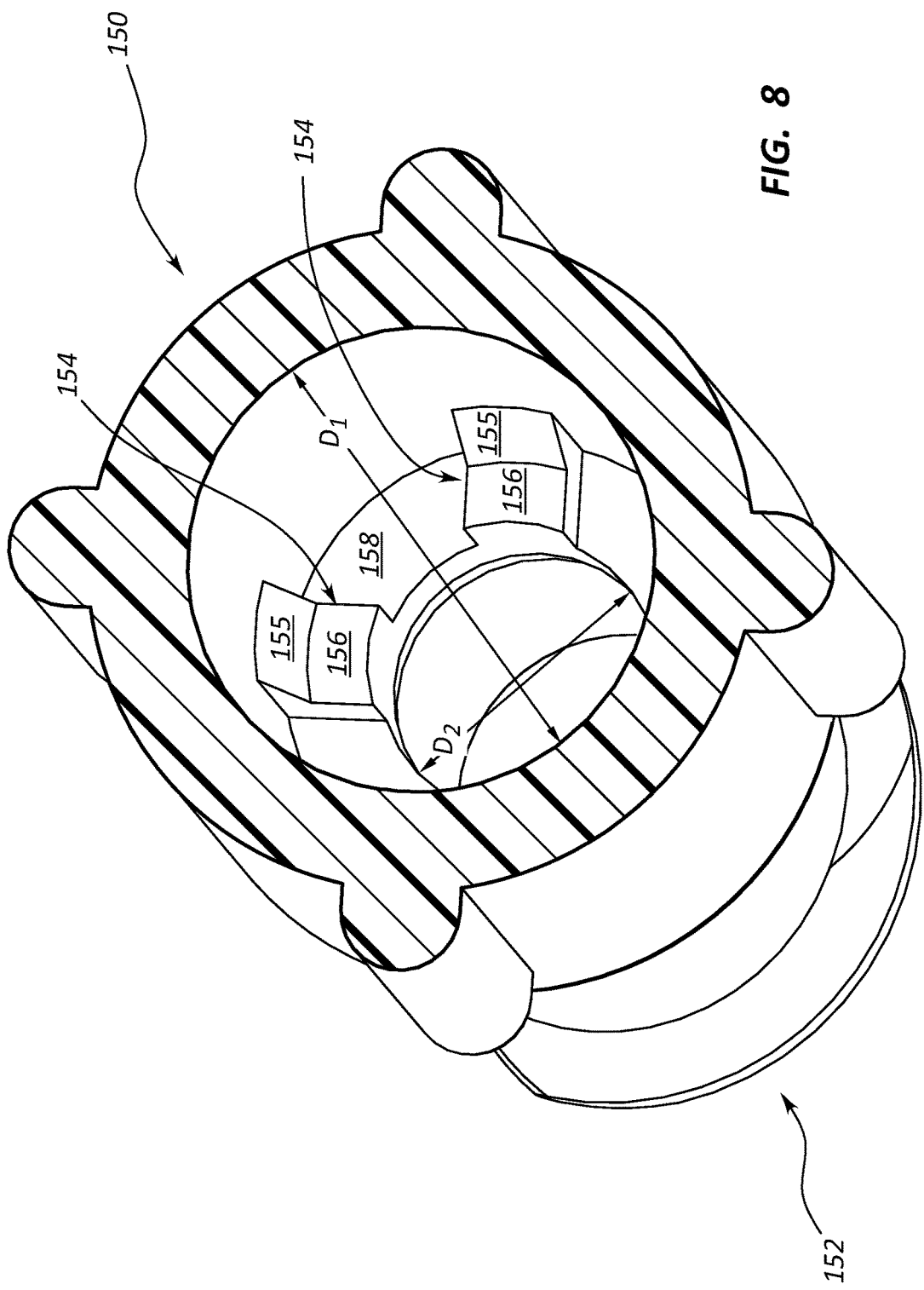
FIG. 8 is a cross-sectional perspective view of a portion of the plug holder of FIGS. 2-8, with the plug cartridge and the plug removed for clarity.

The plug holder 130 may be configured to couple to the distal end 124 of the syringe body 120. The plug holder 130 is shown in further detail in FIGS. 2-8. More particularly, FIG. 2 provides a side view of the plug holder 130. FIG. 3 provides a perspective view of the plug holder 130. FIG. 4 provides an exploded perspective view of the plug holder 130. FIGS. 5 and 6 are cross-sectional side views of the plug holder 130. FIGS. 5 and 6 are taken through a plane at the position of plane 5-5 of FIG. 7. FIG. 7 is a cross-sectional view of the plug holder 130 taken through a plane in the position shown by plane 7-7 of FIG. 5. And FIG. 8 is a cross-sectional perspective view of a portion of the plug holder 130.

As shown in FIGS. 2-8, the plug holder 130 may include a proximal member 150, a plug cartridge 160, and a distal member 170. A primary lumen 131 may extend through the plug holder 130. While the proximal member 150, the plug cartridge 160, and the distal member 170 are depicted as separate components that are coupled to each other, one of ordinary skill in the art will recognize that two or more of these components may be combined into one integrally formed component. Portions of the proximal member 150, plug cartridge 160, and/or distal member 170 may comprise a housing to which other portions of the assembly may be coupled (or with which other portions of the assembly may be integrally formed). Again, in some embodiments this housing or the plug holder 130 may be formed as a single integral (or monolithic) component.

The proximal member 150 may include a proximal adaptor 152 that is configured to couple to the distal end 124 of the syringe body 120. For example, the proximal member 150 may include a female Luer connection that mates with a male Luer connection on the syringe body 120 to form a fluid-tight connection. The outlet or orifice at the distal end 124 of the syringe body 120 may thus be in fluid communication with the proximal end of the primary lumen 131.

Additionally, the proximal member 150 may be generally elongate in shape with a hollow interior that extends along the length of the proximal member 150. The hollow interior may be configured to accommodate at least a proximal portion of the plug cartridge 160. In some embodiments, the hollow interior of the proximal member 150 varies in diameter across its length. Stated differently, an interior diameter ($D_1$) of a distal portion of the proximal member 150 may be larger than an interior diameter ($D_2$) that is disposed proximal of the distal portion (see FIG. 5). A portion of the proximal member 150 having a relatively small inner diameter (e.g., $D_2$) may abut against a portion of the proximal member 150 having a relatively large inner diameter (e.g., $D_1$) to form a ledge 158 (see FIGS. 7 and 8).

As shown in FIGS. 5-8, the proximal member 150 may further include a plurality of protrusions 154 that extend both distally from the ledge 158 and radially inward from the nominal diameter (e.g., $D_1$) of a portion of the proximal member 150 that is disposed immediately distal of the ledge 158. For instance, in the depicted embodiment (as particularly shown in FIG. 8), the protrusions 154 include a ramped or sloped surface 155 and a seating surface 156 that is disposed distal of the ledge 158.

The proximal member 150 may also include an annular recess 159 (see FIG. 6) disposed adjacent the distal end of the proximal member 150. As discussed below, the annular recess 159 may be configured to receive a first annular ridge 164 of the plug cartridge 160.

The distal member 170 may be generally cylindrical in shape with a hollow interior. In the depicted embodiment, the distal member 170 includes a plurality of interior threads 172. The interior threads 172 may facilitate coupling of the plug holder 130 to an elongate tube for delivery of a plug 140 to a void within a patient. The distal member 170 may include an annular ring 174 that protrudes radially inward toward a longitudinal axis (/) of the plug holder 130 (see FIGS. 5-6). In some embodiments, the distal member 170 may be configured to rotate about the longitudinal axis (/) of the plug holder 130 independently from the proximal member 150 and/or the plug cartridge 160.

The plug cartridge 160 may be generally elongate in shape with a hollow interior such that the primary lumen 131 extends longitudinally through the plug cartridge 160. In the depicted embodiment, the plug cartridge 160 includes a distal adaptor 162, the first annular ridge 164, a second annular ridge 166, one or more apertures 168 that are in fluid communication with the primary lumen 131, a frustoconical surface 161, and a shoulder 169.

The distal adaptor 162 may be configured to couple to a proximal end of an elongate tube, such as an introducer sheath or catheter to deliver fluid and/or a plug to a patient. For example, in the depicted embodiment, the distal adaptor 162 is a male Luer connection.

The first annular ridge 164 may be configured to be disposed within the annular recess 159 of the proximal member 150 and may be held in place by the annular ring 174 of the distal member 170. Stated differently, the annular ridge 164 may be disposed between the proximal member 150 and the distal member 170.

The second annular ridge 166 may extend radially outward from the plug cartridge 160. The second annular ridge 166 may couple the distal member 170 to the plug cartridge 160 and/or restrict distal displacement of the distal member 170 relative to the plug cartridge 160.

The plug cartridge 160 may generally be disposed between the proximal member 150 and the distal member 170. For example, a proximal end of the plug cartridge 160 may abut against the seating surfaces 156 of the protrusions 154. The ramped or sloped surface 155 may guide the proximal end of the plug cartridge 160 to the seating surface 156 as the plug holder 130 is assembled and may tend to retain the plug cartridge 160 in a radially centered position with respect to the proximal member 150.

The protrusions 154 may create separation between the plug cartridge 160 and both the inner diameter ($D_1$) of the proximal member 150 and the ledge 158. Stated differently, the protrusions 154 may contact the plug cartridge 160 to center the plug cartridge 160 within the proximal member 150 (via the sloped surfaces 155 of the protrusions 154) and thus form an annular space comprising one or more passageways or gaps 136 between the plug cartridge 160 and the remaining portion of the proximal member 150. The seating surfaces 156 of the protrusions 154 may provide a longitudinal offset between the proximal end of the plug cartridge 160 and the ledge 158, providing a flow path around the proximal end of the plug cartridge 160. Thus, the dimensions of the protrusions 154 may define a dimension of the one or more gaps 136. As described in further detail below, these gaps 136 may form one or more flow paths or pathways that permit the flow of fluid around a periphery of the plug holder 130.

The primary lumen 131 extending through the plug cartridge 160 may be configured to accommodate the plug 140. Thus, the primary lumen 131 may define a cavity configured to retain the plug 140. The cavity may be centrally disposed within the plug holder 130 and may be configured to orient the plug 140 within the plug holder 130 such that the longitudinal axis of the plug 140 is aligned with the longitudinal axis of the plug holder 130 or cavity. The plug 140 may be of any suitable composition, shape, and/or size. For example, in some embodiments, the plug 140 may include, comprise, or consist of a bioabsorbable material. In some embodiments, the bioabsorbable material (or a portion thereof) is derived from animal tissue, such as pig skin or cow skin. In some embodiments, the bioabsorbable material is a collagen-containing material, such as a gelatin foam from an animal source. In other or further embodiments, the bioabsorbable material (or a portion thereof) is a synthetic polymer, such as polylactic acid, polyglycolide, or poly (lactic-co-glycolic acid). In some embodiments, the plug 140 includes or consists of a non-bioabsorbable material, such as polyvinyl alcohol or polyvinyl acetate. In some embodiments, the plug 140 includes a dye. The dye may facilitate visualization of the plug 140 when the plug 140 is disposed within the plug holder 130. In some embodiments, the plug 140 may change colors when contacted with fluid (e.g., water or saline), thereby allowing a practitioner to visually determine when the plug 140 has been wetted.

The plug 140 may be generally elongate in shape. For example, in some embodiments, the plug 140 is an elongate piece of material that has been rolled into a substantially cylindrical shape of between 1 mm and 5 mm (e.g., approximately 2 mm) in diameter. The plug 140 may have a length that is at least 2-fold, at least 5-fold, and/or at least 10-fold longer than the diameter of the plug 140. In some embodiments, the plug 140 is between 10 mm and 30 mm (e.g., approximately 20 mm) in length.

As noted above, the plug cartridge 160 may further include one or more apertures 168. For example, in the depicted embodiment, two apertures 168 each extend radially outward through a sidewall of the plug cartridge 160. Accordingly, the one or more gaps 136 between the proximal member 150 and the plug cartridge 160 are in fluid communication with the main lumen 131 via the apertures 168. As described in further detail below, the apertures 168 may allow fluid (e.g., water or saline) to flow radially outward from the lumen 131 toward the one or more gaps 136 between the proximal member 150 and the plug cartridge 160 (see FIG. 5).

In some embodiments, the plug cartridge 160 includes a frustoconical surface 161 adjacent its proximal end. The frustoconical surface 161 may direct (e.g., funnel) fluid flow into the central lumen 131 as the plug 140 is deployed as described below.

The plug cartridge 160 may also include the shoulder 169 that is configured to restrict proximal displacement of the plug 140 during operation of the medical device 100. In the depicted embodiment, the shoulder 169 is an annular protrusion that extends inward toward a longitudinal axis (/) of the plug holder 130. The shoulder 169 may define a proximal portion of the lumen 131 that is relatively narrow in comparison to a distal portion of the lumen 131. In other words, a proximal portion of the lumen 131 that is defined by the shoulder 169 may have a smaller diameter than a distal portion of the lumen 131.

In some embodiments, the plug holder 130 (or a portion thereof) is substantially transparent, thereby allowing the practitioner to visualize wetting and ejection of the plug 140 as described below. In other embodiments, the plug holder 130 is opaque.

The medical device 100 may be used to deliver the plug 140 to a patient. For example, in some embodiments, a practitioner may obtain a medical device 100 that includes a plunger 110, a syringe body 120, and a plug holder 130 that is coupled to the distal end 124 of the syringe body 120. The plug holder 130 may have the plug 140 disposed within a lumen 131 that extends longitudinally along a length of the plug holder 130.

In some instances, the plunger 110 may initially be disposed such that the plunger 110 is fully advanced within the syringe body 120. Liquid, such as water or saline, may then be drawn into the medical device 100 to wet the plug 140 and introduce fluid into the reservoir 126 within the syringe body 120. For example, the plunger 110 may be retracted within the syringe body 120 while the distal end of the plug holder 130 is disposed within the liquid. As the plunger 110 is retracted in this manner, fluid may be drawn into the reservoir 126 of the syringe body 120 via two different pathways.

First, as the plunger 110 is retracted, fluid may be drawn into the lumen 131, pass through (and thereby wet) the plug 140, and exit the proximal end of the plug holder 130 to thereby enter the reservoir 126 of the syringe body 120. The shoulder 169 of the plug holder 130 may prevent proximal displacement of the plug 140 past the shoulder 169, thereby ensuring that the plug 140 is not inadvertently sucked into the reservoir 126 of the syringe body 120. Wetting of the plug 140 may increase the lubricity of the plug 140, thereby facilitating both ejection of the plug 140 from the plug holder 130 and advancement of the plug 140 through a lumen of an elongate tube to an interior portion (e.g., a void) of a patient. In some embodiments, the plug 140 may also swell as its wets, and may thus partially occlude or disrupt fluid flow through the lumen 131.

Second, instead of passing through the plug 140, fluid may be drawn into a distal portion of the lumen 131, pass through the one or more apertures 168 of the plug cartridge 160 into one or more gaps 136 disposed around a periphery of the plug cartridge 160, and then travel proximally through the one or more gaps 136 past the proximal end of the plug holder 130 to enter into the reservoir 126 of the syringe body 120. The relative spacing of the plug cartridge 160 and the proximal member 150, provided by the protrusions 154, may define a portion of this flow path, first along an annular space between an outside surface of the plug cartridge 160 and an inside surface of the proximal member 150 (due to the centering of the plug cartridge 160 by the interaction with the sloped surfaces 155), then between a proximal end of the plug cartridge 160 and the ledge 158 of the proximal member 150 (due to the offset provided by the seating surfaces 156). The apertures 168 and this flow path (comprising the annular space and the offset described above) may provide a second flow path between the distal end of the lumen 131 and the proximal end of the lumen 131.

The two pathways described above may both operate to fill the reservoir 126 of the syringe body 120. For example, as the plunger 110 is initially retracted, fluid may, at least initially, primarily follow the first pathway (i.e., through the plug 140). As fluid passes through the plug 140, the plug 140 may be wetted. Again, such wetting may obstruct further fluid flow through the plug 140. In some embodiments, the plug 140 may begin to swell as it is wetted, further contributing to obstruction of fluid flow through the plug 140. As the flow rate of fluid through the plug 140 decreases, a greater proportion (e.g., a majority) of the fluid may instead pass through the second pathway (i.e., through the apertures 168 and the one or more gaps 136) to enter into the reservoir 126 of the syringe body 120.

Relative flow rates between the two pathways may depend, at least partially, on the relative sizes of the cross-sectional surface areas presented by the lumen 131 and the gaps 136. For example, in some embodiments, the cross-sectional surface area of the lumen 131 (where the cross-section is perpendicular to the longitudinal axis (/) of the plug holder 130) is greater than the cross-sectional surface area of the one or more gaps 136. Thus, a relatively large fluidic force may be applied to the plug 140 (both during retraction and advancement of the plunger 110) due to its positioning within a lumen having a relatively large cross-sectional surface area in comparison to the cross-sectional surface area of the gaps 136.

If desired, any air bubbles that were introduced into the medical device 100 as the plunger 110 was retracted may be removed in the traditional manner (i.e., by orienting the medical device 100 such that the distal end of the medical device 100 is pointed upward, tapping the medical device 100, and ejecting air bubbles by advancing the plunger 110 toward the distal end of the medical device 100.

Once both the plug 140 has been wetted and a sufficient quantity of fluid has entered into the reservoir 126 of the syringe body 120, the practitioner may couple the distal end of the plug holder 130 to an elongate tube, such as an introducer sheath or catheter. The introducer sheath or catheter may be in fluid communication with a void into which the plug 140 is to be inserted. For example, the distal end 124 of the syringe body 120 may be coupled to a proximal end of an introducer sheath used in a biopsy procedure as described above.

The practitioner may then advance the plunger 110 toward the distal end 124 of the syringe body 120, thereby distally displacing fluid in the reservoir 126. As the fluid is displaced in a distal direction, the fluid may encounter the frustoconical surface 161 of the plug cartridge 160. The frustoconical surface 161 may direct (e.g., funnel) fluid flow into the central lumen 131. Such fluid may exert a distal force on the plug 140 disposed within the central lumen 131, thereby causing distal displacement and ejection of the plug 140 from the plug holder 130 into the elongate tube that is in fluid communication with the void. As the plunger 110 is advanced, the displaced fluid may push the plug 140 through the elongate tube and into the desired void. The inserted plug 140 may serve any suitable purpose, such as obstructing fluid flow, inducing blood coagulation, and/or providing a scaffold to promote tissue growth.

Alternatively, instead of retracting the plunger 110 to draw fluid into the reservoir 126 of the syringe body 120 as described above, the syringe body 120 may be pre-filled with liquid. The distal end 124 of the pre-filled syringe body 120 may then be attached to the proximal end of the plug holder 130. Once the syringe body 120 is attached to the proximal end of the plug holder 130, the plunger 110 may be advanced. Advancement of the plunger 110 in this manner may both wet the plug 140 and discharge the plug 140 from the plug holder 130 into an elongate tube for delivery to a void as described above. In other words, the plug 140 may be hydrated as it is ejected from the plug holder 130.

Figure 9:
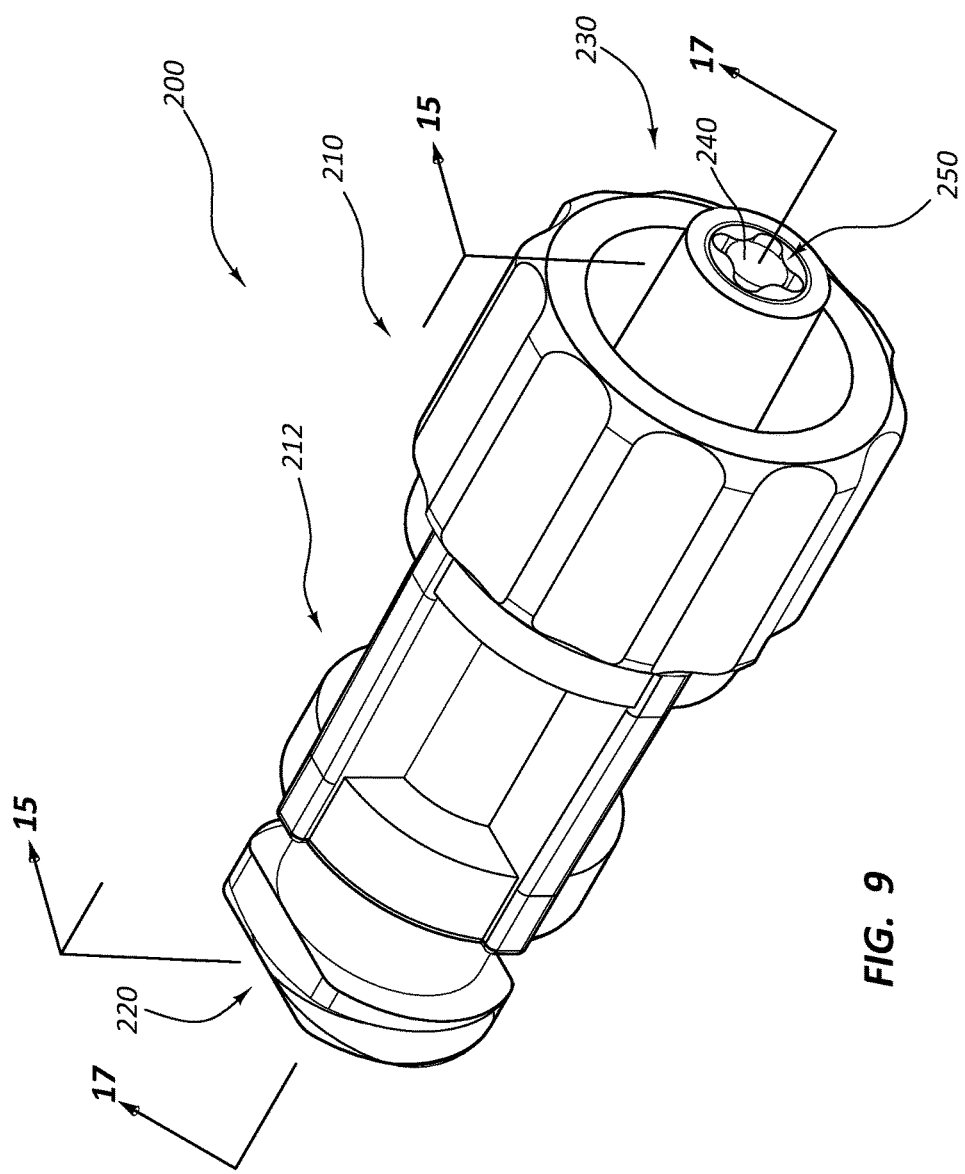
FIG. 9 is a perspective view of a medical plug delivery device according to another embodiment.
Figure 10:
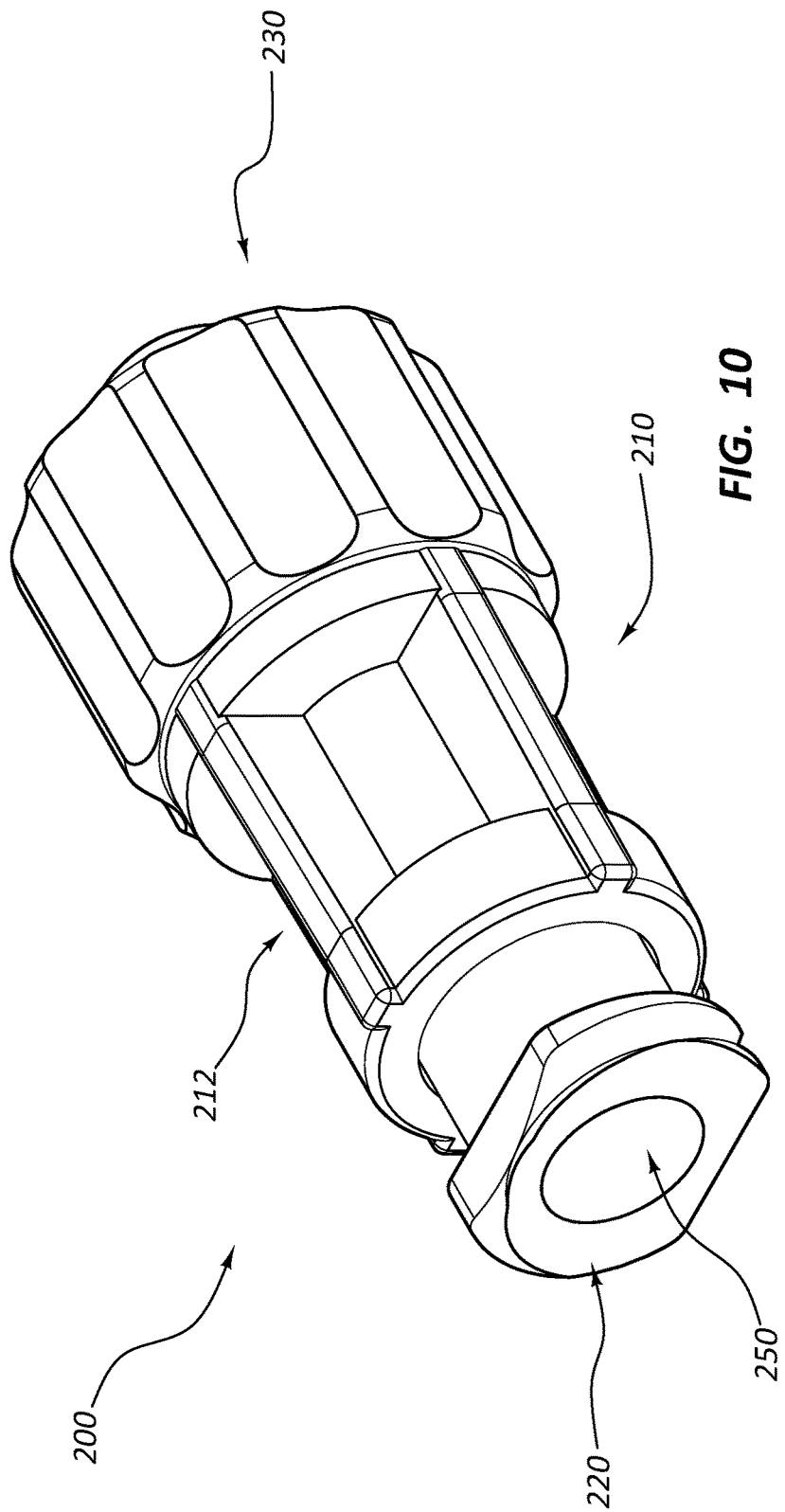
FIG. 10 is another perspective view of the medical plug delivery device of FIG. 9.
Figure 11:
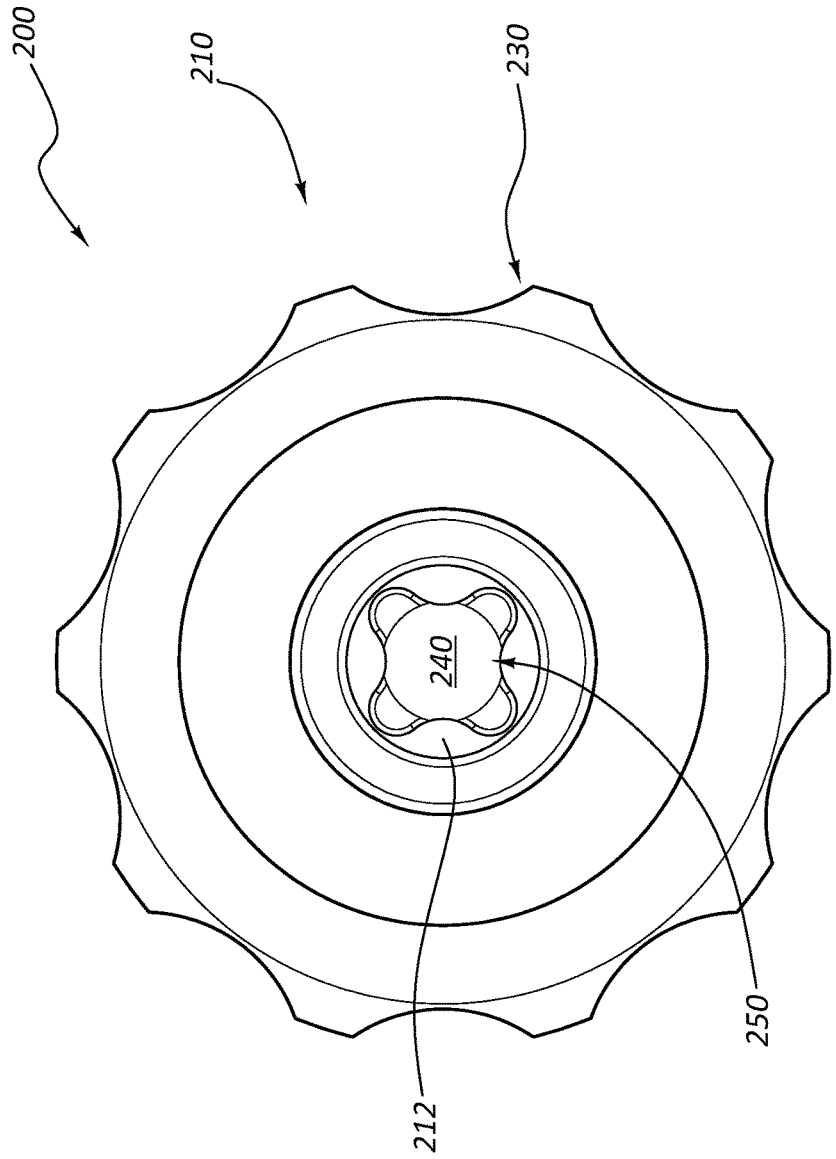
FIG. 11 is a view of the distal end of the medical plug delivery device of FIG. 9.
Figure 12:
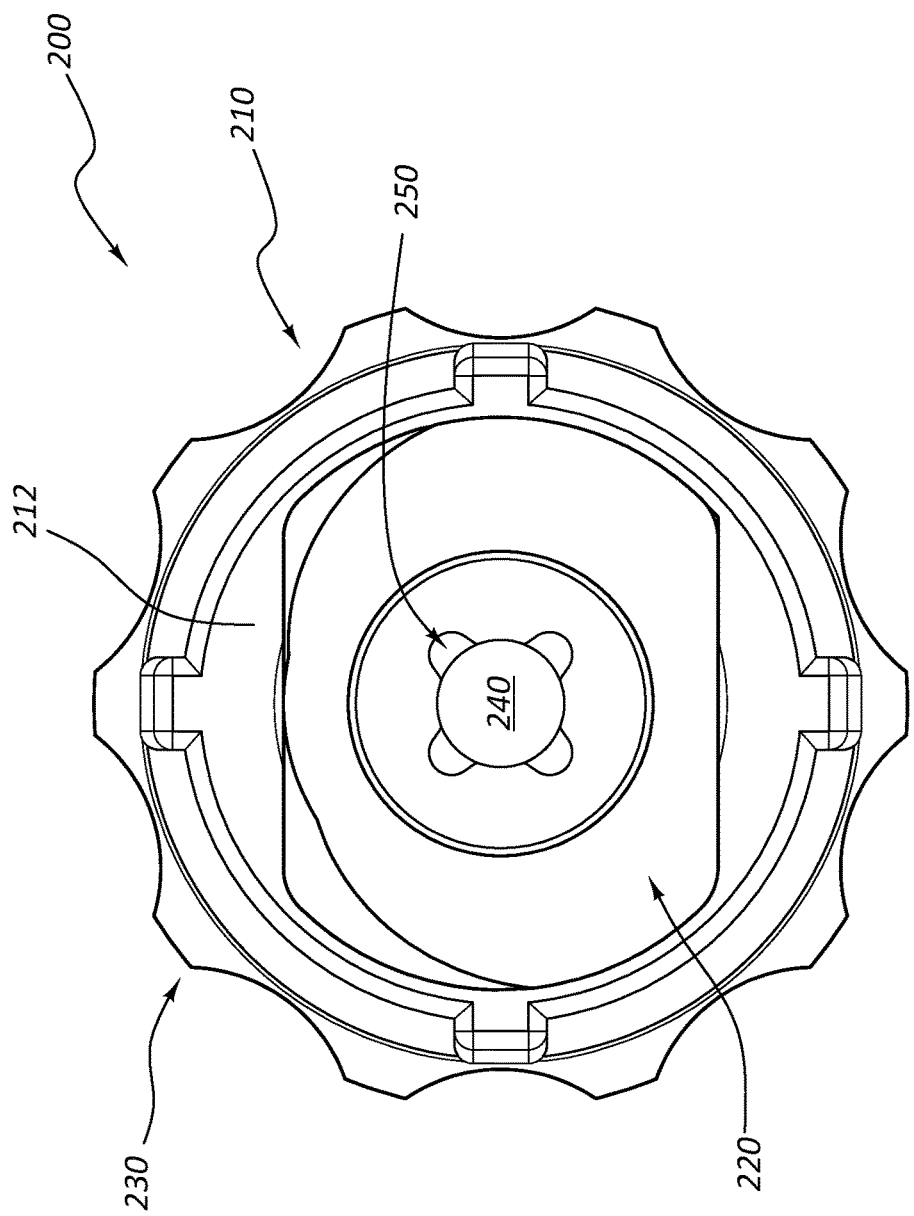
FIG. 12 is a view of the proximal end of the medical plug delivery device of FIG. 9.
Figure 13:
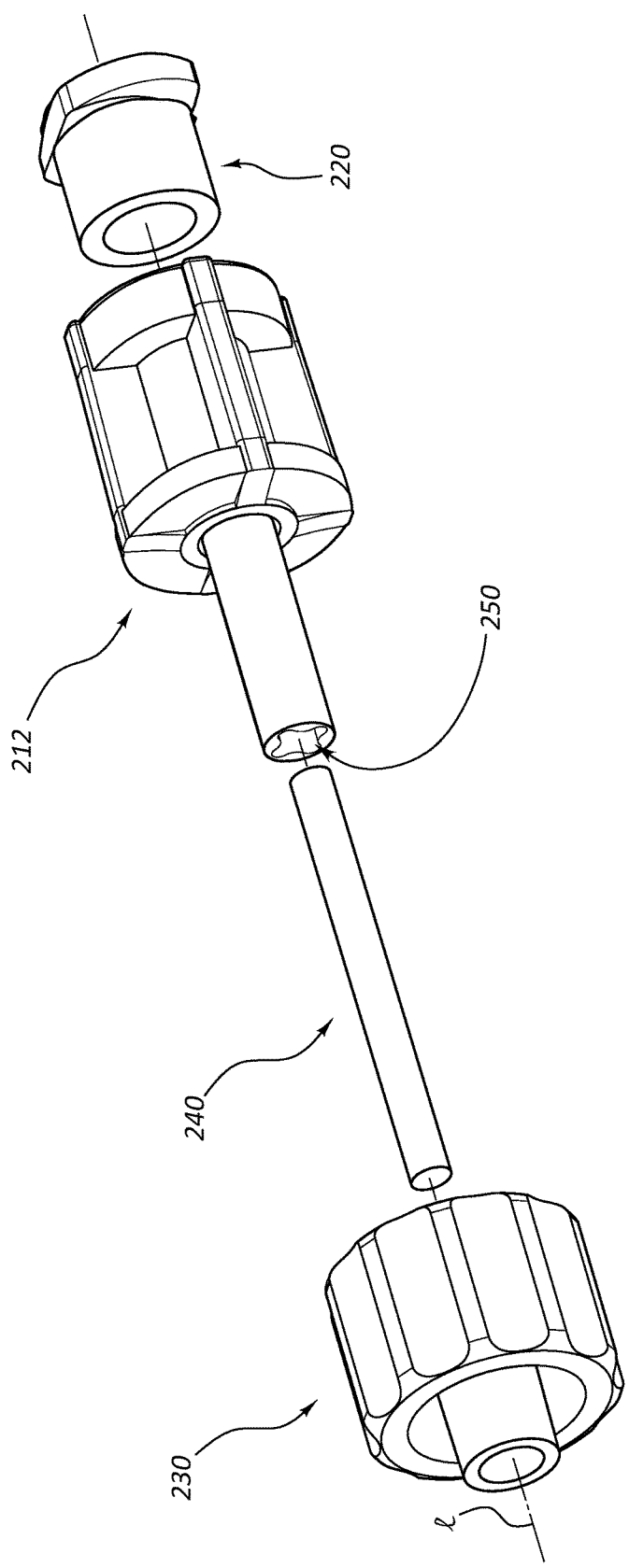
FIG. 13 is an exploded perspective view of the medical plug delivery device of FIG. 9.
Figure 14:
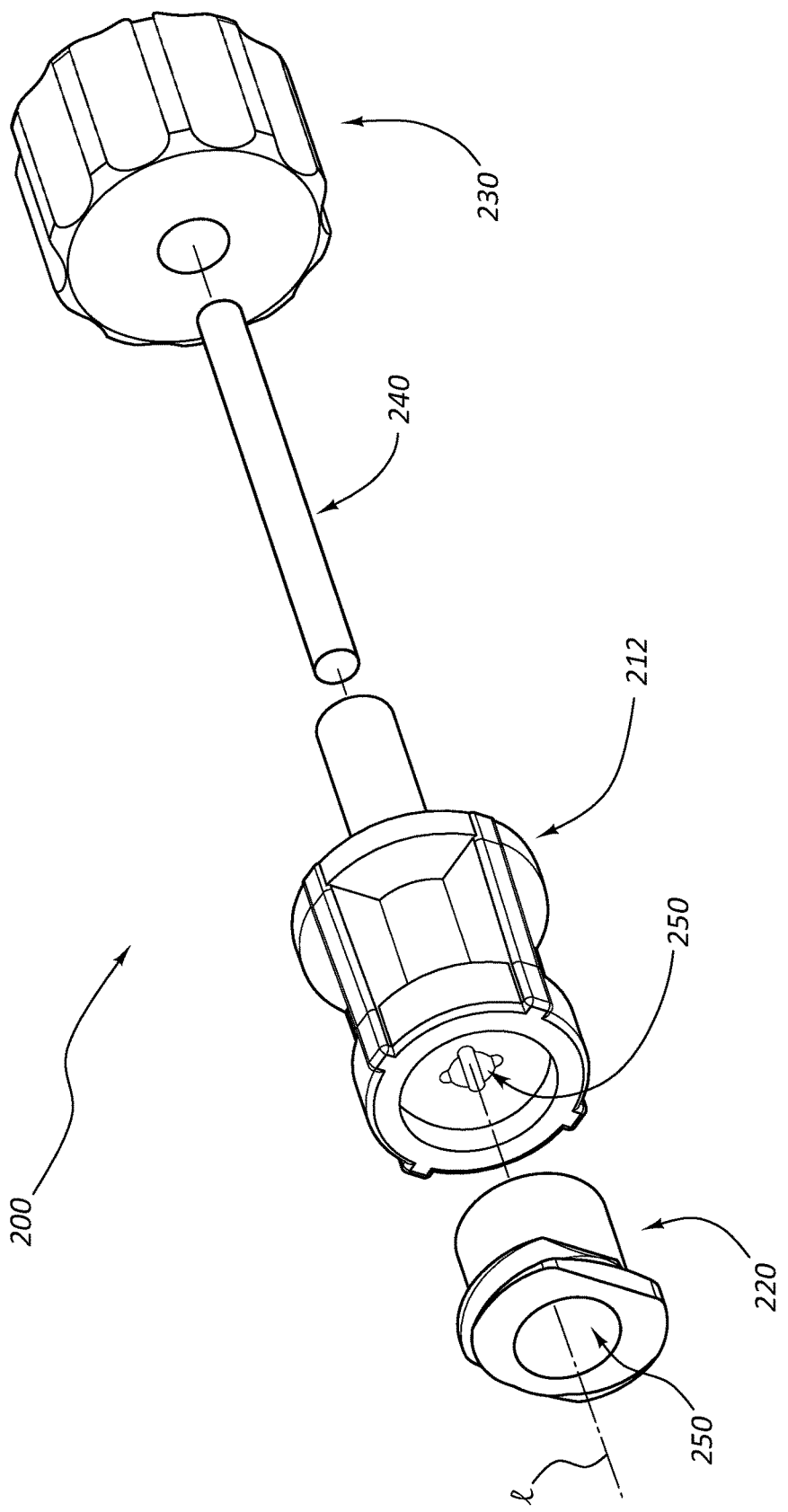
FIG. 14 is another exploded perspective view of the medical plug delivery device of FIG. 9.

FIGS. 9-18 provide alternative views of a medical plug delivery device 200. More particularly, FIGS. 9 and 10 provide alternative perspective views of the medical plug delivery device 200. FIGS. 11 and 12 provide views of the medical plug delivery device 200 showing the distal (FIG. 11) and proximal (FIG. 12) ends. FIGS. 13 and 14 are alternative exploded perspective views of the medical plug delivery device 200. FIGS. 15-19 are various cross-sectional views of the medical plug delivery device 200.

The medical plug delivery device 200 is, in some respects, analogous to the plug holder 130 described above. For example, the medical plug delivery device 200 may be coupled to a fluid delivery device, such as the syringe formed from the syringe body 120 and the plunger 110 depicted in FIG. 1, to deliver a medical plug 240 to a void within a patient. Relevant disclosure set forth above in connection with the medical device 100 may apply equally to features of the medical plug delivery device 200 and related components (and vice versa).

As shown in FIGS. 9-18, the medical plug delivery device 200 may include a proximal connector 220, a distal connector 230, and a central member 212. In some embodiments, a combination of one or more of the proximal connector 220, the distal connector 230, and the central member 212 may form a housing 210 that defines a channel 250. For example, in the depicted embodiment, the channel 250 is defined by the central member 212 and the proximal connector 220. In some embodiments, the housing 210 (or a portion thereof) is substantially transparent, thereby allowing a practitioner to visualize wetting and ejection of the medical plug 240 as described below. In other embodiments, the housing 210 is opaque.

In some embodiments, such as the embodiment shown in FIGS. 9-18, the distal connector 230, the central member 212, and the proximal connector 220 are separate components. For example, in some embodiments, the distal connector 230 and the proximal connector 220 are separate components that are coupled to each other (e.g., via an adhesive). In other words, the distal connector 230 and the proximal connector 220 may be manufactured separately and then coupled together. In other embodiments, the distal connector 230, the central member 212, and the proximal connector 220 are integrated in a single monolithic piece that forms the housing 210.

The distal connector 230 may be configured to connect to a distal medical appliance, such as an introducer, a catheter, or other elongate tube. For example, in the depicted embodiment, the distal connector 230 is a male Luer connector. In some embodiments, the distal medical appliance is in fluid communication with an interior of the patient. For example, a distal end of the distal medical appliance may be positioned adjacent a void within a patient to facilitate delivery of the medical plug 240 to a patient as described in greater detail below.

The proximal connector 220 may be configured to connect to a proximal fluid delivery device (e.g., a syringe). For example, the proximal connector 220 may be a female Luer connector that is configured to couple to a distal end of a syringe body in a manner analogous to that described above in connection with the proximal adaptor 152 and the distal end 124 of the syringe body 120.

The channel 250 defined by the housing 210 may extend across the housing 210 from a proximal end of the medical plug delivery device 200 to a distal end of the medical plug delivery device 200. The channel 250 may be configured to receive the medical plug 240. In some embodiments, the channel 250 is configured to maintain the medical plug 240 in an orientation that aligns a longitudinal axis of the medical plug 240 with the longitudinal axis (/) of the housing 210 during deployment of the medical plug 240. In some embodiments, the channel 250 is non-circular in shape.

Figure 19:
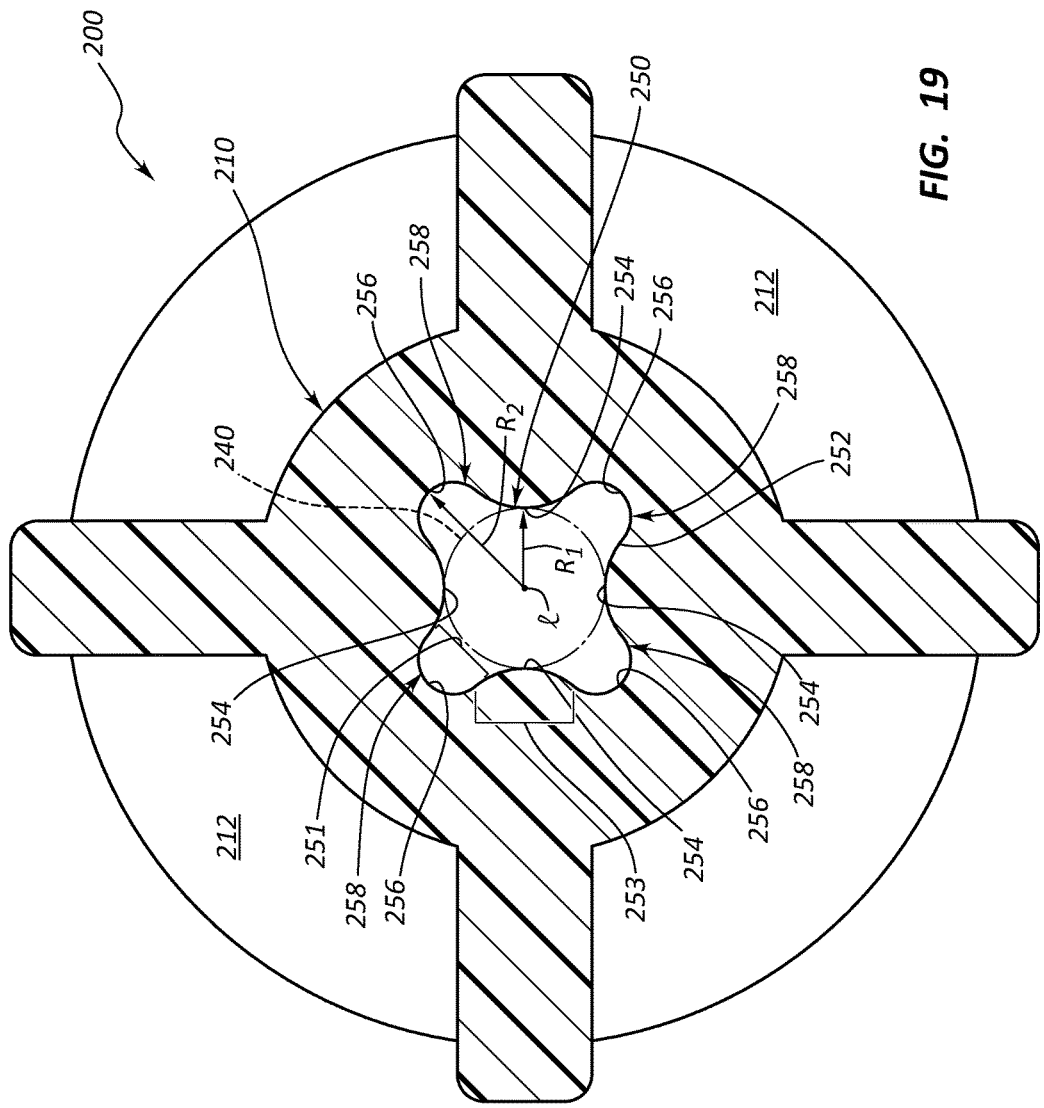
FIG. 19 is a cross-sectional view of the medical plug delivery device of FIG. 9 through plane 19-19 of FIG. 15.

A cross-section of an exemplary channel 250 is shown in FIG. 19. More specifically, FIG. 19 provides a cross-sectional view of the housing 210 of the medical plug delivery device 200 through line 19-19 of FIG. 15. This cross-section is perpendicular to the longitudinal axis (/) of the housing 210. As shown in FIG. 19, the housing 210 defines a perimeter 252 of a portion of the channel 250.

The perimeter 252 of the channel 250 may include (1) a plurality of inward-most points 254 at a first radius ($R_1$) from the longitudinal axis (/) of the housing 210 and (2) a plurality of outward-most points 256 at a second radius ($R_2$) from the longitudinal axis (/) of the housing 210, wherein the second radius ($R_2$) is longer than the first radius ($R_1$). In some embodiments, $R_1$ is between approximately 0.025 inches and 0.045 inches, such as between 0.030 inches and 0.035 inches, while $R_2$ is between approximately 0.035 inches and 0.075 inches, such as between 0.040 and 0.060 inches. In some embodiments, the difference between the lengths of $R_1$ and $R_2$ is between 0.030 inches and 0.050 inches. In the depicted embodiment, each point of the plurality of inward-most points 254 is separated from an adjacent inward-most point 254 by an outward-most point 256. Stated differently, each inward-most point 254 may be disposed between two outward-most points 256. In the depicted embodiment, the perimeter 252 of the channel 250 includes exactly four inward-most points 254 and exactly four outward-most points 256.

In some embodiments, the perimeter 252 of the channel 250 is curvilinear in shape. For example, in the depicted embodiment, the perimeter 252 of the channel 250 is formed from regions of alternating concavity. Stated differently, in some embodiments the perimeter 252 may include a plurality of concave regions that are separated from one another by intervening convex regions. (Concavity is determined from the perspective of the longitudinal axis (/) of the housing 210.) In some embodiments, each inward-most point 254 is disposed on the apex of a convex region 253, while each outward-most point 256 is disposed on an apex of a concave region 251. In some embodiments, a cross-section of the channel 250 (e.g., as shown in FIG. 19) may be envisioned as including a central circular region (defined by a circle that contacts each of the plurality of inward-most points 254) and a plurality of lobes 258 that extend therefrom to the plurality of outward-most points 256.

The medical plug 240 may be disposed within the channel 250. The medical plug 240 may be of any suitable composition, shape, and/or size. For example, in some embodiments, the medical plug 240 may comprise or consist of a bioabsorbable material. In some embodiments, the bioabsorbable material (or a portion thereof) is derived from animal tissue, such as pig skin or cow skin. In some embodiments, the bioabsorbable material is a collagen-containing material, such as a gelatin foam from an animal source. In other or further embodiments, the bioabsorbable material (or a portion thereof) is a synthetic polymer, such as polylactic acid, polyglycolide, or poly(lactic-co-glycolic acid). In some embodiments, the medical plug 240 includes or consists of a non-bioabsorbable material, such as polyvinyl alcohol or polyvinyl acetate. In some embodiments, the medical plug 240 includes a dye. The dye may facilitate visualization of the medical plug 240 when the medical plug 240 is disposed within the channel 250 of the housing 210. In some embodiments, the medical plug 240 may change colors when contacted with fluid (e.g., water or saline), thereby allowing a practitioner to visually determine when the medical plug 240 has been wetted.

The medical plug 240 may be generally elongate in shape. For example, in some embodiments, the medical plug 240 is an elongate piece of material that has been compacted, crushed, and/or rolled into a substantially cylindrical shape of between 1 mm and 5 mm (e.g., between 1.5 and 2.5 mm in diameter) in diameter. For example, in some embodiments, an elongate medical plug 240 having a height and width of 5 mm×5 mm may be compacted, crushed, and/or rolled from a square prism shape into a medical plug 240 that is substantially cylindrical in shape. For example, a medical plug having a height and width of 5 mm×5 mm may be compacted to a cylindrical shape having a diameter of between 1.5 and 2.5 mm. The medical plug 240 may have a length that is at least 2-fold, at least 5-fold, and/or at least 10-fold longer than the diameter of the medical plug 240. In some embodiments, the medical plug 240 is between 10 mm and 30 mm (e.g., approximately 20 mm) in length, although longer or shorted medical plugs 240 may be used as well.

When disposed within the channel 250 in a dry state, the medical plug 240 may contact the plurality of inward-most points on the perimeter of the channel 250. Stated differently, the medical plug 240 may be frictionally engaged by the plurality of inward-most points 254. In this same state (i.e., while the medical plug 240 is still dry), the medical plug 240 is not in contact with the plurality of outward-most points 256. Rather, a plurality of elongate passageways extend along the medical plug 240 due to the gaps between the medical plug 240 and the outward-most points 256. These elongate passageways may be disposed within the outward-extending lobes 258 of the channel 250.

In some embodiments, the medical plug 240 is sized to—when dry, compacted, and unconstrained—have a diameter that is the same as the diameter formed by the plurality of inward-most points 254 of the perimeter 252. In other embodiments, the medical plug 240 is sized to—when dry, compacted, and unconstrained—have a diameter that is somewhat longer than the diameter formed by the plurality of inward-most points 254 of the perimeter 252. For example, the medical plug 240 may have a diameter that is between 0.001 and 0.010 inches (e.g., between 0.003 and 0.005 inches) larger than the diameter formed by the inward-most points 254. Thus, when the medical plug 240 is disposed within the channel 250, the inward-most points 254 on the perimeter 252 of the channel 250 constrain the medical plug 240, causing compaction of the medical plug 240 to a shape that differs somewhat from its unconstrained shape. Notwithstanding such compaction, when the medical plug 240 is disposed within the channel 250 in a dry state, the medical plug 240 does not contact the plurality of outward-most points 256. Stated differently, when the medical plug 240 is disposed within the channel 250 in a dry state, a plurality of passageways may extend around the medical plug 240.

Figure 15:
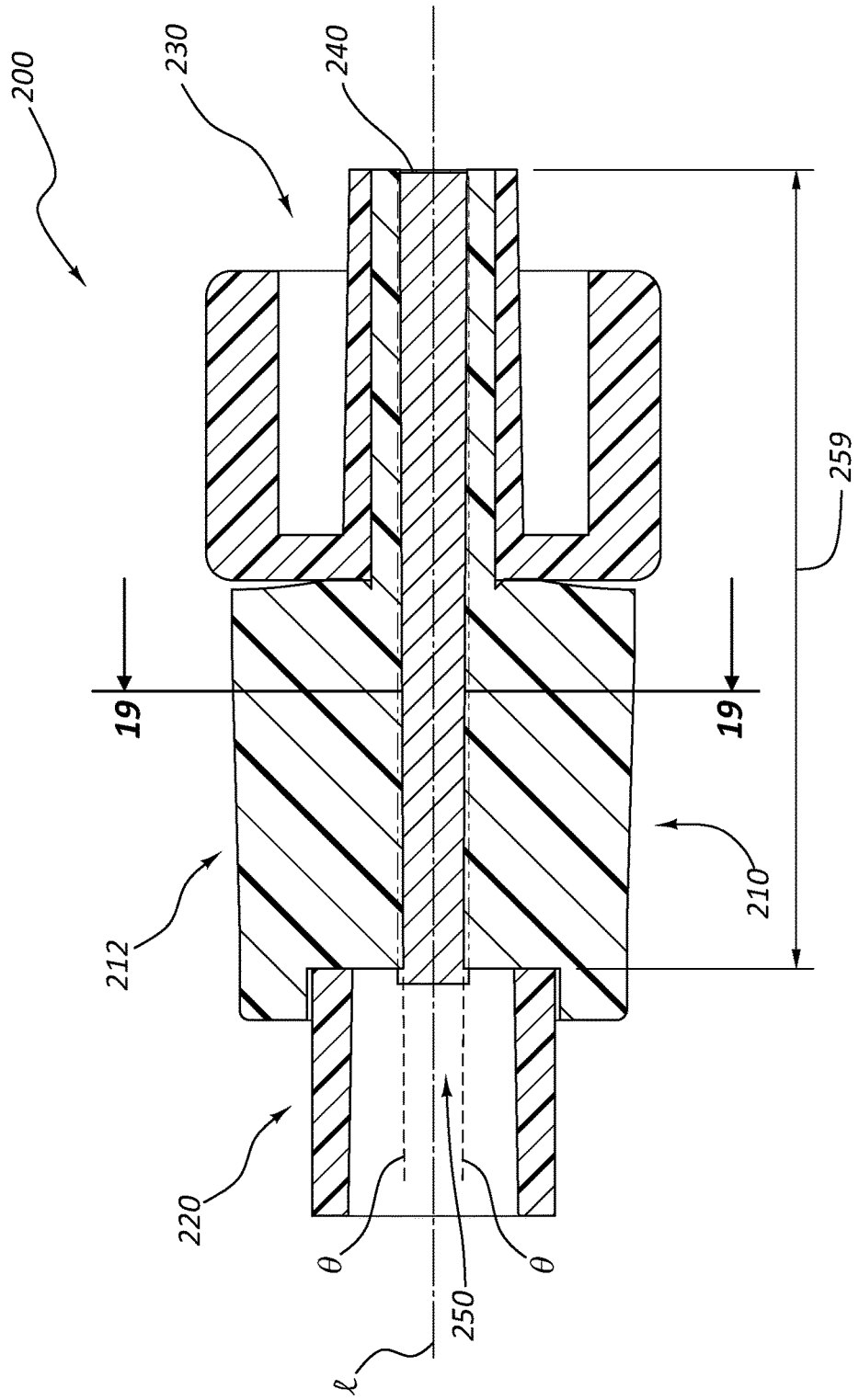
FIG. 15 is a cross-sectional side view of the medical plug delivery device of FIG. 9 through plane 15-15 of FIG. 9.
Figure 16:
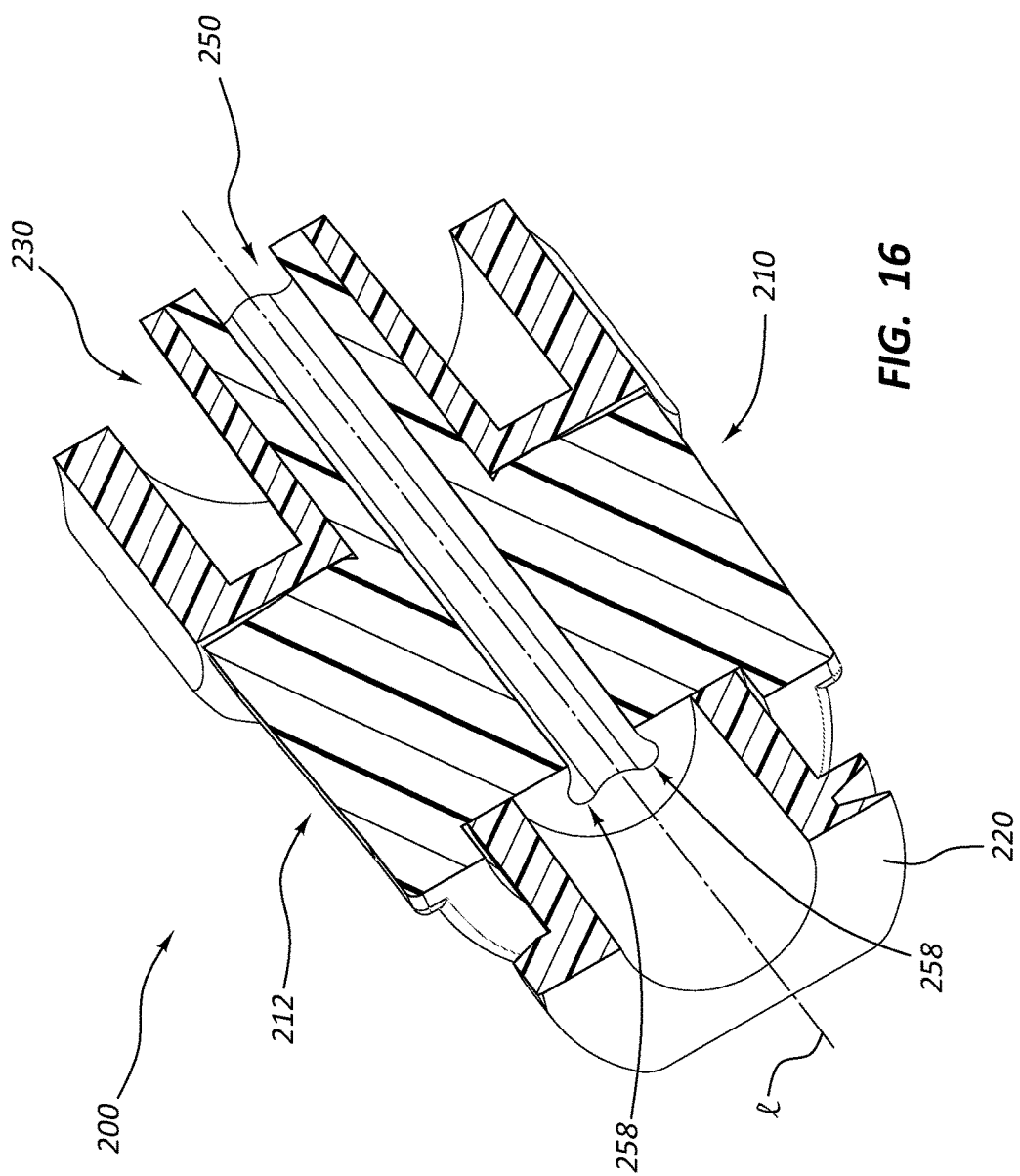
FIG. 16 is a cross-sectional perspective view of the medical plug delivery device of FIG. 9 cut through plane 15-15 of FIG. 9.
Figure 17:
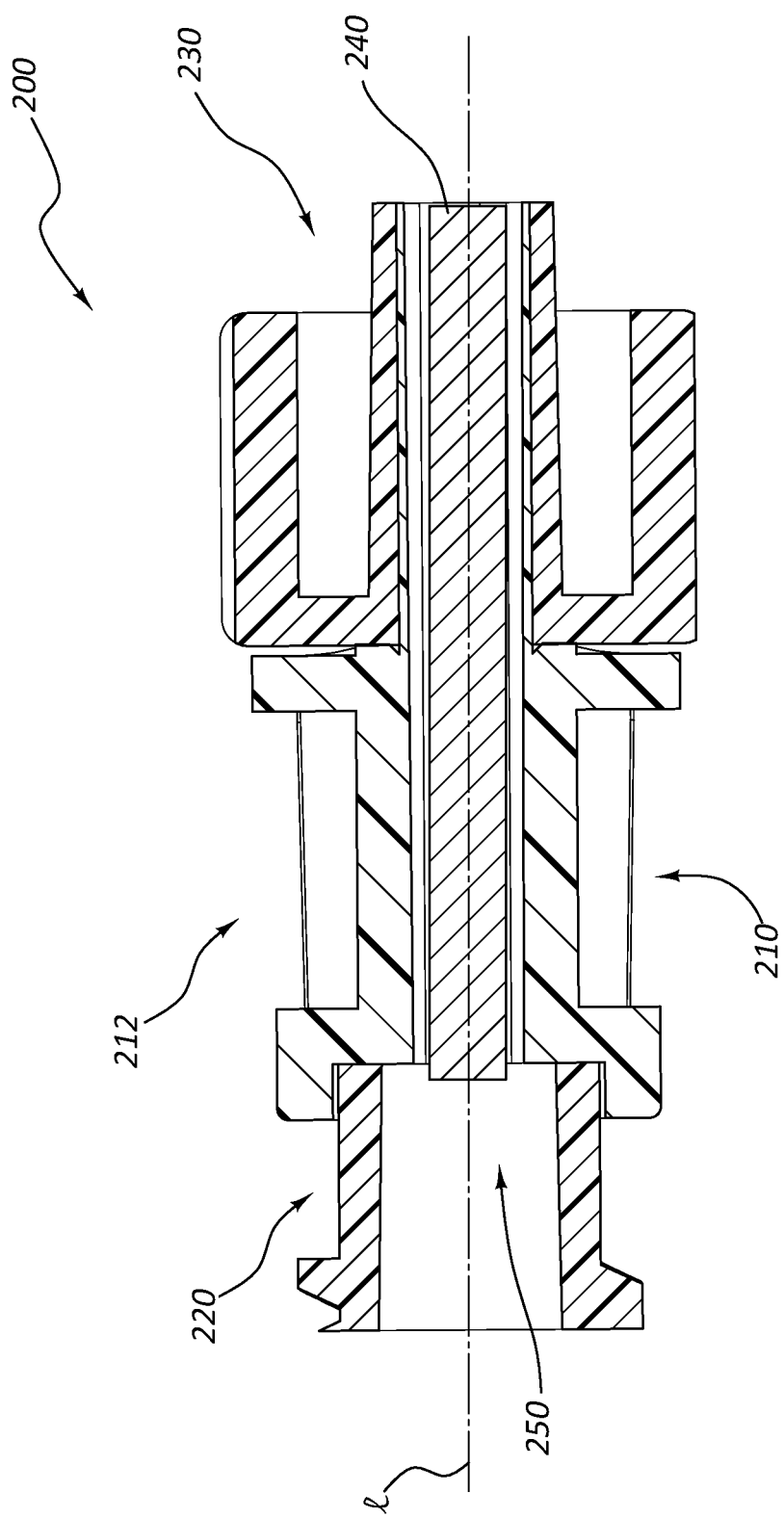
FIG. 17 is a cross-sectional side view of the medical plug delivery device of FIG. 9 through plane 17-17 of FIG. 9.
Figure 18:
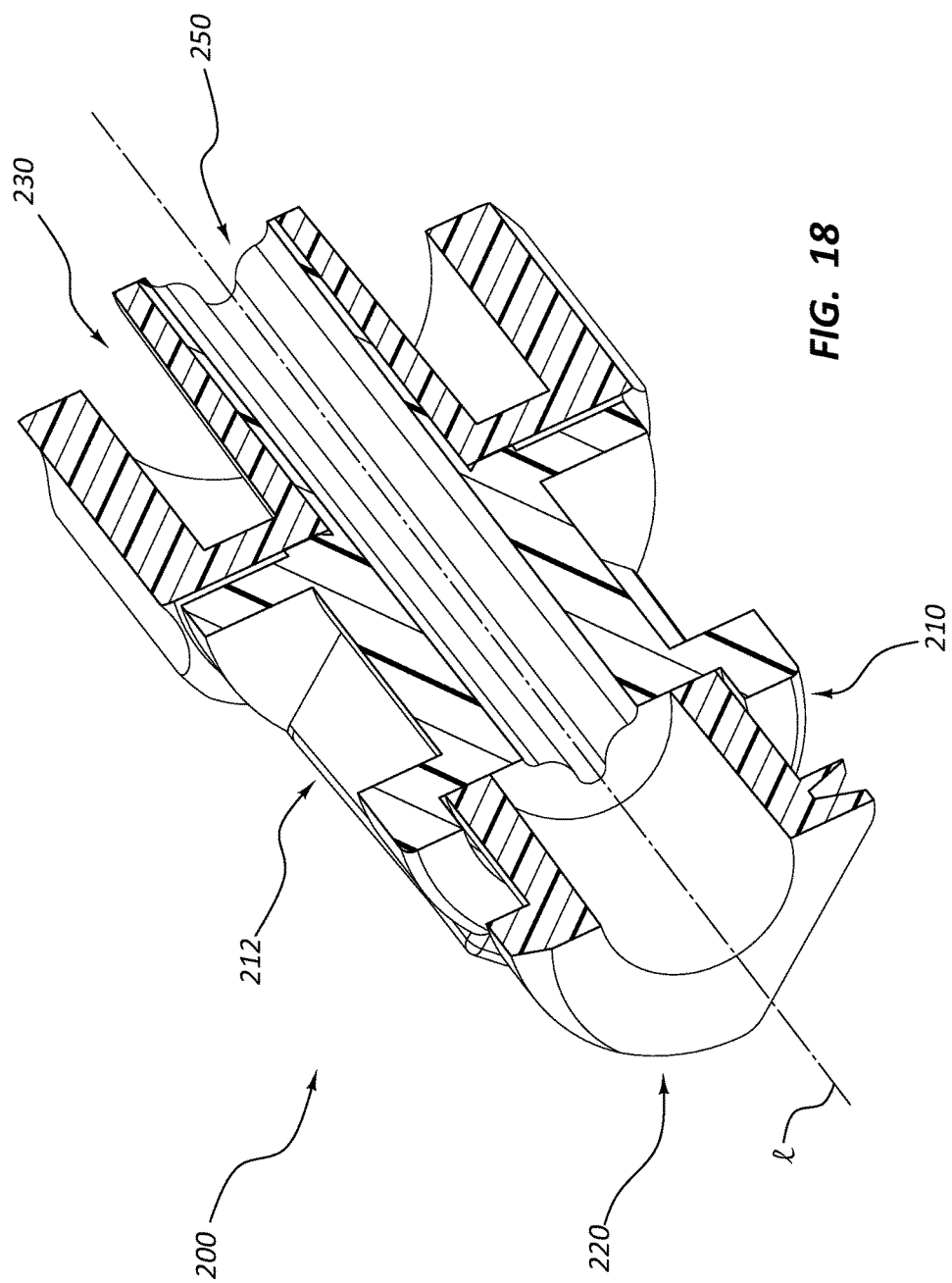
FIG. 18 is a cross-sectional perspective view of the medical plug delivery device of FIG. 9 cut through plane 17-17 of FIG. 9.

In some embodiments, a portion of the channel 250 may taper. For example, the channel 250 may include a tapering region 259 (see FIG. 15) that tapers toward the longitudinal axis (/) of the housing 210. For example, as shown in FIG. 15, the tapering region 259 may taper toward the longitudinal axis of the housing 210 in a proximal direction such that a first portion of the tapering region 259 is narrower than a second portion of the tapering region 259 that is distal of the first portion. For instance, in the depicted embodiment, a portion of the channel 250 that is defined by the central member 212 narrows toward the proximal end of the central member 212.

In other embodiments, the tapering region 259 may taper toward the longitudinal axis (/) of the housing 210 such that a first portion of the tapering region 259 is narrower than a second portion of the tapering region that is proximal of the first portion. Stated differently, in some embodiments, the channel 250 may narrow toward its distal end.

In some embodiments, the tapering region 259 tapers toward the longitudinal axis at an angle (θ) of between 0.2 and 3.5 degrees, such as between 0.3 and 1.5 degrees. In some embodiments, the tapering region 259 is between 5 and 40 mm in length. In other words, in some embodiments, the channel 250 may taper over a distance of between 5 and 40 mm, such as between 15 and 25 mm.

In some embodiments, tapering occurs along both the inward-most points 254 and the outward-most points 256. In other words, in some embodiments, both $R_1$ and $R_2$ may change in length across the channel 250. In other embodiments, tapering occurs only along the inward-most points 254. In other words, in some embodiments, $R_1$ (but not $R_2$) changes in length across the channel 250. The tapering of the channel 250 may help maintain the medical plug 240 within the channel 250 prior to wetting of the medical plug 240 and/or deployment of the medical plug 240 from the channel 250. Stated differently, due to the taper, one portion (e.g., a proximal portion) of the housing 210 may provide more interference with the medical plug 240 than at the opposite end of the housing 210.

The medical plug delivery device 200 may be used to deliver a medical plug 240 to a patient. For example, in some embodiments, a practitioner may initially obtain a medical plug delivery device, such as the medical plug delivery device 200 described above.

A proximal end of the medical plug delivery device 200 may then be connected to a fluid delivery device (e.g., the syringe depicted in FIG. 1). In some embodiments, the fluid delivery device is preloaded with fluid (e.g., water or saline) prior to attachment of the medical plug delivery device 200 to a distal end of the fluid delivery device. Stated differently, the fluid delivery device may be partially or completely filled with fluid prior to attachment to the medical plug delivery device 200.

Once the proximal end of the medical plug delivery device 200 is connected to the fluid delivery device, the practitioner may deliver fluid from the fluid delivery device into the medical plug delivery device 200 to remove air bubbles from the medical plug delivery device 200.

More particularly, as the practitioner delivers fluid from the fluid delivery device, the fluid may flow in a distal direction around the medical plug 240 through the elongate passageways disposed around the medical plug 240. The delivery of fluid through the elongate passageways disposed around the medical plug 240 may allow for the removal of air bubbles from, or otherwise priming the medical plug delivery device 200 prior to deployment of the medical plug 240.

As the bubbles are removed from the medical plug delivery device 200, the medical plug 240 may become wetted. In other words, fluid from the fluid delivery device may hydrate the medical plug 240 as fluid is advanced through the medical plug delivery device 200 to removes bubbles. Wetting of the medical plug 240 may cause expansion of the medical plug 240 into the lobes 258 of the channel 250. Stated differently, the medical plug 240 may expand toward the outward-most points 256 of the perimeter 252 of the channel 250, thereby at least partially filling a region between an inward-most point 254 and an outward-most point 256. Such expansion may cause partial or complete occlusion of the elongate channels around the medical plug 240.

Wetting of the medical plug 240 may increase the lubricity of the medical plug 240, thereby facilitating both ejection of the medical plug 240 from the medical plug delivery device 200 and advancement of the medical plug 240 through a lumen of an elongate tube (e.g., an introducer) to an interior portion (e.g., a void) of a patient.

Once the air bubbles have been removed from the medical plug delivery device 200, the distal end of the medical plug delivery device 200 may be connected to an elongate tube in fluid communication with a void in a patient (e.g., an introducer). For example, the practitioner may couple the distal end of the medical plug delivery device 200 to an introducer sheath or catheter, such as an introducer sheath used in a biopsy procedure.

The practitioner may then eject fluid from the fluid delivery device, thereby distally displacing fluid into the medical plug delivery device 200. As the fluid is displaced in a distal direction, the fluid may exert a distal force on the medical plug 240 disposed within the channel 250, thereby causing distal displacement and ejection (i.e., deployment) of the medical plug 240 from the channel 250 of the medical plug delivery device 200 into an elongate tube (e.g., an introducer) that is in fluid communication with a void of the patient. As the fluid is advanced, the displaced fluid may push the medical plug 240 through the elongate tube and into the desired void. The inserted medical plug 240 may serve any suitable purpose, such as obstructing fluid flow, inducing blood coagulation, and/or providing a scaffold to promote tissue growth.

In some embodiments, instead of wetting the medical plug 240 prior to attaching the medical plug delivery device 200 to the introducer, the medical plug 240 is simultaneously wetted and discharged from the medical plug delivery device 200. In other words, the medical plug 240 may be hydrated as it is ejected through a distal opening at the distal end of the housing 210 of the medical plug delivery device 200.

Figure 20:
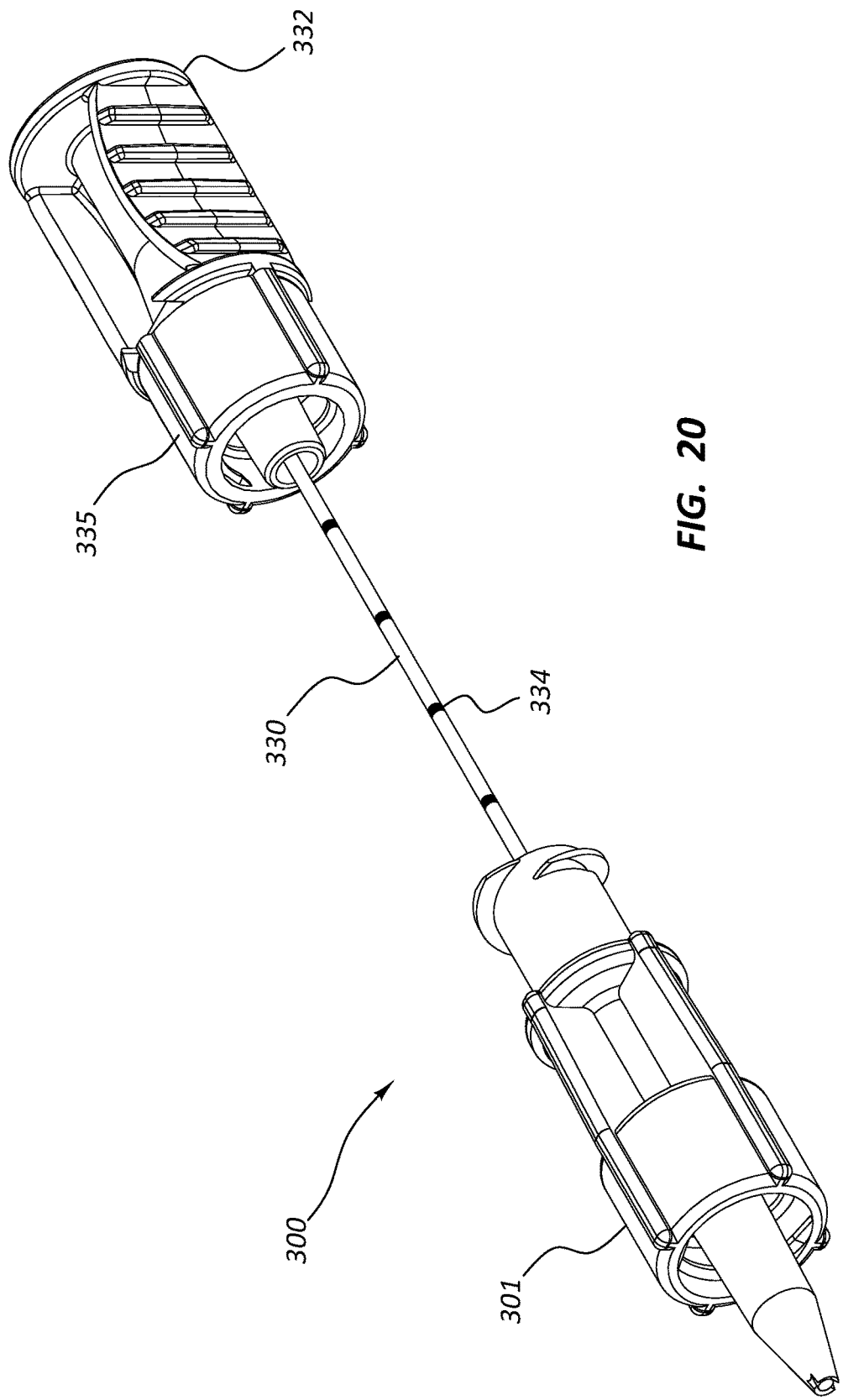
FIG. 20 is a perspective view of a medical plug delivery system.
Figure 21:
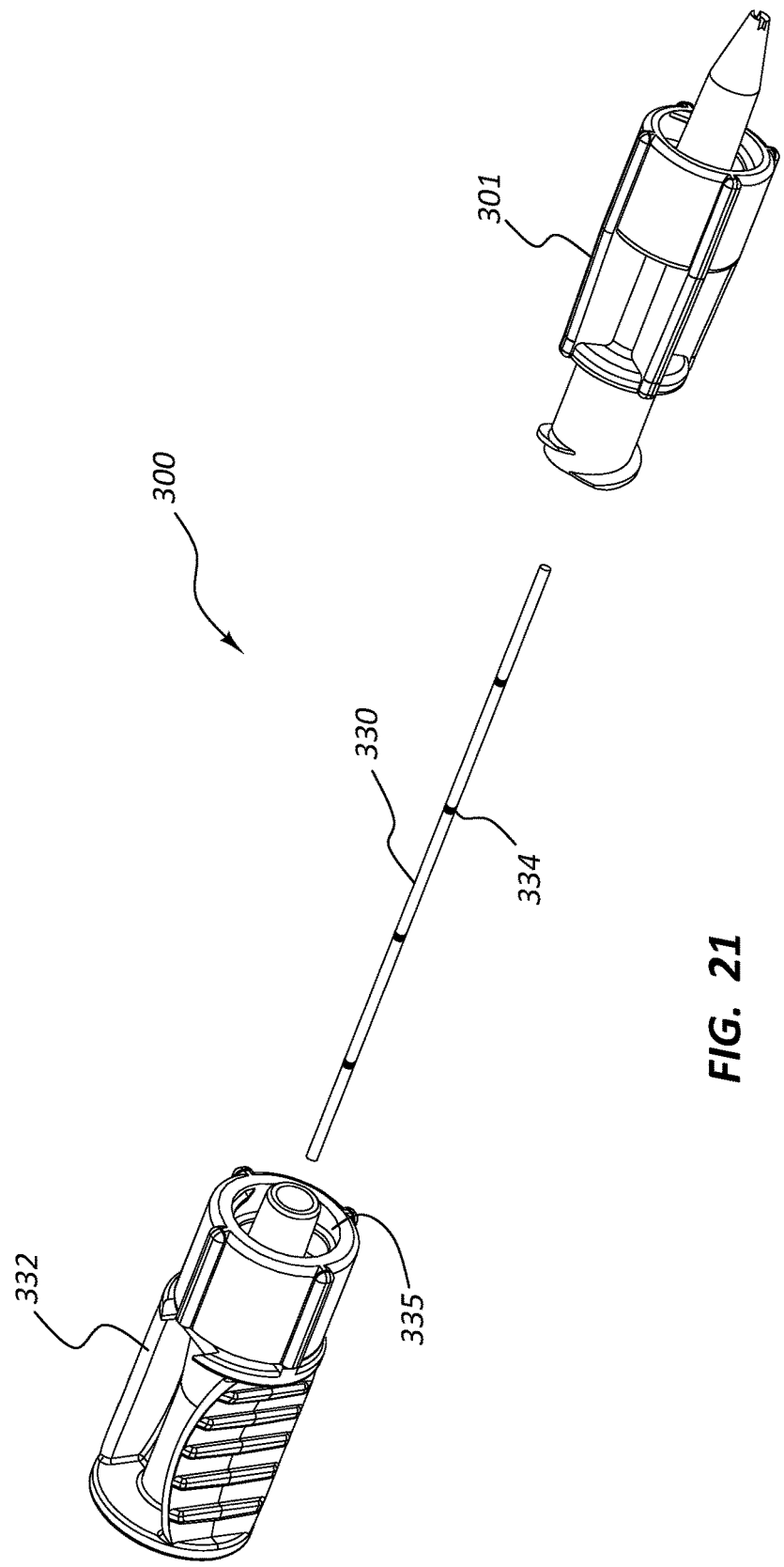
FIG. 21 is an exploded, perspective view of a medical plug delivery system.

FIGS. 20-21 provide a perspective view of a plug delivery system 300 for delivering a medical plug to a void within a patient. As depicted in FIGS. 20-21, the medical device system 300 may include a plug holder 301 and a stylet 330. In some embodiments, the medical plug delivery system may further comprise a plug or pledget 309.

Figure 24:
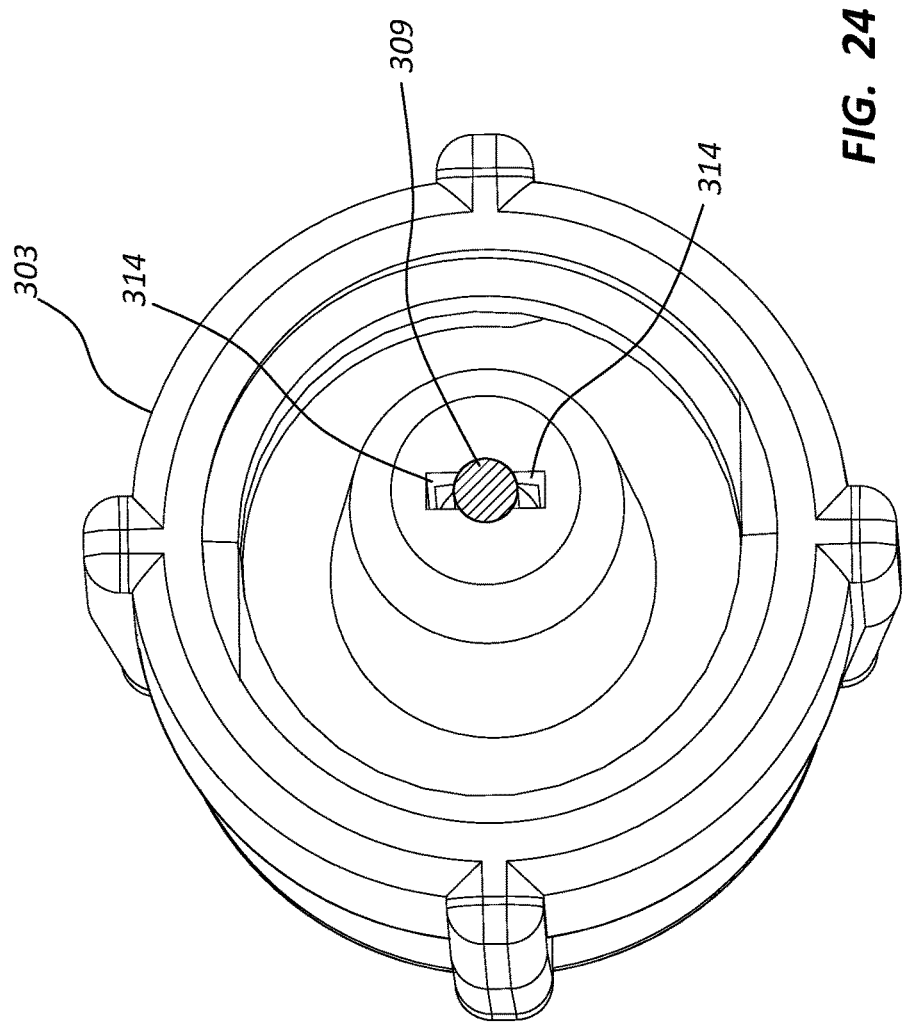
FIG. 24 is a cross-sectional perspective view of a medical plug delivery system of FIG. 20 through plane 24-24 of FIG. 22.

As depicted in FIGS. 22-24, in some embodiments, the plug holder 301 may include a housing 303. The housing 303 may include an adaptor 305 at its proximal end 304 configured to be connected to a medical fluid delivery device, such as a syringe. For example, the housing 303 may include a female Luer lock fitting 305 at its proximal end 304. The female Luer lock fitting 305 may be configured to sealingly mate with a male Luer lock fitting of a fluid delivery device, such as a syringe or other medical device. The housing 303 may also include a male Luer lock fitting 306 at the housing distal end 307. The male Luer lock fitting 306 may be configured to sealingly mate with a female Luer lock fitting of an introducer which is disposed within a patient. The housing 303 may be generally cylindrical and a single component or monolithic construction.

Figure 27:
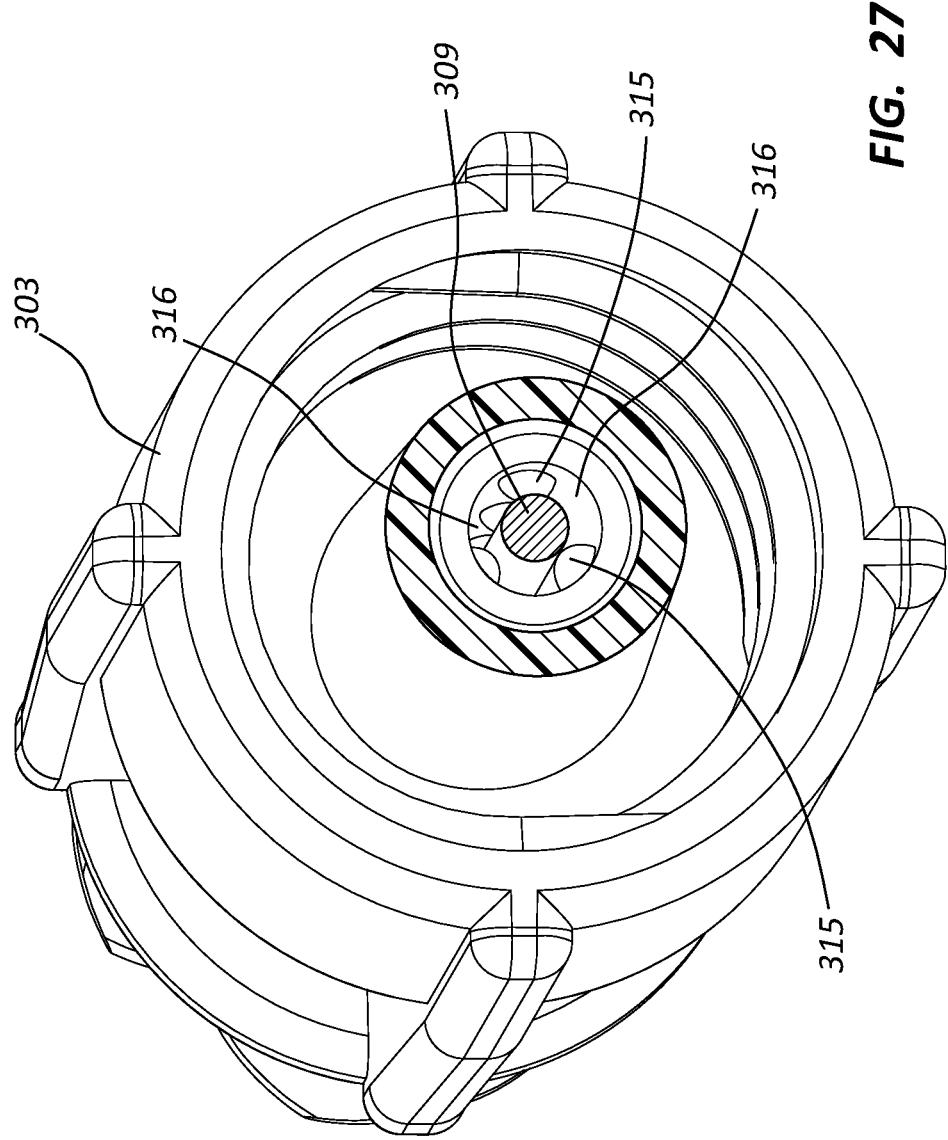
FIG. 27 is a cross-sectional perspective view of a medical plug delivery system of FIG. 20 through plane 27-27 of FIG. 25.

The housing 303 may include a lumen 308 configured to pass from the housing proximal end 304 to the housing distal end 307. The lumen 308 may be configured to accommodate the plug 309. Thus, the lumen 308 may define a cavity configured to retain the plug 309. The cavity 308 may be centrally disposed within the plug holder 301 and may be configured to orient the plug 309 within the plug holder 301 such that the longitudinal axis of the plug 309 is aligned with the longitudinal axis of the plug holder 301 or lumen 308. The lumen 308 may be generally tapered from the lumen proximal end 311 to the lumen distal end 312 with the largest diameter located at the proximal end 311 and the smallest diameter located at the distal end 312. The lumen 308 may include a medical plug retention section 310 positioned near the lumen distal end 312. The retention section 310 may be configured to retain the plug 309 within the lumen 308 until displacement of the plug 309 is desired and to permit removal of air from the lumen 308. The plug retention section 310 may be a portion of the lumen 308 with an inner diameter less than the outer diameter of the plug 309. By way example, the outer diameter of the plug 309 may be one gauge size different from the medical plug retention section 310 (such as medical plug 309 being 20 gauge and the inner diameter of the medical plug retention section 310 being 21 gauge). The plug retention section 310 may be 3 to 8 mm in length (for example, approximately 5 mm in length) and be configured to frictionally engage a portion of the plug 309. The proximal end of the retention section 310 may include a chamfer 313 to facilitate passage of the stylet 330. The plug retention section 310 may also be configured to permit fluid flow past the plug 309. The plug retention section 310 may include at least one longitudinal, radially outwardly, extending channel 314 as shown in FIGS. 23-24. The channel 314 may be configured to not be sealed or closed off by the plug 309 and to permit fluid flow, including air, through the channel 314. Alternatively, as shown in FIGS. 25-27, the plug retention section 310 may include radially inwardly extending detents 315. The detents 315 may be configured to provide a friction engagement with a portion of the plug 309 and to allow for fluid flow between the detents 315. The plug retention section 310 may include at least one ring of at least three equally spaced detents. Preferably, three detent rings may be located within the plug retention section 310 of the lumen 308. The detents 315 may be sized to effectively reduce the lumen 308 diameter in the medical plug retention section 310. The detents 315 may create a frictional engagement with the plug 309 to retain the plug 309 within the plug holder 301 until the plug is delivered into the patient. For example, the plug 309 may have a 20 gauge diameter and the detents 315 may effectively reduce the diameter to 21 gauge. The spaces between the detents 315, both longitudinal and lateral, may not be sealed by the plug 309, providing an annular gap 316 between the plug 309 and a lumen wall 318. The annular gap 316 may be partially interrupted by the detents 315. The annular gap 316 may be configured to not be sealed or closed off by the plug 309 and to permit fluid flow, including air, through the gap 316.

The housing 303 may further comprise a frustoconical shaped extension 317 of the housing 303 with the lumen 308 extending through the extension 317. The angle of the frustoconical extension 317 may be greater than the angle of the male Luer lock adaptor 306. The extension 317 may extend into the introducer connector and may not create a fluid-tight seal with the introducer connector. The extension 317 may be configured to extend the lumen distal end 312 to be near and in alignment with the proximal end of the introducer needle allowing for passage of the plug 309 from the plug holder 301 into the introducer without the plug 309 getting caught within the introducer connector and folding on its self.

The stylet 330 may be configured to push or displace the plug 309 from the plug holder 301 into the introducer or void of a patient. The stylet 330 may be configured to pass through the housing lumen 308 from the lumen proximal end 311 to the lumen distal end 312 and into the introducer. The stylet 330 may comprise a rod 331 and a handle 332 or finger grip. The rod 331 may be made from a metal or rigid plastic, such as polycarbonate. The stylet distal end 333 may be squared-off to provide a flat surface to push against the plug 309. The diameter of the rod 331 may be sized to pass through the plug retention section 310 of the lumen 308 as well as into the introducer needle. The length of the rod 331 may be sized to extend through the plug holder 301 and partially into the introducer cannula for displacement of the plug 309 into the introducer cannula. Alternatively, the length of the rod 331 may be such that rod 331 may extend through the plug holder 301 and through the distal end of the introducer cannula for displacement of the plug 309 through the introducer and into the void of a patient.

In certain embodiments, introducers may be configured with different cannula lengths. To accommodate the different introducer cannula lengths, the stylet 330 length may be sized to extend slightly beyond the distal end of the longest introducer cannula. The stylet 330 may include insertion depth markings 334 on the rod 331 to be used when a shorter introducer cannula is used. The markings 334 may be single or multiple bands spaced approximately 1 cm apart. The practitioner may determine the length of stylet 330 needed to displace the plug 309 to the desired location, either within the introducer needle or into the void of a patient, and then insert the stylet 330 into the plug holder 301 until the pre-determined depth mark is reached.

The stylet handle 332 may be configured to be held between the thumb and at least one finger of a practitioner. The handle 332 may comprise features to enhance gripability, such as roughed surface, ribs, detents, and other features known in the art. The handle 332 may be configured to connect to the female Luer lock adaptor 305 of the housing 303. The distal portion of the handle 332 may be structured as a male Luer lock or Luer slip adaptor 335.

The plug 309 may be of any suitable composition, shape, and/or size. For example, in some embodiments, the plug 309 may include, comprise, or consist of a bioabsorbable material. In some embodiments, the bioabsorbable material (or a portion thereof) is derived from animal tissue, such as pig skin or cow skin. In some embodiments, the bioabsorbable material is a collagen-containing material, such as a gelatin foam from an animal source. In other or further embodiments, the bioabsorbable material (or a portion thereof) is a synthetic polymer, such as polylactic acid, polyglycolide, or poly(lactic-co-glycolic acid). In some embodiments, the plug 309 includes or consists of a non-bioabsorbable material, such as polyvinyl alcohol or polyvinyl acetate. In some embodiments, the plug 309 includes a dye. The dye may facilitate visualization of the plug 309 when the plug 309 is disposed within the plug holder 301. In some embodiments, the plug 309 may change colors when contacted with fluid (e.g., water or saline), thereby allowing a practitioner to visually determine when the plug 309 has been wetted.

The plug 309 may be generally elongate in shape. For example, in some embodiments, the plug 309 is an elongate piece of material that has been rolled into a substantially cylindrical shape of between 1 mm and 5 mm (e.g., approximately 2 mm) in diameter. The plug 309 may have a length that is at least 2-fold, at least 5-fold, and/or at least 10-fold longer than the diameter of the plug 309. In some embodiments, the plug 309 is between 10 mm and 30 mm (e.g., approximately 20 mm) in length.

The plug delivery system 300 of FIGS. 20-21 may be used to deliver a dry or wetted plug 309 to a void within a patient. For example, in some embodiments the practitioner may initially obtain a plug holder 301, such as the plug holder 301 described above.

The practitioner may select a dry technique (one step or two steps) or a wet technique for delivering the plug 309 into a void of a patient. When the two-step dry technique is selected, the plug holder 301 is connected to the connector of an introducer via the distal male Luer lock adaptor 306. The stylet 330 configured to extend through the plug holder 301 and into the introducer cannula may then be inserted into the proximal end of the plug holder 301. As the stylet 330 is advanced, the stylet distal end 333 may make contact with the proximal end of the plug 309. As a distally directed force is applied to the plug 309 by the stylet 330, the force may exceed the frictional engagement force between the plug 309 and the lumen retention section 310 of the plug holder 301. As the frictional engagement force is surpassed, the plug 309 will be displaced from the lumen 308 into the introducer cannula. The plug holder 301 and stylet 330 may then be removed from the introducer. A trocar, which is matched to the length of the introducer cannula, may be inserted into the introducer cannula such that the plug 309 is further displaced from the introducer cannula into the void of a patient.

Alternatively, the practitioner may select a single-step, dry delivery technique. The plug holder 301 may be connected to the proximal end of an introducer via the distal male Luer lock adaptor 306 of the plug holder 301. The practitioner may determine the combined length of the plug holder 301 and the introducer cannula. The stylet 330 may be inserted into the lumen proximal end 311. As the stylet 330 is advanced, the stylet distal end 333 may make contact with the proximal end of the plug 309. A distally directed force may be applied to the plug 309. The distally directed force may exceed the frictional engagement force between the plug 309 and the lumen retention section 310 of the plug holder 301. As the frictional engagement force is surpassed, the plug 309 may be displaced from the lumen 308 of the plug holder 301 into the introducer cannula. The plug 309 may be further displaced into the void of a patient as the stylet 330 is advanced. The stylet 330 advancement may be stopped by the practitioner when the pre-determined length of the stylet 330 has been inserted. The insertion length may be determined by the practitioner by observing the depth markings 334 on the stylet 330. The plug holder 301 may be disconnected from the introducer.

Alternatively, the practitioner may select a wet medical plug delivery technique. The proximal female Luer lock adaptor 305 of the plug holder 301 may be connected to a fluid delivery device, such as a syringe at least partially filled with a fluid. The fluid delivery device may deliver fluid into the lumen 308 of the plug holder 301 such that the lumen 308 becomes free of air and the plug 309 is wetted. The fluid delivery device may deliver a fluid such as water, saline, contrast, any mixture thereof, or any other fluid. If desired, air may be removed from the lumen 308 in the traditional manner (i.e., by orienting the plug holder 301 such that the distal end of the plug holder 301 is pointed upward, tapping the plug holder 301, and ejecting air bubbles by delivering fluid through the plug holder 301). The flow channel 314 through the medical plug retention section 310 or the annular gap 316 between the plug 309 and the lumen wall 318 permit fluid to flow through the lumen 308.

The distal male Luer lock adaptor 306 may be connected to a female Luer lock connector of an introducer that has been inserted into a patient. The connection may bring the lumen distal end 312 close to and in alignment with the proximal end of the introducer cannula. The practitioner may then eject fluid from the fluid delivery device, thereby distally displacing fluid into the lumen 308. As the fluid is displaced in a distal direction, the fluid may exert a distal force on the medical plug 309 disposed within the lumen 308. The hydraulic force may surpass the engagement force of the retention section 310 on a portion of the plug 309, thereby causing distal displacement and ejection of the plug 309 from the lumen 308 of the plug holder 301 into an introducer cannula that is in fluid communication with a void of the patient. As the fluid is advanced, the displaced fluid may push the plug 309 through the introducer cannula and into the void of a patient. The inserted plug 309 may serve any suitable purpose, such as obstructing fluid flow, inducing blood coagulation, and/or providing a scaffold to promote tissue growth.

Figure 28:
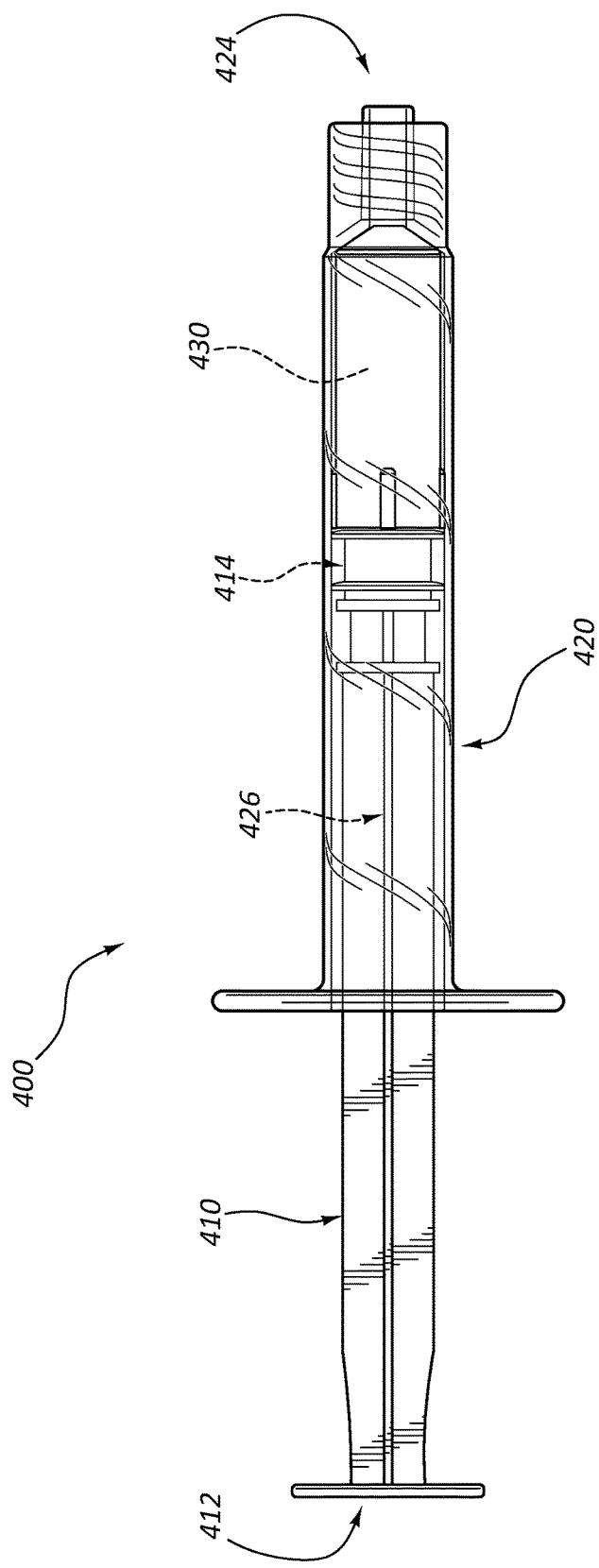
FIG. 28 is a side view of a medical device for delivering a plug.

FIG. 28 provides a side view of a medical device 400 for delivering a plug to a void within a patient. As depicted in FIG. 28, the medical device 400 may include a plunger 410, a syringe body 420, and a plug holder 430 (which may alternatively be referred to as a plug cartridge). The plug holder 430 may define a plug holder body, and may comprise an integrally formed element. Further, in some embodiments, the plug holder 430 may be an integrally formed portion of the syringe body 420.

The plunger 410 may include a handle 412 adjacent the proximal end of the plunger and a seal 414 adjacent the distal end of the plunger 410. The plunger 410 may be configured to be at least partially disposed within the syringe body 420 such that advancement and retraction of the plunger 410 causes displacement of fluid within a reservoir 426 in the syringe body 420. The syringe body 420 may be configured to couple to a proximal end of an elongate sheath, such as an introducer sheath or catheter to deliver fluid and/or a plug to a patient. For example, in the depicted embodiment, the syringe body 420 includes a male Luer lock connection at an orifice at the distal end 424 of the syringe body 420. In some embodiments, both the syringe body 420 and the plug holder 430 are substantially transparent, thereby allowing the practitioner to visualize wetting and ejection of the plug as described below. In other embodiments, the syringe body 420 and/or the plug holder 430 are opaque.

The plug holder 430 may be configured to be disposed within the syringe body 420 at a position that is distal of the plunger 410. The plug holder 430 may be configured to remain adjacent the distal end of the syringe body 420 during operation of the medical device 400. Stated differently, the plug holder 430 may be coupled to the syringe body 420, for example by an interference fit within the syringe body 420. In some embodiments, the plug holder 430 is generally cylindrical in shape.

Figure 29:
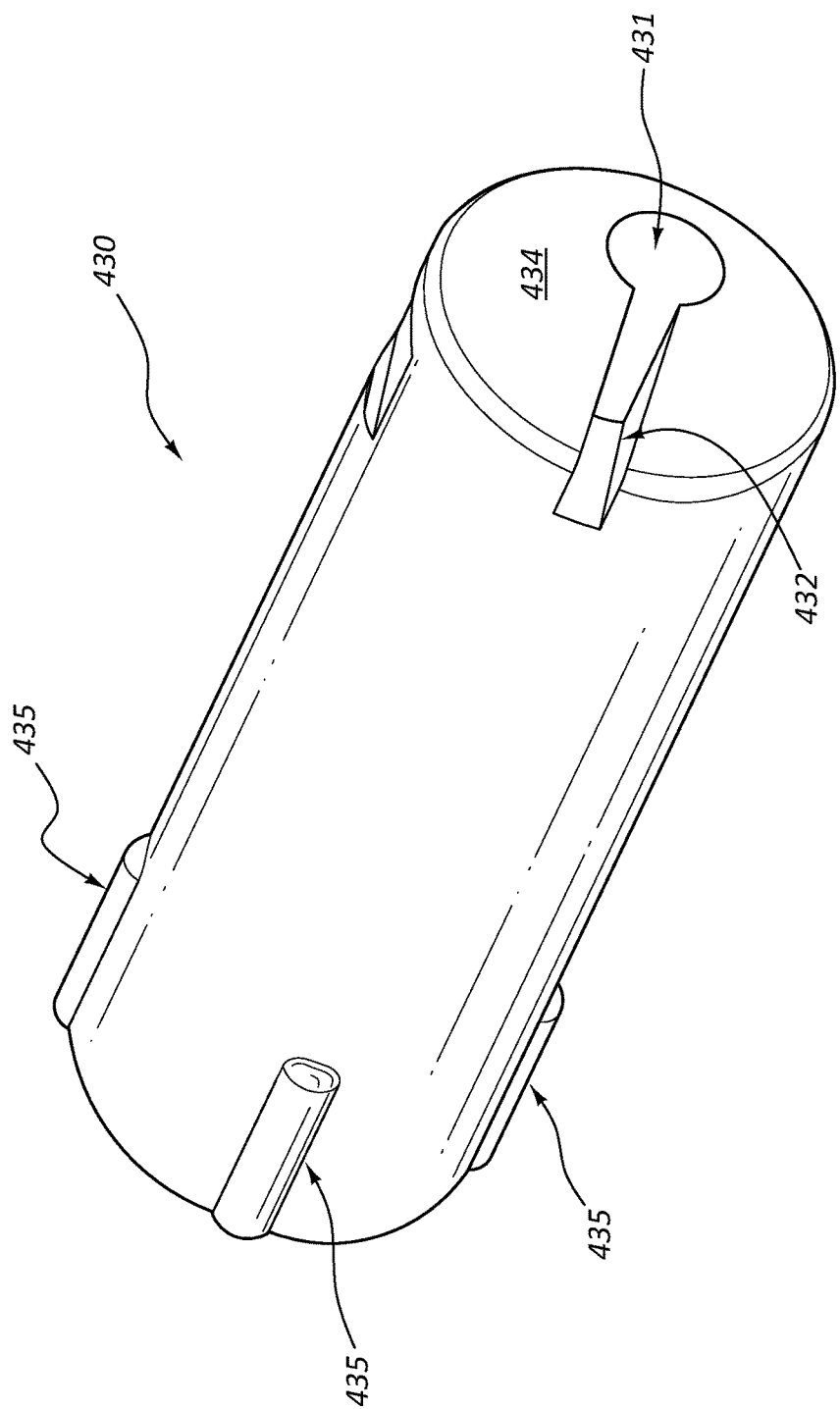
FIG. 29 is a perspective view of a plug holder for the medical device of FIG. 28.
Figure 30:
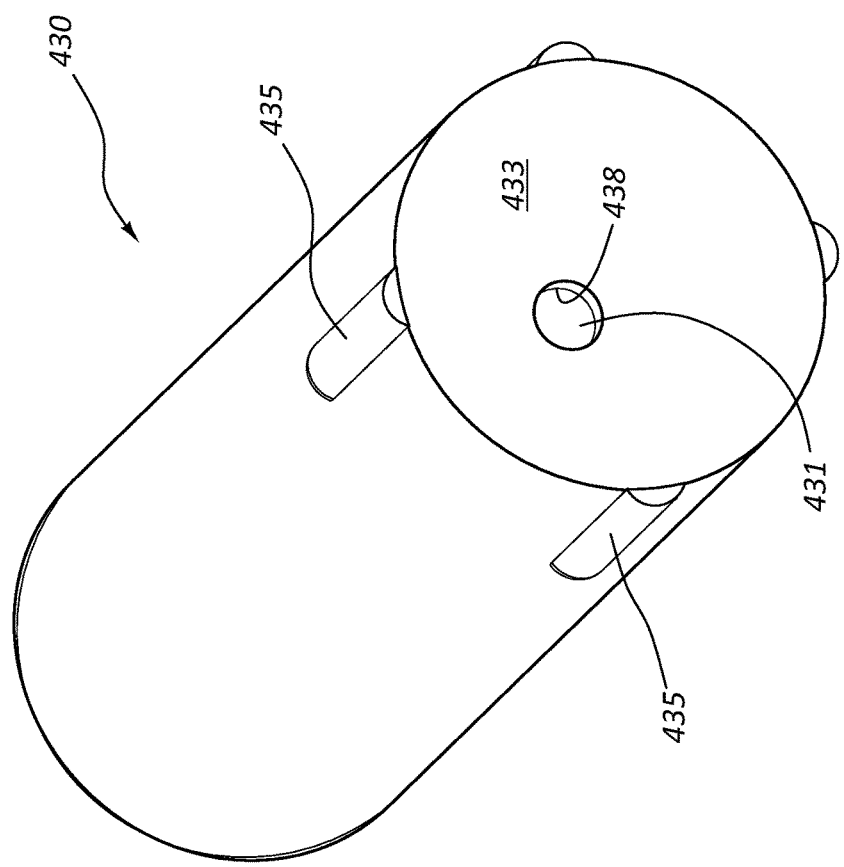
FIG. 30 is another perspective view of the plug holder of FIG. 29.
Figure 31:
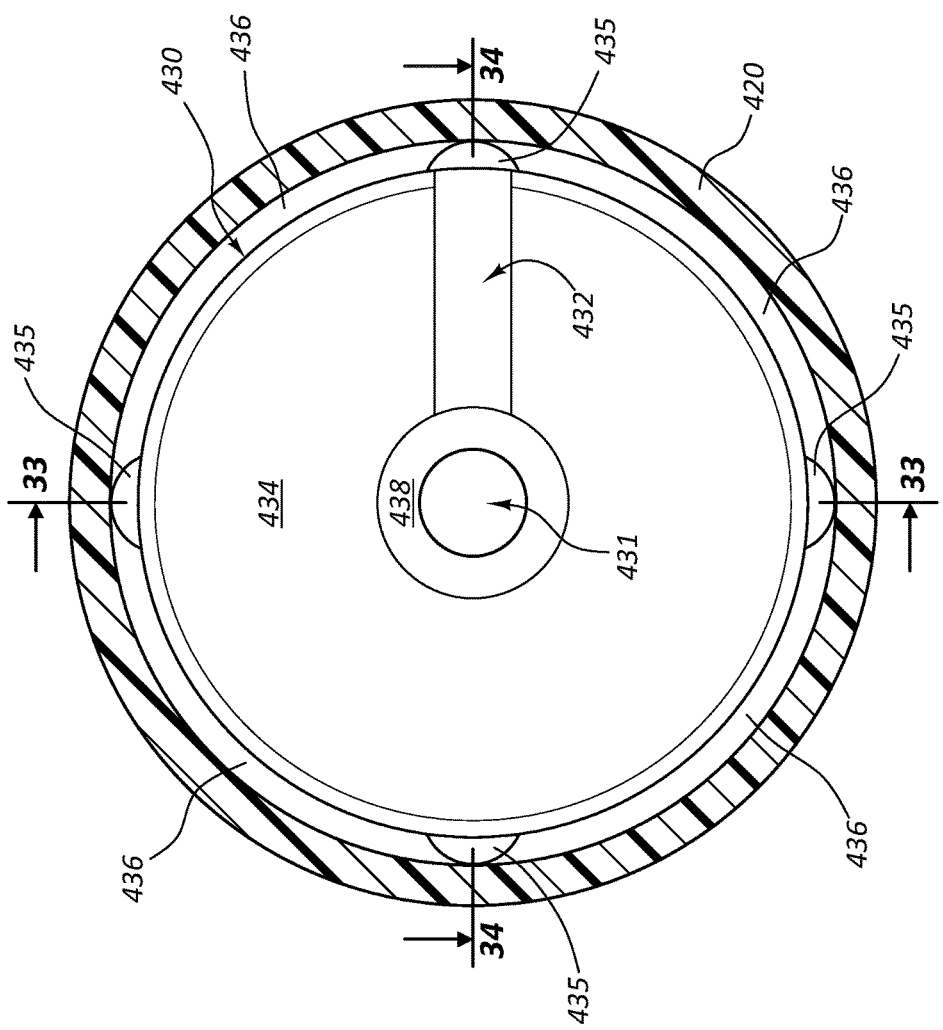
FIG. 31 is a front view of the plug holder of FIGS. 29 and 30, along with a portion of the medical device of FIG. 28.
Figure 32:
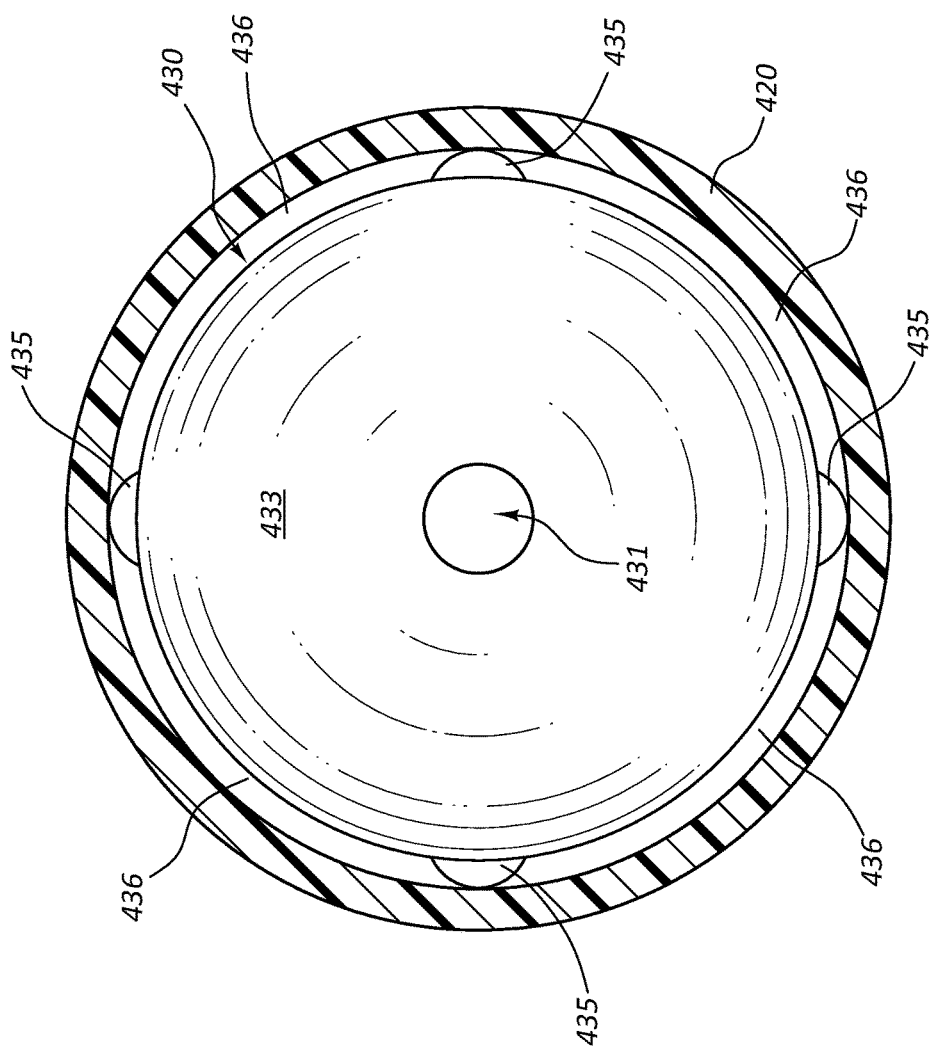
FIG. 32 is a rear view of the plug holder of FIGS. 29-31, along with a portion of the medical device of FIG. 28.
Figure 33:
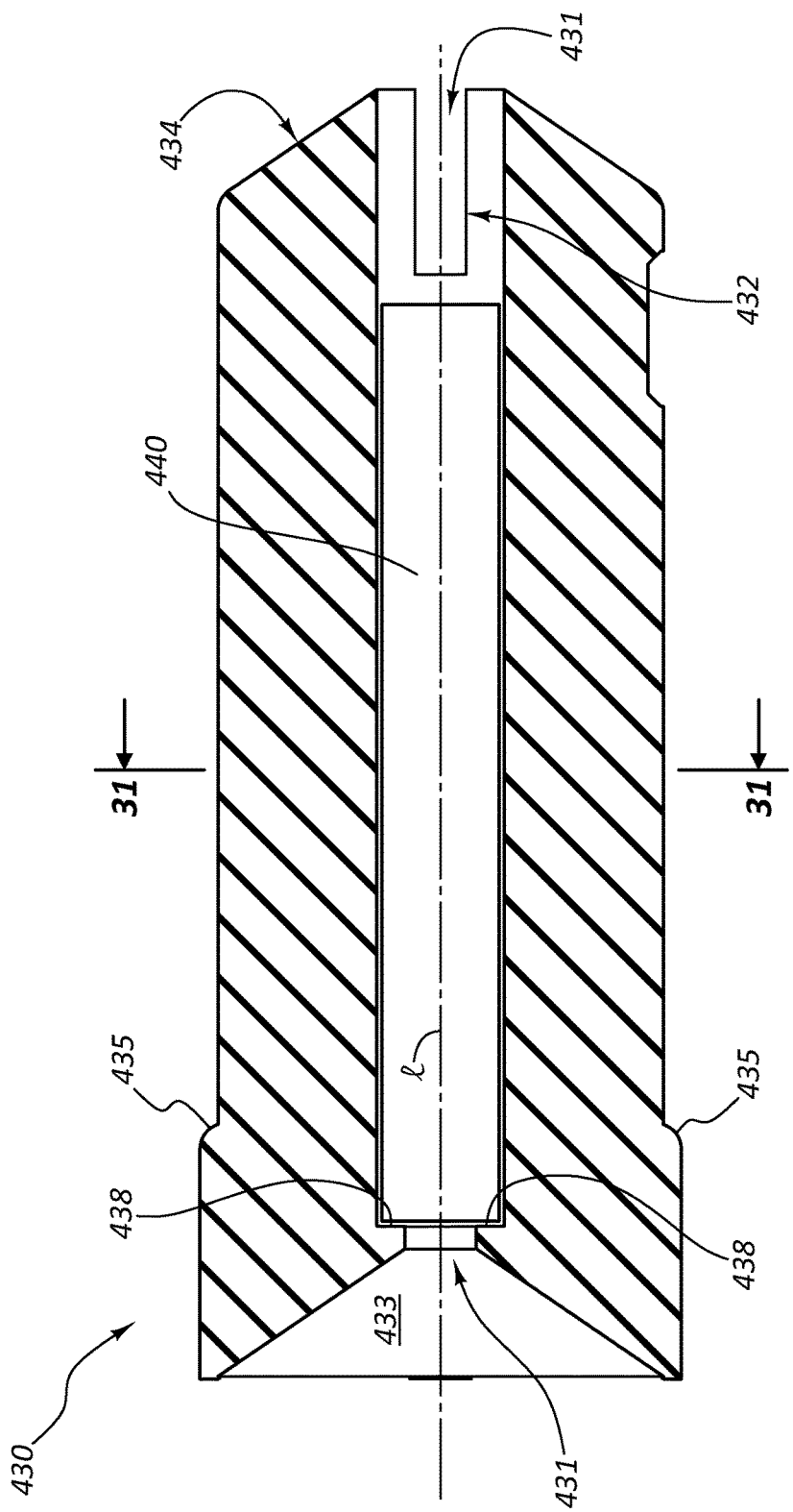
FIG. 33 is a cross-sectional view of the plug holder of FIGS. 29-32.
Figure 34:
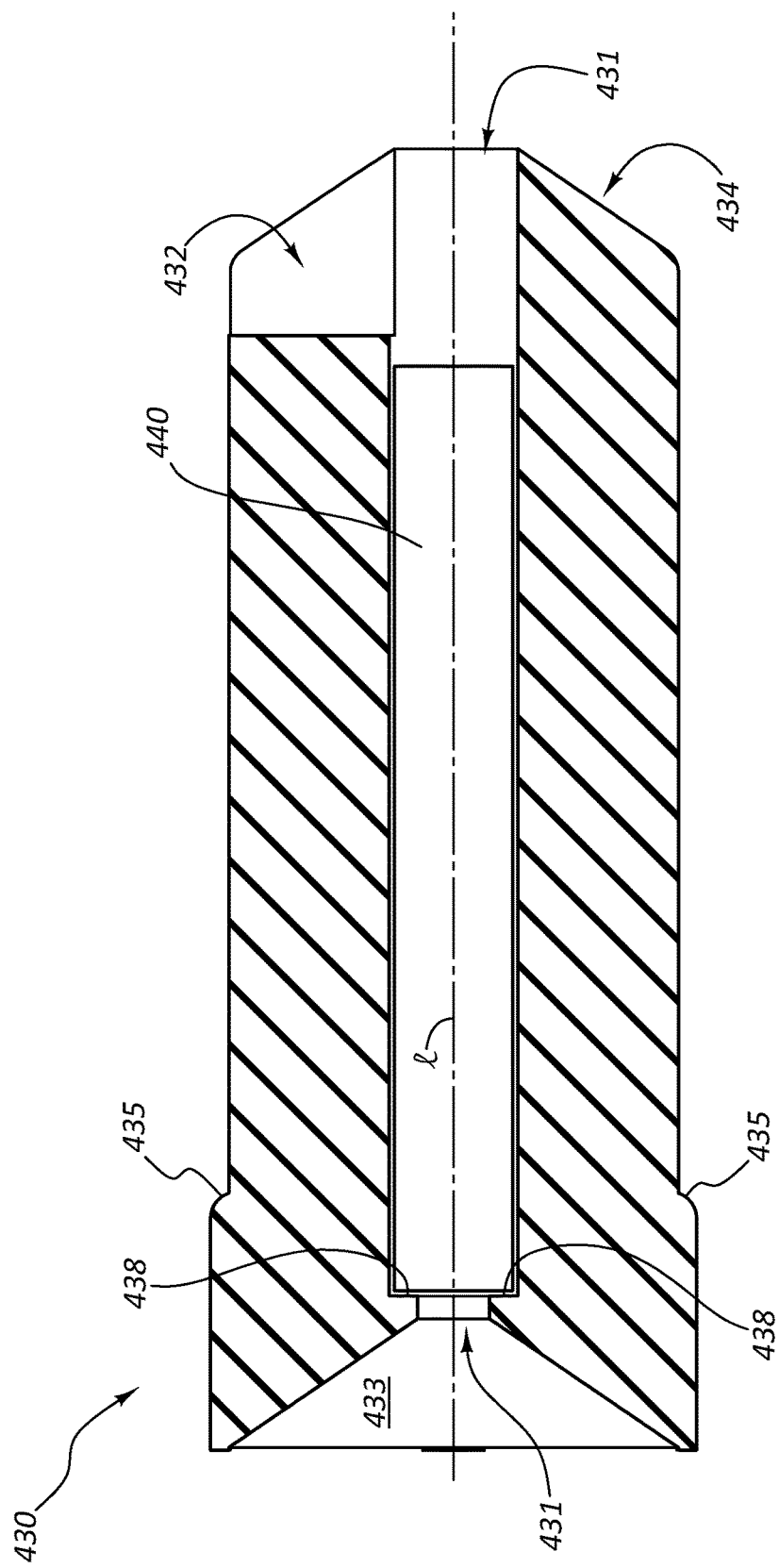
FIG. 34 is another cross-sectional view of the plug holder of FIGS. 29-33.
Figure 35:
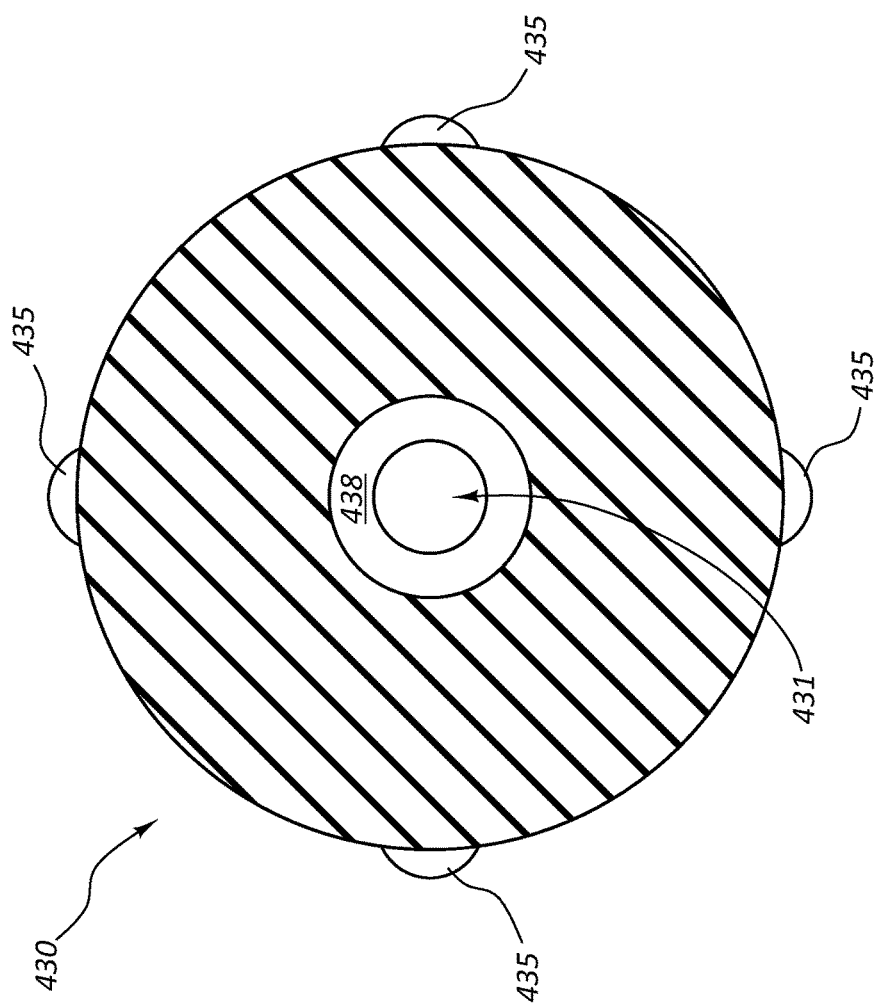
FIG. 35 is another cross-sectional view of the plug holder of FIGS. 29-34.

The plug holder 430 is further shown in FIGS. 29-35. More particularly, FIG. 29 provides a perspective view that shows a distal end of the plug holder 430. FIG. 30 provides a different perspective view that shows a proximal end of the plug holder 430. FIGS. 31 and 32 provide front (FIG. 31) and rear (FIG. 32) views of the plug holder 430. Note that in FIGS. 31 and 32, a cross-section of the syringe body 420 has been added to show the relationship of the plug holder 430 and the syringe body 420 when the plug holder 430 is disposed within the syringe body 420 as shown in FIG. 28. FIGS. 33 and 34 provide alternative cross-sectional views of the plug holder 430. More particularly, FIG. 34 provides a cross-sectional view of the plug holder 430 through plane 34-34 of FIG. 31, while FIG. 34 provides a cross-sectional view of the plug holder 430 through plane 34-34 of FIG. 28. FIG. 35 provides a cross-sectional view of the plug holder 430 through a plane disposed at the position on the plug holder 430 indicated by plane 35-35 of FIG. 33.

As shown in FIGS. 29-35, the plug holder 430 may include a lumen 431, a side channel 432, a proximal surface 433, a distal surface 434, a plurality of fins 435, and a shoulder 438.

The lumen 431, as shown in FIGS. 33 and 34, may extend along the length of the plug holder 430. For example, the lumen 431 may be centered around a longitudinal axis (/) of the plug holder 430 and extend at least from a proximal surface 433 of the plug holder 430 to a distal surface 434 of the plug holder 430.

The lumen 431 may be configured to accommodate a plug 440. (The plug 440 is shown in FIGS. 33 and 34 but omitted from the remaining FIGS. 29-32 and 35.) Thus, the lumen 431 may define a cavity configured to retain the plug 440. The plug 440 may be of any suitable composition, shape, and/or size. For example, in some embodiments, the plug 440 may include or consist essentially of a bioabsorbable material. In some embodiments, the bioabsorbable material (or a portion thereof) is derived from animal tissue, such as pig skin or cow skin. In some embodiments, the bioabsorbable material is a collagen-containing material, such as a gelatin foam from an animal source. In other or further embodiments, the bioabsorbable material (or a portion thereof) is a synthetic polymer, such as polylactic acid, polyglycolide, or poly(lactic-co-glycolic acid). In some embodiments, the plug 440 includes or consists essentially of a non-bioabsorbable material, such as polyvinyl alcohol or polyvinyl acetate. In some embodiments, the plug 440 includes a dye. The dye may facilitate visualization of the plug 440 when the plug 440 is disposed within the plug holder 430. In some embodiments, the plug 440 may change colors when contacted with fluid (e.g., water or saline), thereby allowing a practitioner to visually determine when the plug 440 has been wetted.

The plug 440 may be generally elongate in shape. For example, in some embodiments, the plug 440 is an elongate piece of material that has been rolled into a substantially cylindrical shape of between 1 mm and 5 mm (e.g., approximately 2 mm) in diameter. The plug 440 may have a length that is at least 2-fold, at least 5-fold, and/or at least 10-fold longer than the diameter of the plug 440. In some embodiments, the plug is between 10 mm and 30 mm (e.g., approximately 20 mm) in length.

The plug holder 430 may also include a side channel 432 that extends radially outward from a distal portion of the lumen 431. As described in further detail below, the side channel 432 may allow fluid (e.g., water or saline) to flow radially outward from the lumen 431 toward a gap 436 between the plug holder 430 and the syringe body 420 (see FIGS. 28 and 29 in which the syringe body 420 has been added in cross-section to show the gaps 436).

The proximal surface 433 of the plug holder 430 may be any suitable shape. In some embodiments, the proximal surface 433 is shaped to complement the shape of the seal 414 of the plunger 410 (see FIG. 28). For example, in the depicted embodiment, the proximal surface 433 of the plunger holder 430 is frustoconical in shape, thereby providing a complementary surface to the conical tip of the seal 414. In other words, the seal 414 and the proximal surface 433 may be shaped such that, when the plunger 410 is fully advanced, the seal 414 contacts the entire surface of the proximal surface 433. In some embodiments, the proximal surface 433 may be some other shape (e.g., a planar shape).

Like the proximal surface 433, the distal surface 434 of the plug holder 430 may be any suitable shape. In some embodiments, the distal surface 434 is shaped to complement the shape of an interior distal surface of the syringe body 420. For example, a distal surface 434 of the plug holder 430 that is substantially frustoconically shaped may be positioned within the syringe body 420 such that the distal surface 434 contacts a complementary (e.g., substantially conical) interior surface at the distal end 424 of the syringe body 420.

The plug holder 430 may include a plurality of protrusions, such as the plurality of fins 435 of the illustrated embodiment. The fins 435 may extend radially outward from the remaining portion of the plug holder 430. In the depicted embodiment, the fins 435 also extend longitudinally along an outer surface of plug holder 430. The fins 435 may be configured to engage with an inner surface of the syringe body 420 (see FIGS. 4 and 5) to secure the plug holder 430 within the syringe body 420. In other words, the fins 435 may form an interference fit with the inner surface of the syringe body 420. The fins 435 may prevent the plug holder 430 from moving relative to the syringe body 420 during operation of the medical device 400.

Because the fins 435 protrude radially outward from the remaining portion, or nominal outside diameter, of the plug holder 430, the plug holder 430 may be disposed such that there is an annular gap 436 between the inside diameter of the syringe body 420 and the nominal outside diameter of the plug holder 430. The annular gap 436 may thus define an open space between the syringe body 420 and the plug holder 430. Along the longitudinal portion of the plug holder 430 on which the fins 435 are disposed the annular gap 436 may comprise one or more gaps 436 circumferentially between the fins 435 and radially between the plug holder 430 and the syringe body 420. Along the longitudinal portion of the plug holder 430 that does not include the fins 435, the annular gap 436 extends continuously around the plug holder 430 circumferentially. The radial height of the gaps 436 may be determined by the height of the fins 435. As described in further detail below, these gaps 436 may form one or more flow paths or pathways that permit the flow of fluid around a periphery of the plug holder 430.

The plug holder 430 may also include a shoulder 438 that is configured to restrict proximal displacement of the plug 440 during operation of the medical device 400. In the depicted embodiment, the shoulder 438 comprises an annular protrusion that extends inward (e.g., toward a longitudinal axis of the plug holder 430) from the remaining portions of the plug holder 430. The shoulder 438 may define a proximal portion of the lumen 431 that is relatively narrow in comparison to a distal portion of the lumen 431. In other words, a proximal portion of the lumen 431 that is defined by the shoulder 438 may have a smaller diameter than a distal portion of the lumen 431. Further, the distal portion of the lumen 431, meaning the portion of the lumen 431 located distal of the shoulder 438, may define a cavity configured to retain or receive the plug 440. As shown, the cavity may be centrally disposed in the plug holder 430 and may be aligned with an orifice at the distal end 424 of the syringe body 420.

The medical device 400 may be used to deliver a plug 440 to a patient. For example, in some embodiments, a practitioner may obtain a medical device 400 that includes a plunger 410, a syringe body 420, and a plug holder 430. The plug holder 430 may have a plug 440 disposed within a lumen 431 that extends longitudinally along a length of the plug holder 430. The plunger 410 may initially be disposed such that the plunger 410 abuts against the proximal surface 433 of the plug holder 430.

Liquid, such as water, saline, contrast, any mixture thereof, or any other fluid, may then be drawn into the medical device 400 to wet the plug 440 and introduce fluid into the reservoir 426 within the syringe body 420. The reservoir 426 may thus comprise a chamber within the syringe body 420. The plunger 410 may be retracted within the syringe body 420 while the distal end of the syringe body 420 is disposed within the liquid. As the plunger 410 is retracted in this manner, fluid may be drawn into the reservoir 426 of the syringe body 420 in via two different pathways. Stated another way, application of a negative pressure within the reservoir 426 of the syringe body 420 may tend to draw fluid into the syringe body 420 through the orifice at the distal end 424 of the syringe body 420. Negative pressure within the reservoir 426 may draw fluid through one or both of the fluid pathways as further detailed below.

First, as the plunger 410 is retracted, fluid may be drawn into the lumen 431, pass through (and thereby wet) the plug 440, and exit the proximal end of the plug holder 430 to thereby enter the reservoir 426 of the syringe body 420. The shoulder 438 of the plug holder 430 may prevent proximal displacement of the plug 440 past the shoulder 438, thereby ensuring that the plug 440 is not inadvertently sucked into the reservoir 426 of the syringe body 420. In other words, the shoulder 438 may engage with the plug 440, thereby inhibiting or restricting proximal displacement of the plug 440. Wetting of the plug 440 may increase the lubricity of the plug 440, thereby facilitating both ejection of the plug 440 from the plug holder 430 and advancement of the plug 440 through a lumen of an elongate tube to an interior portion (e.g., a void) of a patient. In some embodiments, the plug 440 may also swell as it wets, and may thus partially occlude or disrupt fluid flow through the lumen 431.

Second, instead of passing through the plug 440, fluid may be drawn into a distal portion of the lumen 431, pass through the side channel 432 to one or more gaps 436 disposed around a periphery of the plug holder 430, and then travel proximally through the one or more gaps past the proximal end of the plug holder 430 to enter into the reservoir 426 of the syringe body 420.

The two pathways described above may both operate to fill the reservoir 426 of the syringe body 420. For example, as the plunger 410 is initially retracted, fluid may primarily follow the first pathway (i.e., through the plug 440). In some embodiments, as fluid passes through the plug 440, the plug 440 is wetted. Again, such wetting may obstruct further fluid flow through the plug 440. In some embodiments, the plug 440 may begin to swell as it is wetted, further contributing to obstructing fluid flow through the plug 440. As the flow rate of fluid through the plug 440 decreases, a greater proportion of the fluid may instead pass through the second pathway (i.e., through the side channel 432 and the one or more gaps 436) to enter into the reservoir 426 of the syringe body 420.

Relative flow rates between the two pathways may depend, at least partially, on the relative sizes of the cross-sectional surface areas presented by the lumen 431 and the gaps 436. For example, in some embodiments, the cross-sectional surface area of the lumen 431 (where the cross-section is perpendicular to the longitudinal axis of the plug holder 430) is greater than the cross-sectional surface area of the gaps 436. Thus, a relatively large fluidic force may be applied to the plug 440 (both during retraction and advancement of the plunger 410), due to its positioning within a lumen having a relatively large cross-sectional surface area in comparison with the cross-sectional surface area of the gaps 436.

If desired, any air bubbles that were introduced into the medical device 400 as the plunger 410 was retracted may be removed in the traditional manner (i.e., by orienting the medical device 400 such that distal end of the medical device 400 is pointed upward, tapping the medical device 400, and ejecting air bubbles by advancing the plunger 410 toward the distal end of the medical device 400.

Once both the plug has been wetted and a sufficient quantity of fluid has entered into the reservoir 426 of the syringe body 420, the practitioner may couple the distal end of the syringe body 420 to an elongate tube, such as an introducer sheath or catheter. The introducer sheath or catheter may be in fluid communication with a void into which the plug 440 is to be inserted. For example, the distal end of the syringe body 420 may be coupled to a proximal end of an introducer sheath used in a biopsy procedure as described above.

The practitioner may advance the plunger 410 toward a distal end 424 of the syringe body 420, thereby distally displacing fluid in the reservoir 426. As the fluid is distally displaced, the fluid may encounter the proximal surface 433 of the plug holder 430. In embodiments, such as the embodiments in which the proximal surface 433 is concave and/or frustoconically shaped, the proximal surface 433 may direct (e.g., funnel) fluid flow into the central lumen 431. (The shape of the proximal surface 433 may also mate with, and/or provide a seat for, the seal 414 of the plunger 410.) Such fluid may exert a distal force on the plug 440 disposed within the central lumen 431, thereby causing distal displacement and ejection or deployment of the plug 440 from the plug holder 430 into the elongate tube that is in fluid communication with the void. As the plunger 410 is advanced, the displaced fluid may push plug 440 through the elongate tube and into the desired void. (Stated another way, application of positive pressure to the reservoir 426 may tend to force the plug 440 and fluid from the reservoir 426 and out of the orifice at the distal end 424 of the syringe body 420.) The inserted plug 440 may serve any suitable purpose, such as obstructing fluid flow, inducing blood coagulation, and/or providing a scaffold to promote tissue growth.

Figure 36:
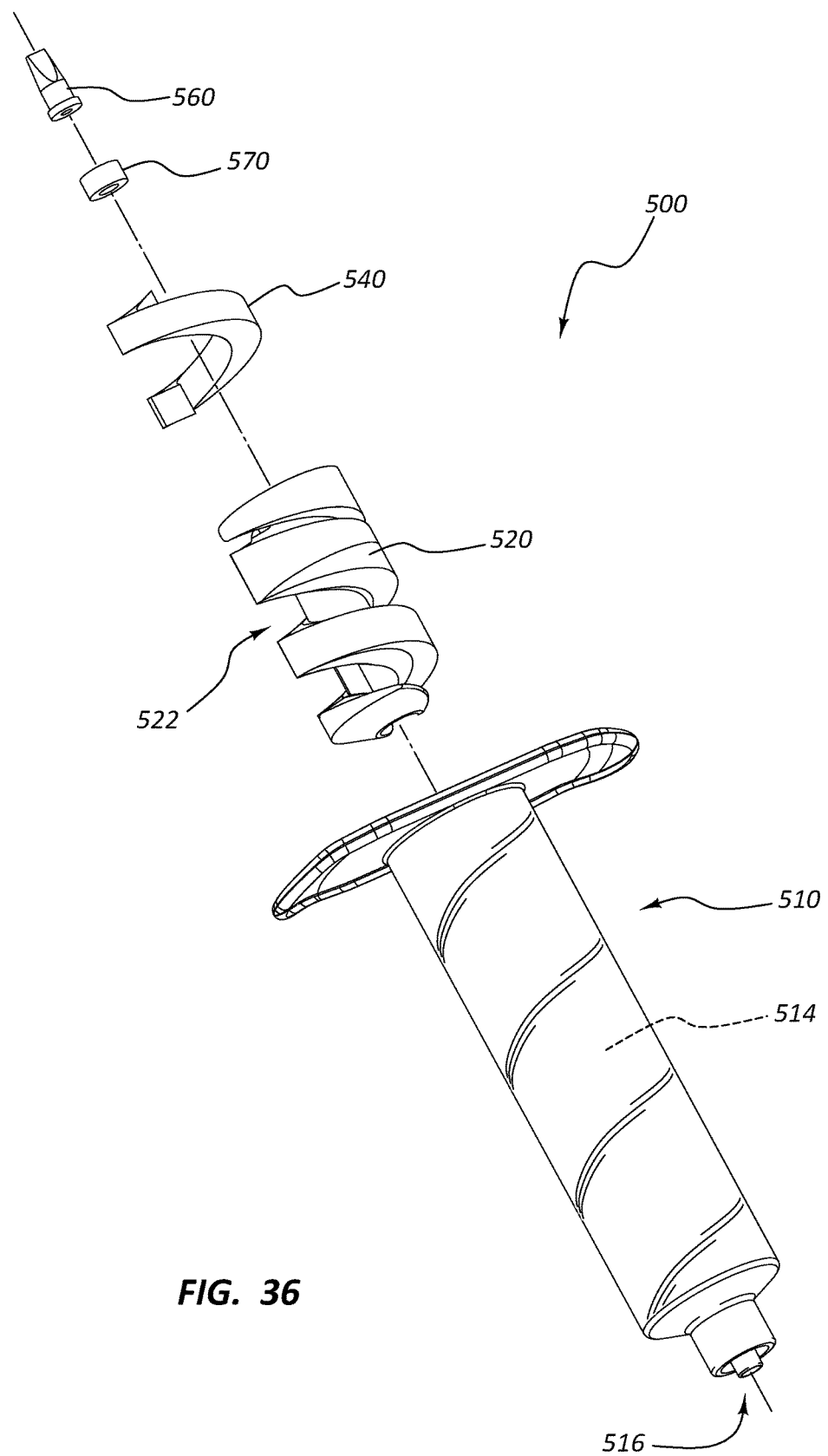
FIG. 36 is an exploded perspective view of a medical device for delivering a medical plug to a patient.
Figure 37:
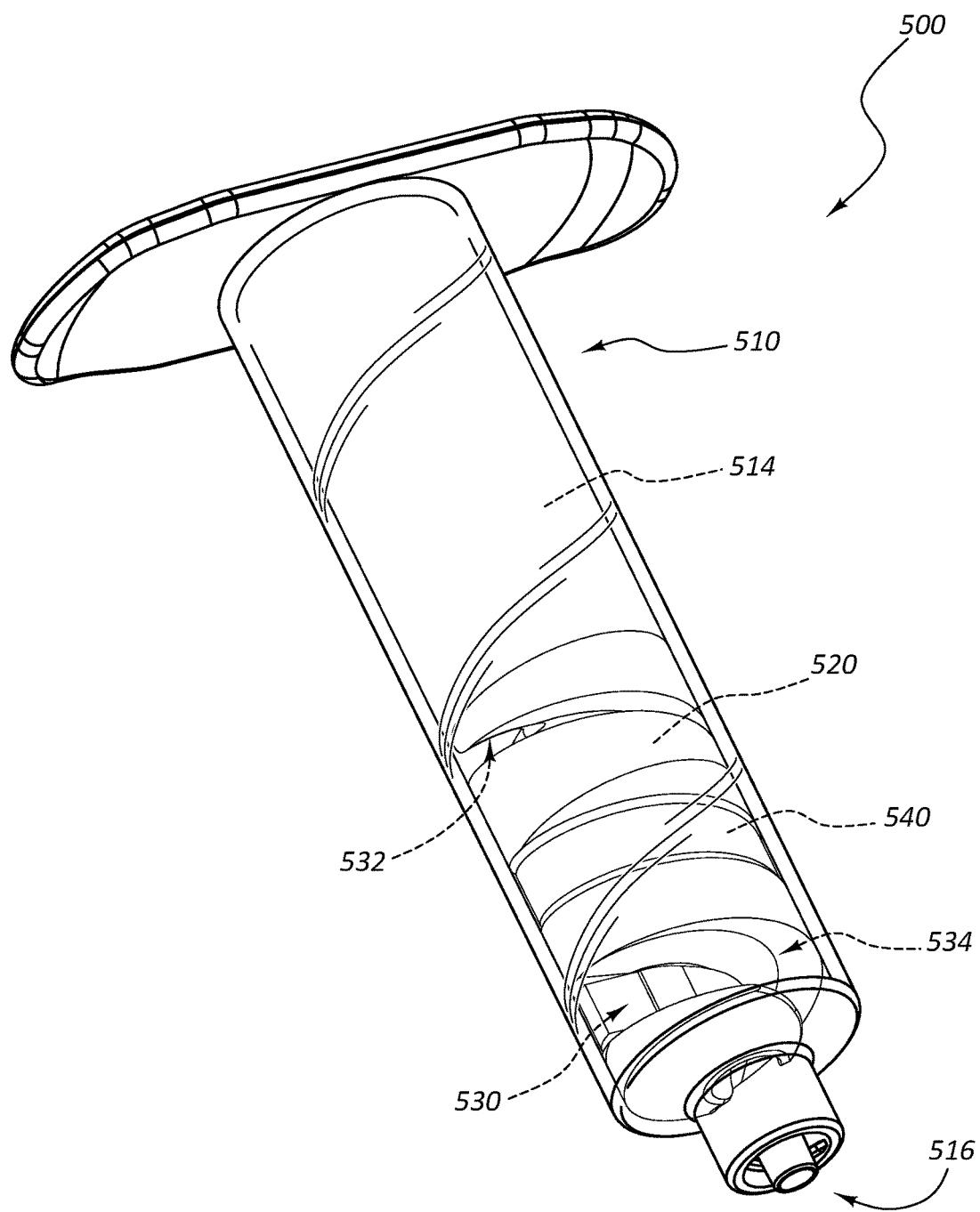
FIG. 37 is a perspective view of the medical device of FIG. 36.
Figure 38:
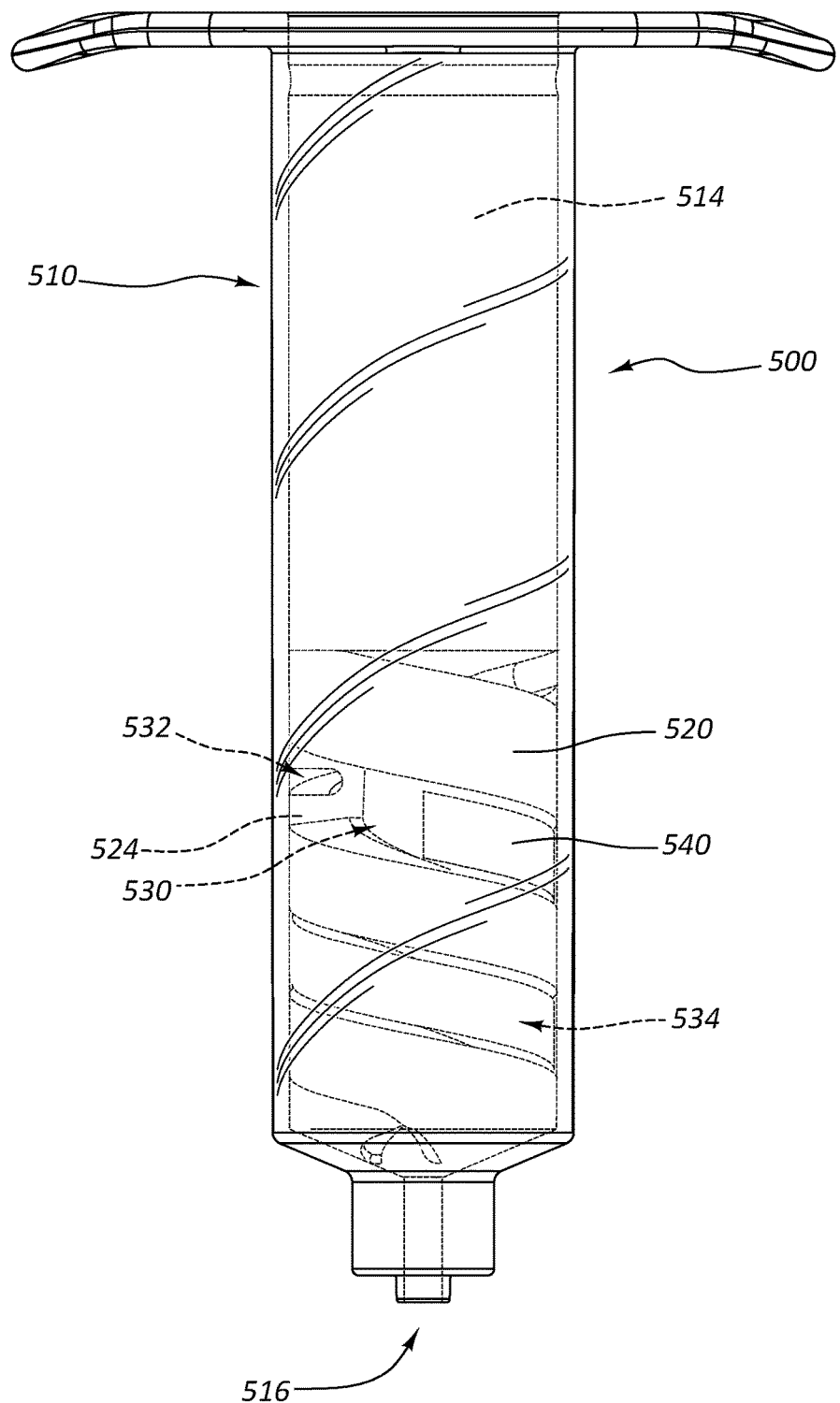
FIG. 38 is a side view of the medical device of FIGS. 36-37.
Figure 39:
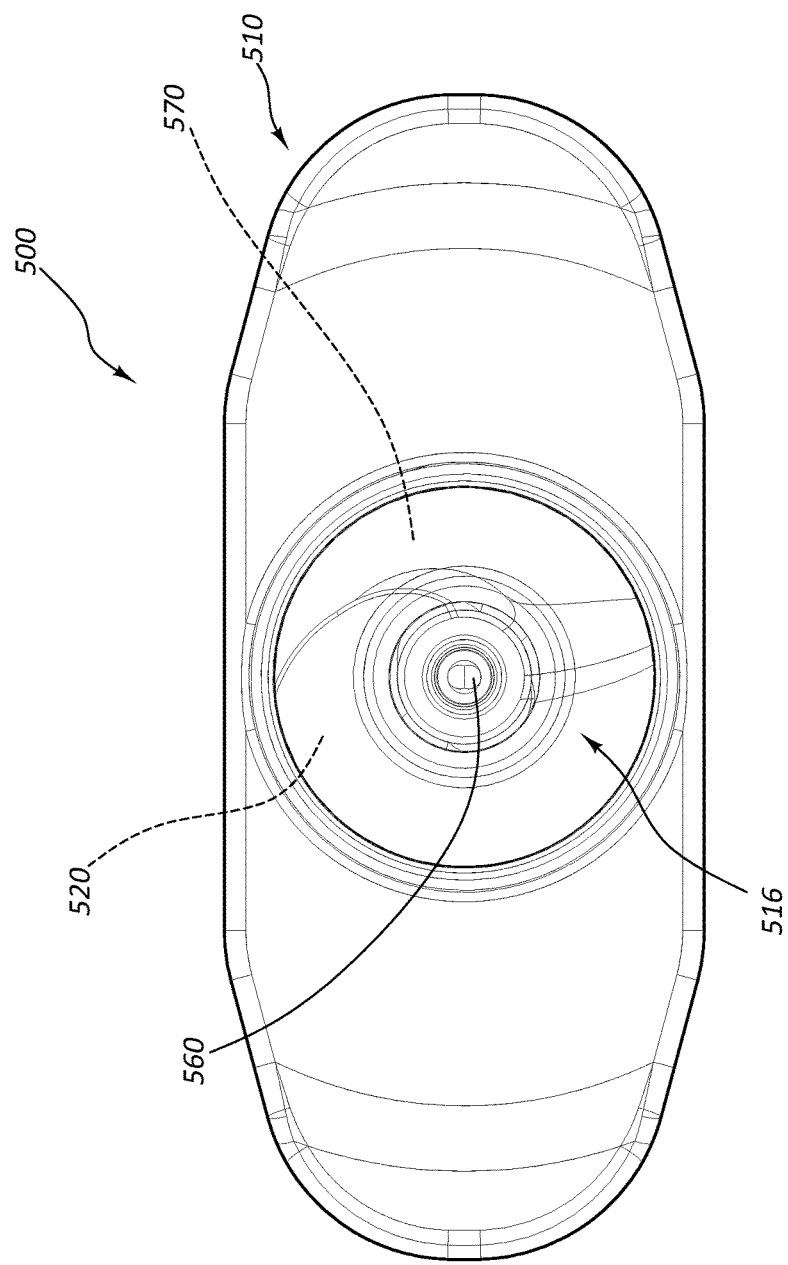
FIG. 39 is an end-on view of the medical device of FIGS. 36-38 from a position that is distal of the medical device.
Figure 40:
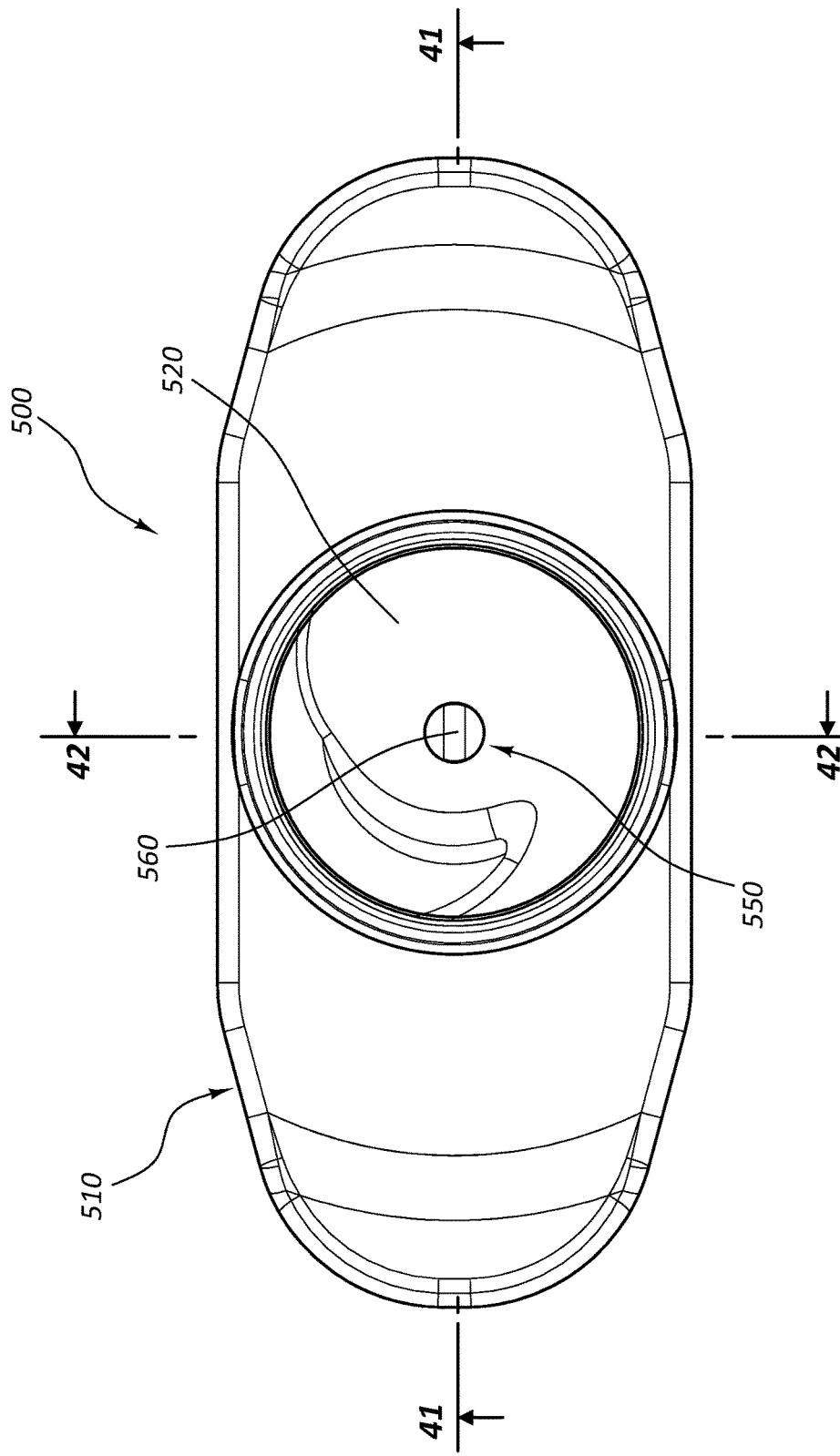
FIG. 40 is an end-on view of the medical device of FIGS. 36-39 from a position that is proximal of the medical device.
Figure 41:
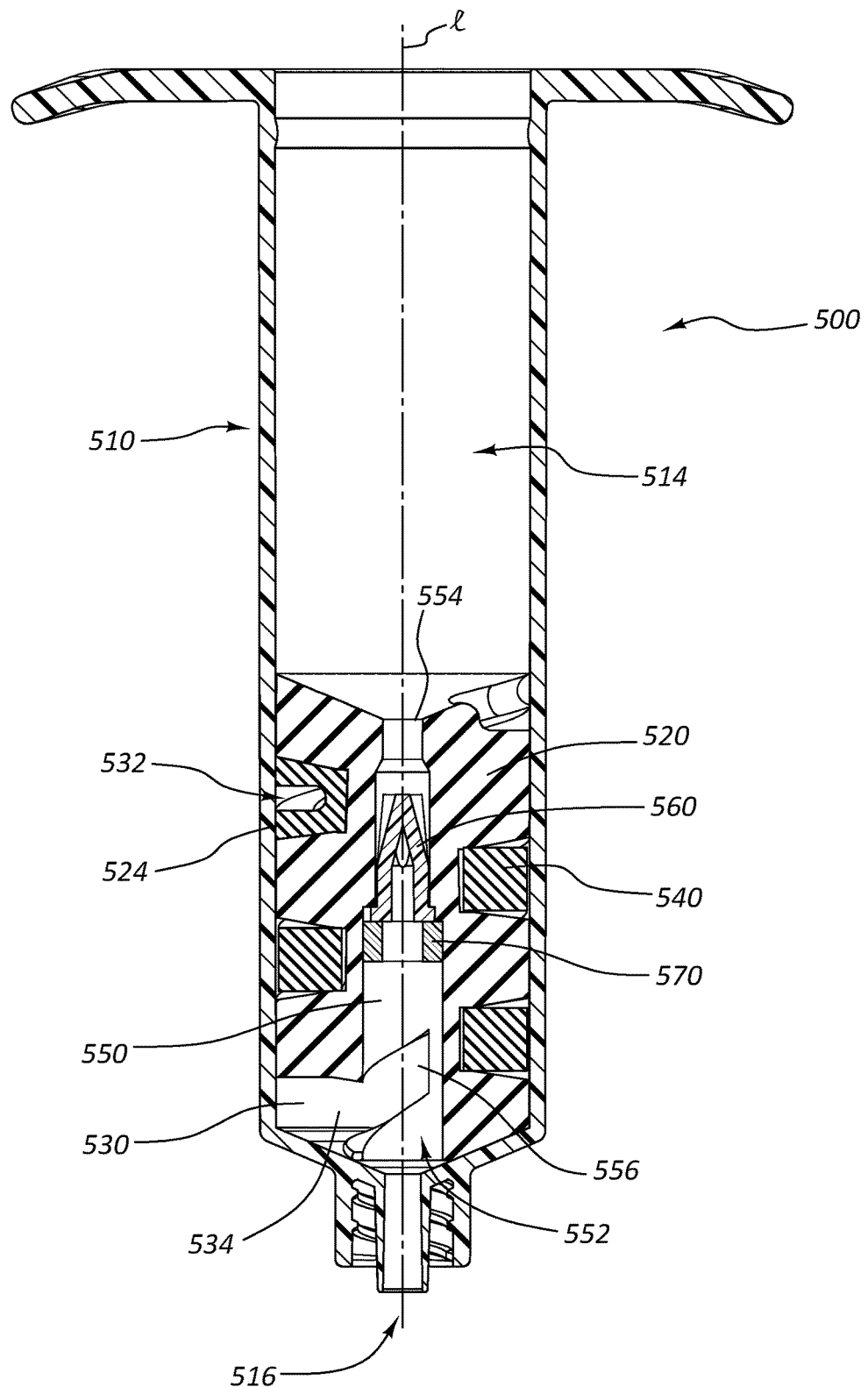
FIG. 41 is a cross-sectional view of the medical device of FIGS. 36-40.
Figure 42:
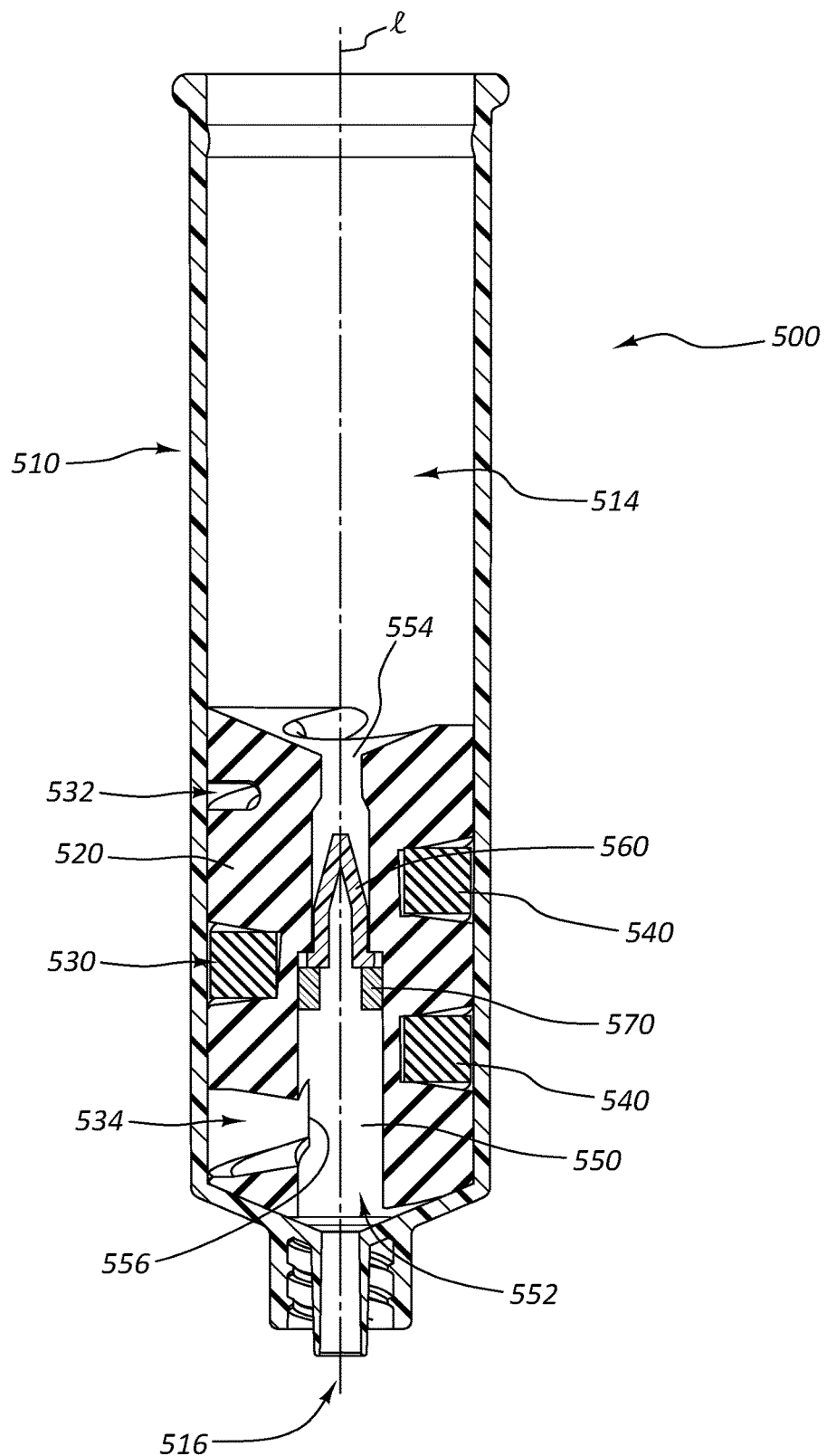
FIG. 42 is an alternative cross-sectional view of the medical device of FIGS. 36-41.

FIGS. 36-42 provide alternative views of a medical device 500 (which is alternatively referred to as a medical plug delivery device) for delivering one or more plugs to one or more interior regions of a patient. More particularly, FIG. 36 provides an exploded view of the medical device 500. FIG. 37 provides a perspective view of the medical device 500. FIG. 38 provides a side view of the medical device 500. FIG. 39 provides an end-on view of the medical device 500 from a position that is distal of the medical device 500. FIG. 40 provides an end-on view of the medical device 500 from a position that is proximal of the medical device 500. And FIGS. 41 and 42 provide alternative cross-sectional views of the medical device 500.

As shown in FIGS. 36-42, the medical device 500 may include a fluid delivery device (such as a syringe 510), a frame insert 520, and one or more medical plugs 540.

The syringe 510 may include a plunger (not shown) that is configured to be at least partially disposed within the body of the syringe 510 such that advancement and retraction of the plunger causes displacement of fluid within a reservoir 514 in the syringe 510. The syringe 510 may include a distal port 516 that is in fluid communication with the reservoir 514. In the depicted embodiment, the distal port 516 of the syringe 510 is a male Luer connection, although other ports are also within the scope of this disclosure. In some embodiments, the syringe 510 is a standard, commercially available syringe. In other embodiments, the syringe 510 may differ in one or more ways from standard, commercially available syringes. The syringe 510 may be any suitable size. In some embodiments, the syringe 510 may be capable of holding enough fluid to facilitate deployment of multiple plugs 540 into a patient. In some embodiments, the syringe 510 is capable of holding at least 3 mL, at least 5 mL, and/or at least 10 mL of fluid. In some embodiments, the syringe 510 (or a portion thereof) is substantially transparent, thereby allowing the practitioner to visualize wetting and ejection of one or more medical plug(s) 540 as described below. In other embodiments, the syringe 510 is opaque.

Figure 43:
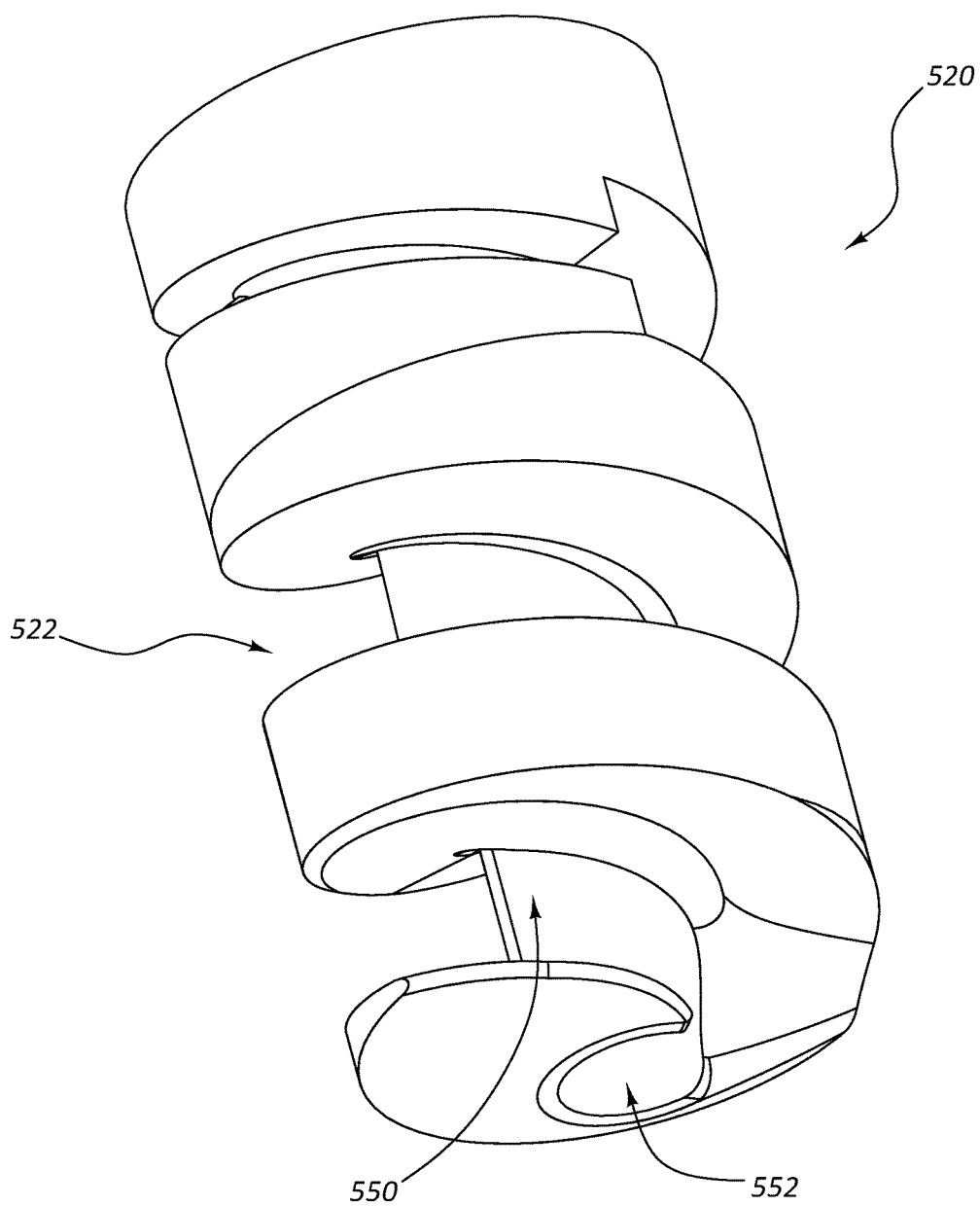
FIG. 43 is a perspective view of a frame insert of the medical device of FIGS. 36-42.
Figure 44:
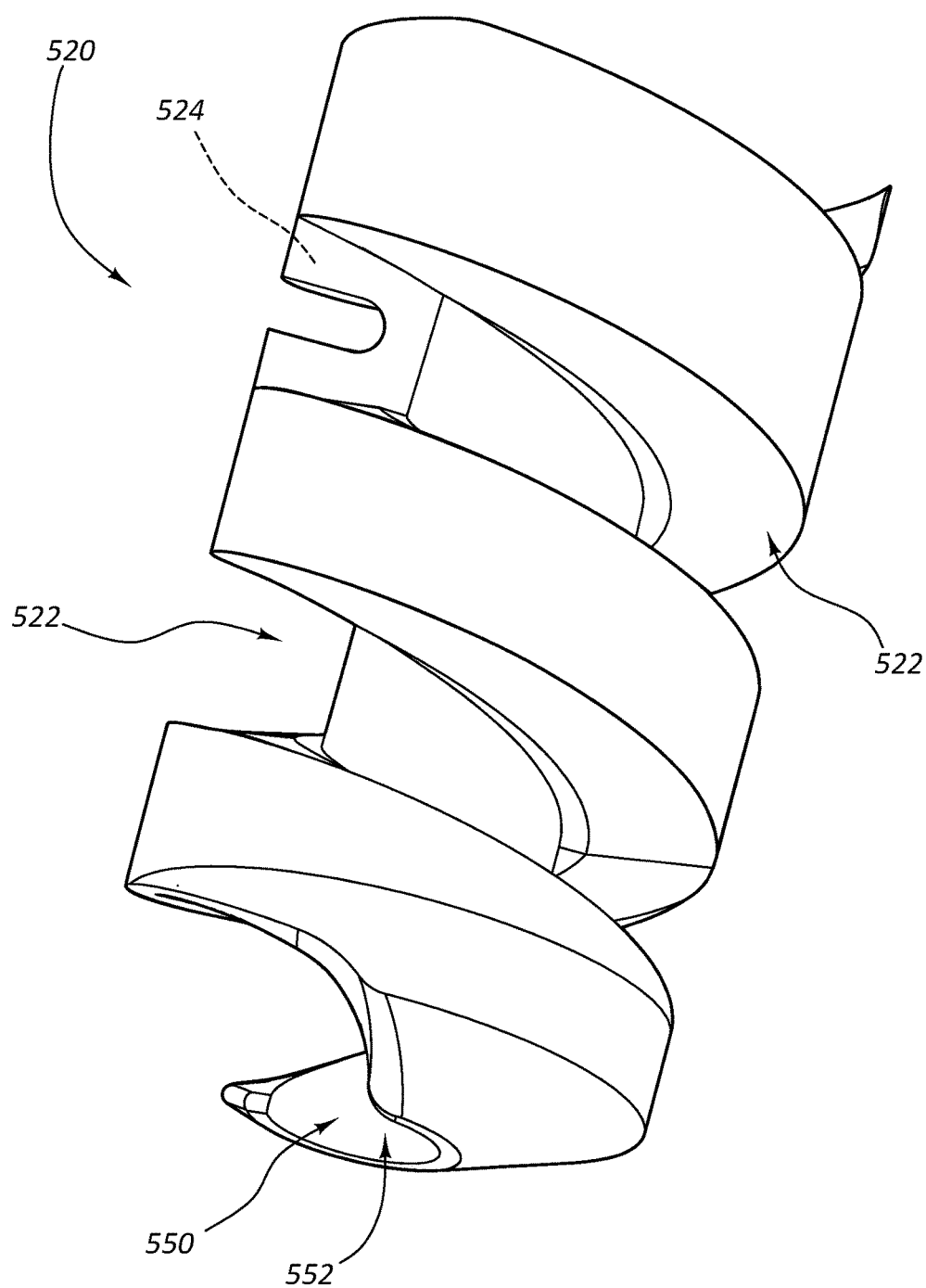
FIG. 44 is an alternative perspective view of the frame insert of the medical device of FIGS. 36-42.

The frame insert 520 may be configured to be disposed within the body of the syringe 510. For example, in some embodiments, the frame insert 520 may be secured within the syringe 510 via an interference fit (e.g., a sloped side of the frame insert 520 may form an interference fit with the walls of the syringe 510). In other embodiments, the frame insert 520 is secured within the syringe 510 in some other manner. In some embodiments, the frame insert 520 may be disposed within the syringe 510 such that the frame insert 520 and the syringe 510 form a non-linear lumen that is disposed radially outward from a longitudinal axis of the syringe 510, such as a helical lumen 530. For example, the frame insert 520 may include a helical groove 522 that extends helically around an exterior of the frame insert 520 (see FIGS. 43 and 44, which provide alternative perspective views of the frame insert 520). The helical groove 522 may cooperate with the syringe 510 to form the helical lumen 530. The helical lumen 530 and the helical groove 522 may be in fluid communication with both the distal port 516 of the syringe 510 and the reservoir 514 of the syringe 510 that is disposed proximal of the frame insert 520.

The helical lumen 530 may include a proximal portion 532 and a distal portion 534 (see FIGS. 37, 38, 41, and 42). In some embodiments, the proximal portion 532 of the helical lumen 530 is narrower than the distal portion 534 of the helical lumen 530. Stated differently, a proximal portion of the helical groove 522 may be narrower than a distal portion of the helical groove 522. In some embodiments, the frame insert 520 includes a ledge 524 or shoulder at the transition between the distal portion 534 of the helical lumen 530 and the proximal portion 532 of the helical lumen 530. The shoulder or ledge 524 of the frame insert 520 may engage or abut the medical plug 540 preventing proximal displacement of the medical plug 540 past the ledge 524.

In some embodiments, the helical lumen 530 accommodates only a single plug 540. In other embodiments, the helical lumen 530 is sized to accommodate at least two medical plugs. For example, in some embodiments, a first medical plug 540 within the helical lumen 530 may be disposed distal of a second medical plug within the helical lumen 530. Stated differently, one or more medical plugs 540 may be disposed within the helical lumen 530 of the medical device 500. In some embodiments, the one or more medical plugs 540 may be disposed within the helical groove 522 prior to insertion of the frame insert 520 into the body of the syringe 510.

The medical plug(s) 540 may be of any suitable composition, shape, and/or size. For example, in some embodiments, the medical plug(s) 540 include or consist essentially of a bioabsorbable material. In some embodiments, the bioabsorbable material (or a portion thereof) is derived from animal tissue, such as pig skin or cow skin. In some embodiments, the bioabsorbable material is a collagen-containing material, such as a gelatin foam from an animal source. In other or further embodiments, the bioabsorbable material (or a portion thereof) is a synthetic polymer, such as polylactic acid, polyglycolide, or poly(lactic-co-glycolic acid). In some embodiments, the medical plug(s) 540 include or consist essentially of a non-bioabsorbable material, such as polyvinyl alcohol or polyvinyl acetate. In some embodiments, the medical plug(s) 540 include a dye. The dye may facilitate visualization of the medical plug(s) 540 when the medical plug(s) 540 is disposed within the helical lumen 530. In some embodiments, the medical plug(s) 540 may change colors when contacted with fluid (e.g., water or saline), thereby allowing a practitioner to visually determine when the medical plug(s) 540 have been wetted or otherwise hydrated.

The medical plug(s) 540 may be generally elongate in shape. For example, in some embodiments, each medical plug 540 is an elongate piece of material that has been rolled into a substantially cylindrical shape of between 1 mm and 5 mm (e.g., approximately 2 mm) in diameter. The medical plug 540 may have a length that is at least 2-fold, at least 5-fold, and/or at least 10-fold longer than the diameter of the plug 540. In some embodiments, the medical plug 540 is between 10 mm and 520 mm in length. For example, the medical plug 540 may be between 10 mm and 30 mm, between 20 mm and 40 mm, between 30 mm and 50 mm, between 40 mm and 60 mm, between 50 mm and 70 mm, between 60 mm and 80 mm, between 70 mm and 90 mm, between 80 mm and 500 mm, between 90 mm and 510 mm, or between 500 mm to 520 mm in length. In some embodiments, the medical plug 540 is longer than the frame insert 520. The configuration of the helical lumen 530 allows the medical device 500 to contain and deploy a medical plug 540 that is longer than the frame insert 520.

In some embodiments, such as the embodiment shown in FIGS. 36-42, the frame insert 520 may include a central channel 550. Stated differently, an interior surface of the frame insert 520 may define the central channel 550. The central channel 550 may extend from a distal end of the frame insert 520 to a proximal end of the frame insert 520. Additionally or alternatively, the central channel 550 may extend along and/or be centered around the longitudinal axis (/) of the syringe 510 (see FIGS. 36-42). In some embodiments, the central channel 550 is a linear channel that extends through the frame insert 520. The central channel 550 may be in fluid communication with both the distal port 516 and the reservoir 514 of the syringe 510. In some embodiments, the channel 550 includes a distal opening 552 that is larger than the proximal opening 554 (see FIGS. 36-42). In some embodiments, a side wall of the channel 550 includes an opening 556. The opening 556 may connect the helical lumen 530 with the central channel 550 adjacent the distal end of the frame insert 520.

In some embodiments, the medical device 500 further includes a valve 560. In some embodiments, the valve 560 is disposed within the central channel 550 of the frame insert 520. In the depicted embodiment, the valve 560 is a one-way valve or a check valve that permits the flow of fluid across the valve 560 in a proximal direction but inhibits flow in a distal direction. The valve 560 may be secured within the central channel 550 in any suitable manner. For example, in the depicted embodiment, the valve 560 is secured within the central channel 550 by a securement element 570. The securement element 570 is a ring that is disposed within the central channel 550 that forms an interference fit with the side wall of the channel 550. The securement element 570 abuts against a distal surface of the valve 560, sandwiching a portion of the valve 560 between the securement element 570 and a ledge of the central channel 550, thereby securing the valve 540 within the central channel 550. In some embodiments, the valve 540 is secured within the central channel 550 via an interference fit.

The medical device 500 may be used to deploy one or more plugs to an interior region (e.g., a void) of a patient. In some embodiments, a practitioner may obtain the medical device 500 with the frame insert 520 disposed within the body of the syringe 510 such that one or more medical plugs 540 are disposed in a helical lumen 530 formed by the frame insert 520 and the syringe 510. In other embodiments, the practitioner may insert one or more medical plugs 540 into a groove 522 of the frame insert 520. The frame insert 520 may then be inserted into the body of the syringe 510.

With the frame insert 520 and the medical plugs 540 disposed within the body of the syringe 510, liquid (e.g., water, saline, contrast, any mixture thereof, or any other fluid) may then be drawn into the medical device 500 to wet the medical plug 540 and introduce fluid into the reservoir 514 of the syringe 510. For example, a plunger (not shown) may be retracted within the body of the syringe 510 while the distal port 516 of the syringe 510 is disposed within the liquid. As the plunger is retracted in this manner, fluid may be drawn into the reservoir 514 of the syringe 510 via two different pathways. Stated another way, application of a negative pressure within the reservoir 514 of the syringe 510 may tend to draw fluid into the syringe 510 through the distal port 516 of the syringe 510. Negative pressure within the reservoir 514 may draw fluid through one or both of the fluid pathways as further detailed below.

First, as the plunger is retracted, fluid may be drawn into the helical lumen 530, pass through (and thereby wet) one or more medical plugs 540 disposed within the helical lumen 530, and exit the proximal end of the frame insert 520 to thereby enter the reservoir 514 of the syringe 510. The shoulder or ledge 524 of the frame insert 520 may prevent proximal displacement of the medical plug 540 past the ledge 524, thereby ensuring that the medical plug 540 is not inadvertently sucked into the reservoir 514 of the syringe 510. In other words, the ledge 524 may engage with or abut the medical plug 540, thereby preventing or restricting proximal displacement of the medical plug 540. In this manner, the helical lumen 530 may be designed to maintain one or more medical plugs 540 within the helical lumen 530 when a proximally directed flow of fluid passes through the helical lumen 530.

By passing the liquid through and/or around the medical plug(s) 540 in the manner described above, the medical plug(s) 540 may be wetted prior to deployment. Wetting of the medical plug(s) 540 may increase the lubricity of the medical plugs 540, thereby facilitating both ejection of the medical plug(s) 540 from the medical device 500 and advancement of the medical plug(s) 540 through a lumen of an elongate tube (e.g., a sheath or catheter) to one or more interior regions (e.g., a void) of a patient. In some embodiments, the medical plug(s) 540 may also swell as it becomes wetted, and may thus partially occlude or disrupt fluid flow through the helical lumen 530.

Second, instead of passing through the helical lumen 530 and/or the one or more medical plugs 540, fluid may be drawn into the central channel 550, pass through the one-way valve 560, and exit from the frame insert 520 into the reservoir 514 of the syringe 510.

The two pathways described above may both operate to fill the reservoir 514 of the syringe 510. In other words, the medical device 500 may be structured such that retraction of the plunger causes proximally directed fluid flow through both the helical lumen 530 and the central channel 550. For example, as the plunger is initially retracted, fluid may primarily follow the first pathway (i.e., through the helical lumen 530 and the one or more medical plugs 540). As fluid passes through the medical plug(s) 540, the medical plug(s) 540 may be wetted. In some embodiments, such wetting may cause the medical plug(s) 540 to swell, thereby obstructing further fluid flow through the medical plug(s) 540. As the flow rate of fluid through the helical lumen 530 decreases, a greater proportion of the fluid may instead follow the second pathway (i.e., through the central channel 550) to enter into the reservoir 514 of the syringe 510.

If desired, any air bubbles that were introduced into the medical device 500 as the plunger was retracted may be removed in the traditional manner (i.e., by orienting the medical device 500 such that the distal port 516 of the medical device 500 is pointed upward, tapping the medical device 500, and ejecting air bubbles by advancing the plunger toward the distal end of the medical device 500.

Once both the one or more medical plugs 540 have been wetted and a sufficient quantity of fluid has entered into the reservoir 514 of the syringe 510, the practitioner may couple the distal port 516 of the syringe 510 to an elongate tube, such as an introducer sheath or catheter. The elongate tube may be in fluid communication with a void into which the medical plug(s) 540 is to be inserted. For example, the distal port 516 of the syringe 510 may be coupled to a proximal end of an introducer sheath used in a biopsy procedure as described above.

The practitioner may advance the plunger toward a distal port 516 of the syringe 510, thereby distally displacing fluid in the reservoir 514. The one-way valve 560 may prevent fluid from passing through the central channel 550 as the fluid is distally displaced. In other words, the pathway through the central channel 550 may be closed as the plunger is advanced within the syringe 510.

With the pathway through the central channel 550 unavailable, the displaced fluid may pass through the helical lumen 530. Stated differently, the medical device 500 may be structured such that advancement of the plunger causes distally directed fluid to flow through the helical lumen 530 but not the central lumen 550. The distally displaced fluid may exert a distal force on the one or more medical plugs 540 disposed within the helical lumen 530. Such force may cause distal displacement and ejection or deployment of the medical plug(s) 540 from the medical device 500. The ejected medical plug(s) 540 may be further pushed through the elongate tube (e.g., an introducer sheath or catheter) and into the desired void. (Stated another way, application of positive pressure to the reservoir 514 may tend to force the medical plug(s) 540 out of the distal port 516 of the syringe 510.) The inserted plug(s) 540 may serve any suitable purpose, such as obstructing fluid flow, inducing blood coagulation, and/or providing a scaffold to promote tissue growth.

The embodiment depicted in FIGS. 36-42 depicts a single medical plug 540 for deployment. However, the medical device 500 may be used to deploy a plurality of medical plugs 540 as well. For example, in some embodiments, a plurality of medical plugs 540 may be disposed within the helical channel 530 of the medical device 500. For example, a first medical plug 540 may be disposed adjacent a distal end of the helical lumen 530 and a second medical plug 540 may be disposed within the helical lumen 530 at a position that is proximal of the first medical plug 540. Distal displacement of the plunger may cause deployment of both the first medical plug 540 and the second medical plug 540 into a void within a patient.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A medical plug delivery system, comprising:
a medical plug delivery device comprising a housing defining a cavity with a first end and a second end, wherein the housing comprises a distal connector configured to connect to a distal medical appliance in communication with a patient; and a plug cartridge defining a cavity with a first end and a second end configured to receive a medical plug, wherein the plug cartridge is disposed within the cavity of the housing, the plug cartridge comprising apertures in communication with the cavity of the housing;

wherein the housing further defines a shoulder at a proximal end of the cavity, the shoulder being configured to engage the medical plug and prevent the medical plug's movement proximal of the shoulder;

wherein the cavity of the plug cartridge is structured to frictionally engage the medical plug within the cavity of the plug cartridge until a distally directed flow of fluid passes through the cavity of the plug cartridge with sufficient force to overcome the engagement; and wherein the medical plug delivery system comprises at least two different fluid pathways.

2. The medical plug delivery system of claim 1, further comprising the medical plug configured to fill a void in the patient.

3. The medical plug delivery system of claim 1, wherein the housing further comprises a proximal connector.

4. The medical plug delivery system of claim 1, wherein the cavity of the plug cartridge comprises radially inwardly projecting detents configured to engage the medical plug in the cavity of the plug cartridge and to permit fluid flow past the medical plug.

5. The medical plug delivery system of claim 1, wherein the housing further comprises a frustoconical shaped distal end configured to guide the displaced medical plug into the medical appliance in communication with the patient.

6. The medical plug delivery system of claim 1, wherein a cross-section of the plug cartridge that is perpendicular to a longitudinal axis of the plug cartridge defines a perimeter of a portion of the cavity of the plug cartridge, wherein the perimeter comprises:
 a plurality of inward-most points at a first radius from the longitudinal axis of the plug cartridge;
 a plurality of outward-most points at a second radius from the longitudinal axis of the plug cartridge, wherein the second radius is longer than the first radius; and
 wherein the plurality of outward-most points and the plurality of inward-most points extend continuously along a longitudinal length of the channel cavity.

7. The medical plug delivery system of claim 1, wherein the medical plug delivery device further comprises a proximal connector configured to connect to a proximal fluid delivery device.

8. A medical plug delivery device, the device comprising:
 a housing defining a channel that extends from a proximal end of the medical plug delivery device to a distal end of the medical plug delivery device, wherein the channel is configured to receive a medical plug;
 a distal connector configured to connect to a distal medical appliance that is in fluid communication with a patient; and
 a proximal connector configured to connect to a proximal fluid delivery device;
 wherein a cross-section of the housing that is perpendicular to a longitudinal axis of the housing defines a perimeter of a portion of the channel, wherein the perimeter comprises:
  a plurality of inward-most points at a first radius from the longitudinal axis of the housing, wherein each inward-most point is disposed on an apex of a convex region curve; and
  a plurality of outward-most points at a second radius from the longitudinal axis of the housing, wherein the second radius is longer than the first radius, wherein each outward-most point is disposed on an apex of a concave region curve,
  wherein the plurality of inward-most points and the plurality of outward-most points are spaced radially apart along the perimeter, and
  wherein the plurality of outward-most points and the plurality of inward-most points extend continuously along a longitudinal length of the channel.

9. The medical plug delivery device of claim 8, wherein each point of the plurality of inward-most points is separated from an adjacent inward-most point by an outward most point.

10. The medical plug delivery device of claim 8, wherein the channel comprises a tapering region that tapers toward the longitudinal axis of the housing.

11. The medical plug delivery device of claim 8, further comprising an elongate, biocompatible medical plug disposed within the channel.

12. The medical plug delivery device of claim 11, wherein the device is configured such that when a fluid flows in a distal direction through the channel, the fluid hydrates the medical plug and ejects the medical plug through a distal opening at the distal end of the housing medical plug delivery device.

13. The medical plug delivery device of claim 11, wherein the medical plug is frictionally engaged by the plurality of inward-most points.

14. The medical plug delivery device of claim 8, wherein the housing further defines a shoulder at a proximal end of the channel, the shoulder being configured to engage the medical plug and restrict the medical plug's movement proximal of the shoulder.

* * * * *

UNITED STATES PATENT AND TRADEMARK OFFICE
CERTIFICATE OF CORRECTION

PATENT NO. : 11,964,136 B2
APPLICATION NO. : 15/476675
DATED : April 23, 2024
INVENTOR(S) : Lampropoulos et al.

It is certified that error appears in the above-identified patent and that said Letters Patent is hereby corrected as shown below:

In the Claims

Column 28, Line 16, Claim 8 reads, "… an apex of a convex region curve; …" which should read, "… an apex of a convex curve; …"
Column 28, Line 21, Claim 8 reads, "… an apex of a convex region curve; …" which should read, "… an apex of a convex curve; …"
Column 28, Line 43, Claim 12 reads, "… at the distal end of the housing medical plug …" which should read, "… at the distal end of the medical plug …"

Signed and Sealed this
Twenty-third Day of July, 2024

Katherine Kelly Vidal
Director of the United States Patent and Trademark Office